(12) United States Patent
Kenny et al.

(10) Patent No.: US 12,043,671 B2
(45) Date of Patent: Jul. 23, 2024

(54) ANTIBODIES TARGETING AN AMPHIREGULIN-DERIVED CELL SURFACE NEO-EPITOPE

(71) Applicant: Gundersen Lutheran Medical Foundation, Inc., La Crosse, WI (US)

(72) Inventors: Paraic Anthony Kenny, La Crosse, WI (US); Kristopher Andrew Lofgren, Dover, MN (US); Sreeja Sreekumar, Poway, CA (US)

(73) Assignee: Gundersen Lutheran Medical Foundation, Inc., La Crosse, WI (US)

( * ) Notice: Subject to any disclaimer, the term of this patent is extended or adjusted under 35 U.S.C. 154(b) by 0 days.

(21) Appl. No.: 17/836,517

(22) Filed: Jun. 9, 2022

(65) Prior Publication Data

US 2022/0411532 A1    Dec. 29, 2022

Related U.S. Application Data

(60) Provisional application No. 63/211,356, filed on Jun. 16, 2021.

(51) Int. Cl.
C07K 16/30 (2006.01)
A61P 35/00 (2006.01)

(52) U.S. Cl.
CPC .............. *C07K 16/30* (2013.01); *A61P 35/00* (2018.01); *C07K 2317/21* (2013.01); *C07K 2317/24* (2013.01); *C07K 2317/565* (2013.01); *C07K 2317/73* (2013.01); *C07K 2317/76* (2013.01)

(58) Field of Classification Search
CPC .............. C07K 16/30; C07K 2317/21; C07K 2317/24; C07K 2317/565; C07K 2317/32; A61P 35/00
See application file for complete search history.

(56) References Cited

U.S. PATENT DOCUMENTS

| | | |
|---|---|---|
| 4,634,664 A | 1/1987 | Oestberg |
| 4,634,666 A | 1/1987 | Engleman |
| 4,675,187 A | 6/1987 | Konishi |
| 4,699,784 A | 10/1987 | Shih |
| 4,816,397 A | 3/1989 | Boss |
| 4,816,567 A | 3/1989 | Cabilly |
| 4,824,659 A | 4/1989 | Hawthorne |
| 5,004,692 A | 4/1991 | Tso |
| 5,057,313 A | 10/1991 | Shih |
| 5,525,338 A | 6/1996 | Goldenberg |
| 5,530,101 A | 6/1996 | Queen |
| 5,545,806 A | 8/1996 | Lonberg |
| 5,585,089 A | 12/1996 | Queen |
| 5,677,427 A | 10/1997 | Goldenberg |
| 5,693,761 A | 12/1997 | Queen |
| 5,693,762 A | 12/1997 | Queen |
| 5,697,902 A | 12/1997 | Goldenberg |
| 5,698,413 A | 12/1997 | Hollingshead |
| 5,716,595 A | 2/1998 | Goldenberg |
| 5,807,715 A | 9/1998 | Morrison |
| 5,866,692 A | 2/1999 | Shitara |
| 5,939,598 A | 8/1999 | Kucherlapati |
| 5,961,955 A | 10/1999 | Shochat |
| 5,969,108 A | 10/1999 | McCafferty |
| 5,997,867 A | 12/1999 | Waldmann |
| 6,054,297 A | 4/2000 | Carter |
| 6,071,490 A | 6/2000 | Griffiths |
| 6,075,181 A | 6/2000 | Kucherlapati |
| 6,114,598 A | 9/2000 | Kucherlapati |
| 6,120,767 A | 9/2000 | Robinson |
| 6,150,584 A | 11/2000 | Kucherlapati |
| 6,162,963 A | 12/2000 | Kucherlapati |
| 6,180,370 B1 | 1/2001 | Queen |
| 6,180,377 B1 | 1/2001 | Morgan |
| 6,187,284 B1 | 2/2001 | Griffiths |
| 6,210,671 B1 | 4/2001 | Co |
| 6,306,393 B1 | 10/2001 | Goldenberg |
| 6,329,508 B1 | 12/2001 | Friden |
| 6,331,415 B1 | 12/2001 | Cabilly |
| 6,350,861 B1 | 2/2002 | Co |
| 6,548,275 B2 | 4/2003 | Goldenberg |

(Continued)

FOREIGN PATENT DOCUMENTS

| | | |
|---|---|---|
| EP | 0519596 A1 | 12/1992 |
| WO | WO 91/10741 A1 | 7/1991 |

(Continued)

OTHER PUBLICATIONS

Sela-Culang, I et. al. "The structural basis of antibody-antigen recognition", 2013, Frontiers in Immunology, 4(302), 1-13. (Year: 2013).*
Tiller, Kathryn E et. al. "Arginine mutations in antibody complementarity-determining regions display context-dependent affinity/specificity trade-offs", 2017, J. Biol. Chem., 292(40), 16638-16652. (Year: 2017).*
Gussow, Detlef and Seemann, Gerhard. "Humanization of Monoclonal Antibodies", 1991, Methods in Enzymology, 203, 99-121. (Year: 1991).*

(Continued)

*Primary Examiner* — Nelson B Moseley, II
*Assistant Examiner* — Alyssa Rae Stonebraker
(74) *Attorney, Agent, or Firm* — Andrus Intellectual Property Law, LLP

(57) ABSTRACT

Antibodies and antibody-drug conjugates that selectively bind to a membrane-associated extracellular portion of a cleaved amphiregulin precursor protein; methods of using the antibodies and antibody-drug conjugates to detect and inhibit the growth of neoplastic cells; pharmaceutical compositions containing the antibodies and/or antibody-drug conjugates as the active ingredient(s); kits containing the antibodies and/or antibody-drug conjugates.

23 Claims, 28 Drawing Sheets

(19 of 28 Drawing Sheet(s) Filed in Color)

Specification includes a Sequence Listing.

(56) References Cited

U.S. PATENT DOCUMENTS

| | | | |
|---|---|---|---|
| 6,653,104 | B2 | 11/2003 | Goldenberg |
| 6,962,702 | B2 | 11/2005 | Hansen |
| 6,982,321 | B2 | 1/2006 | Winter |
| 7,033,572 | B2 | 4/2006 | Goldenberg |
| 7,087,409 | B2 | 8/2006 | Barbas, III |
| 7,147,856 | B2 | 12/2006 | Govindan |
| 7,259,240 | B2 | 8/2007 | Zhou |
| 10,852,304 | B2 * | 12/2020 | Couto .............. G01N 33/57496 |
| 2014/0302050 | A1 * | 10/2014 | Kenny ................... C07K 16/22 424/139.1 |
| 2015/0232572 | A1 | 8/2015 | Noel et al. |
| 2018/0327488 | A1 | 11/2018 | Yarden et al. |
| 2018/0327803 | A1 | 11/2018 | Kumada et al. |

FOREIGN PATENT DOCUMENTS

| | | | |
|---|---|---|---|
| WO | WO 91/17271 | A1 | 11/1991 |
| WO | WO 92/01047 | A1 | 1/1992 |
| WO | WO 93/12227 | A1 | 6/1993 |
| WO | WO 99/58572 | A1 | 11/1999 |
| WO | WO 01/27160 | A1 | 4/2001 |
| WO | WO 0200729 | A3 | 1/2002 |
| WO | WO 02/43478 | A3 | 6/2002 |
| WO | WO 2017/161206 | A1 | 9/2017 |

OTHER PUBLICATIONS

Lloyd, C et. al. "Modeling the human immune response: performance of a 10" human antibody repertoire against a broad panel of therapeutically relevant antigens", 2009, Protein Engineering, Design, & Selection, 22(3), 159-168. (Year: 2009).*

Edwards, BM et. al. "The Remarkable Flexibility of the Human Antibody Repertoire; Isolation of Over One Thousand Different Antibodies to a Single Protein, BLyS", 2003, J. Mol. Biol., 334, 103-118. (Year: 2003).*

Ducry, Laurent and Stump, Bernhard. "Antibody-Drug Conjugates: Linking Cytotoxic Payloads to Monoclonal Antibodies", 2010, Bioconjugate Chem., 21(1), 5-13. (Year: 2010).*

Ravetch, Jeffrey V and Kinet, Jean-Pierre. "Fc Receptors", 1991, Annu. Rev. Immunol., 9, 457-492. (Year: 1991).*

Schroeder, Harry W and Cavacini, Lisa. "Structure and function of immunoglobulins", 2010, J. Allergy Clin. Immunol., 125(2), S41-S52. (Year: 2010).*

Tiller, Kathryn E and Tessier, Peter M. "Advances in Antibody Design", 2015, Annu. Rev. Biomed. Eng., 17, 191-216. (Year: 2015).*

Winkler et al. (2000, The Journal of Immunology, 265:4505-4514) (Year: 2000).*

International Search Report and Written Opinion dated Nov. 7, 2022, for PCT Application No. PCT/US2022/032834.

Akaiwa, M, Dugal-Tessier, J, Mendelsohn, BA. Antibody-drug conjugate payloads; study of Auristatin derivatives. *Chem Pharm Bull* (Tokyo) 2020; 68: 201-11.

Altschul et al., Basic local alignment search tool, *J. Mol. Biol.* 215:403-410 (1990).

Barroso-Sousa, R, Tolaney, SM. Clinical development of new antibody-drug conjugates in breast cancer: to infinity and beyond. *BioDrugs* 2021; 35: 159-74.

Boder, E. T., et al., Yeast surface display for screening combinatorial polypeptide libraries, *Nat. Biotechnol.* 15(6):553-7 (1997).

Boerner et al., Production of antigen-specific human monoclonal antibodies from in vitro-primed human splenocytes, J. Immunol., 147(1):86-95 (1991).

Bostwick DG, Qian J, Maihle NJ. Amphiregulin expression in prostatic intraepithelial neoplasia and adenocarcinoma: a study of 93 cases. Prostate 2004; 58(2): 164-8.

Brown et al. *Cancer Res.* 47: 3577-3583 (1987).

Busser, B, Sancey, L, Brambilla, E et al. The multiple roles of amphiregulin in human cancer. *Biochimica et Biophysica Acta* 2011; 1816: 119-31.

Byers, B. S. et al., Rationale for clinical use of immunotoxins in cancer and autoimmune disease, *Seminars Cell Biol* 2:59-70 (1991).

Campana et al., Double and triple staining methods for studying the proliferative activity of human B and T lymphoid cells, *J. Immunol. Meth.* 107:79 (1988).

Chen, J., Effects of ectopic overexpression of p21(WAF1/CIP1) on aneuploidy and the malignant phenotype of human brain tumor cells, *Oncogene* 13:1395-403 (1996).

Ciarloni, L, Mallepell, S, Brisken, C. Amphiregulin is an essential mediator of estrogen receptor alpha function in mammary gland development. *Proc Natl Acad Sci U S A* 2007; 104: 5455-60.

Clarke, R., Tyson, J.J. and Dixon, J.M. (2015) Endocrine resistance in breast cancer—an overview and update. *Mol Cell Endocrinol*, 418 Pt 3, 220-234.

Coia G, et al., Panning and selection of proteins using ribosome display, *J. Immunol. Methods* 1: 254 (1-2): 191-7 (2001).

Daugherty et al., Polymerase chain reaction facilitates the cloning, CDR-grafting, and rapid expression of a murine monoclonal antibody directed against the CD18 component of leukocyte integrins, *Nucl. Acids Res.* 19: 2471-2476 (1991).

David et al., Protein iodination with solid state lactoperoxidase, *Biochemistry*, 13:1014 (1974).

Evans, 2007, *Aust J Chem* 60:384-95.

Fan, M, Yan, PS, Hartman-Frey, C et al. Diverse gene expression and DNA methylation profiles correlate with differential adaptation of breast cancer cells to the antiestrogens tamoxifen and fulvestrant. *Cancer Res* 2006; 66: 11954-66.

Fanger, M. W. et al., Bispecific antibodies and targeted cellular cytotoxicity, *Immunol Today* 12:51-54 (1991).

Gillies et al., High-level expression of chimeric antibodies using adapted cDNA variable region cassettes, *J. Immunol. Methods* 125:191-202 (1989).

Gschwind, A, Hart, S, Fischer, OM et al. TACE cleavage of proamphiregulin regulates GPCR-induced proliferation and motility of cancer cells. *Embo J* 2003; 22: 2411-21.

Hamblett, KJ, Senter, PD, Chace, DF et al. Effects of drug loading on the antitumor activity of a monoclonal antibody drug conjugate. *Clin Cancer Res* 2004; 10: 7063-70.

Hanes J. et al., Picomolar affinity antibodies from a fully synthetic naive library selected and evolved by ribosome display *Nat. Biotechnol.*: 18(12): 1287-92 (2000).

Hanes, J, Jermutus, L, et al. Ribosome display efficiently selects and evolves high-affinity antibodies in vitro from immune libraries, *Proc. Natl. Acad. Sci. U.S.A.* 95(24): 14130-5 (1998).

Hanes, J, and Plückthun, A. In vitro selection and evolution of functional proteins by using ribosome display, *Proc. Natl. Acad. Sci. U.S.A.* 94(10): 4937-42 (1997).

Harris, Production of humanized monoclonal antibodies for in vivo imaging and therapy, *Biochem. Soc. Transactions* 23:1035-1038 (1995).

Hoogenboom and Winter, By-passing immunisation. Human antibodies from synthetic repertoires of germline VH gene segments rearranged in vitro, J. Mol. Biol., 227:381 (1991).

Hoshino et al., S-phase fraction of human brain tumors in situ measured by uptake of bromodeoxyuridine, *Int. J. Cancer* 38, 369 (1986).

Hunter et al., *Nature*, 144:945 (1962).

Hurle and Gross, Protein engineering techniques for antibody humanization, *Curr. Op. Biotech.* 5:428-433 (1994).

Huse et al., Generation of a Large Combinatorial Library of the Immunoglobulin Repertoire in Phage Lambda, *Science* 246:1275-1281 (1989).

Jeoung, J., Effects of tumor necrosis factor-alpha on antimitogenicity and cell cycle-related proteins in MCF-7 cells, *J. Biol. Chem.* 270:18367-73 (1995).

Jones et al., Replacing the complementarity-determining regions in a human antibody with those from a mouse, *Nature* 321:522-525 (1986).

Kenny, PA, Bissell, MJ. Targeting TACE-dependent EGFR ligand shedding in breast cancer. *J Clin Invest* 2007; 117: 337-45.

Khambata-Ford S, Garrett CR, Meropol NJ, et al. Expression of epiregulin and amphiregulin and K-ras mutation status predict

(56) References Cited

OTHER PUBLICATIONS disease control in metastatic colorectal cancer patients treated with cetuximab. Journal of Clinical Oncology 2007; 25(22): 3230-7.

Kohler and Milstein, Continuous cultures of fused cells secreting antibody of predefined specificity, Nature 256: 495-7 (1975).

Kohler and Milstein, Derivation of specific antibody-producing tissue culture and tumor lines by cell fusion, *Eur. J. Immunol.* 6: 511 (1976).

Kolb et al., 2004, *Angew Chem Int Ed* 40:3004-31.

Levano, KS, Kenny, PA. Clarification of the C-terminal proteolytic processing site of human Amphiregulin. *FEBS Letters* 2012; 586: 3500-2.

Li et al., Human antibodies for immunotherapy development generated via a human B cell hybridoma technology, *Proc. Natl. Acad. Sci. USA*, 103:3557-3562 (2006).

Lobuglio et al. Mouse/human chimeric monoclonal antibody in man: kinetics and immune response, *Proc. Nat. Acad. Sci. USA* 86: 4220-4224 (1989).

Lofgren KA, Sreekumar S, Jenkins EC, Jr., Ernzen KJ, Kenny PA. Anti-tumor efficacy of an MMAE-conjugated antibody targeting cell surface TACE/ADAM17-cleaved Amphiregulin in breast cancer. Antib Ther 2021; 4(4): 252-61.

Lyon, RP, Bovee, TD, Doronina, SO et al. Reducing hydrophobicity of homogeneous antibody-drug conjugates improves pharmacokinetics and therapeutic index. *Nat Biotechnol* 2015; 33: 733-5.

Marks et al., By-passing immunization: Human antibodies from V-gene libraries displayed on phage, J. Mol. Biol., 222:581 (1991).

McBryan, J, Howlin, J, Kenny, PA et al. ERalpha-CITED1 co-regulated genes expressed during pubertal mammary gland development: implications for breast cancer prognosis. *Oncogene* 2007; 26: 6406-19.

Meier DR, Girtman MA, Lofgren KA, Kenny PA. Amphiregulin deletion strongly attenuates the development of estrogen receptor-positive tumors in p53 mutant mice. Breast Cancer Res Treat 2020; 179(3): 653-60.

Morrison, Transfectomas provide novel chimeric antibodies, *Science* 229:1202-1207 (1985).

Nygren, J. Conjugation of horseradish peroxidase to Fab fragments with different homobifunctional and heterobifunctional cross-linking reagents. A comparative study, *Histochem. and Cytochem.*, 30:407 (1982).

Oestberg et al., Human X (mouse X human) hybridomas stably producing human antibodies, *Hybridoma* 2:361-367 (1983).

Oi et al., *BioTechniques* 4:214-221 (1986).

Pain et al., Preparation of protein A-peroxidase monoconjugate using a heterobifunctional reagent, and its use in enzyme immunoassays, *J. Immunol. Meth.*, 40:219 (1981).

Peters, C, Brown, S. Antibody-drug conjugates as novel anti-cancer chemotherapeutics. *Biosci Rep* 2015; 35: e00225.

Peterson, EA, Jenkins, EC, Lofgren, KA et al. Amphiregulin Is a critical downstream effector of estrogen signaling in ERalpha-positive breast cancer. *Cancer Res* 2015; 75: 4830-8.

Presta, *Curr. Op. Struct. Biol.* 2:593-596 (1992).

Riechmann et al., Reshaping human antibodies for therapy, *Nature* 332:323-329 (1988).

Schmucker, H, Blanding, WM, Mook, JM et al. Amphiregulin regulates proliferation and migration of HER2-positive breast cancer cells. *Cell Oncol (Dordr)* 2018; 41: 159-68.

Schrama, D, Reisfeld, RA, Becker, JC. Antibody targeted drugs as cancer therapeutics. *Nat Rev Drug Discov* 2006; 5: 147-59.

Shaw et al. Characterization of a mouse/human chimeric monoclonal antibody (17-1A) to a colon cancer tumor-associated antigen, *J. Immunol.* 138: 4534-4538 (1987).

Shih et al., Site-specific linkage of methotrexate to monoclonal antibodies using an intermediate carrier, *Int. J Cancer* 41: 832 (1988).

Shih et al., A fluorouridine-anti-CEA immunoconjugate is therapeutically effective in a human colonic cancer xenograft model, *Int. J. Cancer* 46: 1101 (1990).

Sun, X, Ponte, JF, Yoder, NC et al. Effects of drug-antibody ratio on pharmacokinetics, biodistribution, efficacy, and tolerability of antibody-maytansinoid conjugates. *Bioconjug Chem* 2017; 28: 1371-81.

Sun, MM, Beam, KS, Cerveny, CG et al. Reduction-alkylation strategies for the modification of specific monoclonal antibody disulfides. *Bioconjug Chem* 2005; 16: 1282-90.

Tomizuka et al. Double trans-chromosomic mice: maintenance of two individual human chromosome fragments containing Ig heavy and kappa loci and expression of fully human antibodies, (2000) *Proc. Natl. Acad. Sci. USA* 97:722-727.

Tornoe et al., Peptidotriazoles on solid phase: [1,2,3]-triazoles by regiospecific copper(i)-catalyzed 1,3-dipolar cycloadditions of terminal alkynes to azides, 2002, *J Organic Chem* 67:3057-64.

Van Dijk and van de Winkel, Human antibodies as next generation therapeutics, Curr. Opin. Pharmacol., 5: 368-74 (2001).

Vaswani and Hamilton, Humanized antibodies as potential therapeutic drugs, Ann. Allergy, *Asthma & Immunol.* 1:105-115 (1998).

Vaughan et al., Human Antibodies with Subnanomolar Affinities Isolated from a Large Non-immunized Phage Display Library, *Nature Biotech.* 14:309-314 (1996).

Verhoeyen et al. Reshaping human antibodies: grafting an antilysozyme activity, *Science* 239: 1534-1536 (1988).

Voytik-Harbin SL et al., Application and evaluation of the alamarBlue assay for cell growth and survival of fibroblasts, *In Vitro Cell Dev Biol Anim* 34:239-46 (1998).

Waks, AG, Winer, EP. Breast cancer treatment: a review. *JAMA* 2019; 321: 288-300.

Wang B, Yong H, Zhu H, et al. Abnormal amphiregulin expression correlates with gastric cancer prognosis. Oncotarget 2016; 7(47): 76684-92.

Wang L, Wu H, Wang L, et al. Expression of amphiregulin predicts poor outcome in patients with pancreatic ductal adenocarcinoma. Diagn Pathol 2016; 11(1): 60.

Willmarth, NE, Ethier, SP. Autocrine and juxtacrine effects of amphiregulin on the proliferative, invasive, and migratory properties of normal and neoplastic human mammary epithelial cells. *J Biol Chem* 2006; 281: 37728-37.

Winter et al. Man-made antibodies, *Nature* 349: 293-299 (1991).

Yeung, et al., Quantitative screening of yeast surface-displayed polypeptide libraries by magnetic bead capture, *Biotechnol. Prog.* 18(2):212-20 (2002).

Yonesaka K, Zejnullahu K, Lindeman N, et al. Autocrine production of amphiregulin predicts sensitivity to both gefitinib and cetuximab in EGFR wild-type cancers. Clin Cancer Res 2008; 14(21): 6963-73.

Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells, *Int. J. Cancer* 56: 244 (1994).

\* cited by examiner

SEQUENCE LISTING

```
<160> NUMBER OF SEQ ID NOS: 9

<210> SEQ ID NO 1
<211> LENGTH: 252
<212> TYPE: PRT
<213> ORGANISM: Homo sapiens

<400> SEQUENCE: 1

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
    130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175
```

```
Phe Gly Glu Arg Cys Gly Glu Lys Ser Met Lys Thr His Ser Met Ile
                180                 185                 190

Asp Ser Ser Leu Ser Lys Ile Ala Leu Ala Ala Ile Ala Ala Phe Met
            195                 200                 205

Ser Ala Val Ile Leu Thr Ala Val Ala Val Ile Thr Val Gln Leu Arg
    210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250

<210> SEQ ID NO 2
<211> LENGTH: 12
<212> TYPE: PRT
<213> ORGANISM: Homo sapiens

<400> SEQUENCE: 2

Thr His Ser Met Ile Asp Ser Ser Leu Ser Lys Ile
1               5                   10

<210> SEQ ID NO 3
<211> LENGTH: 114
<212> TYPE: PRT
<213> ORGANISM: Artificial Sequence
<220> FEATURE:
<223> OTHER INFORMATION: 1A3 antibody, Heavy chain

<400> SEQUENCE: 3

Gln Ser Val Lys Glu Ser Glu Gly Arg Leu Val Thr Pro Gly Thr Pro
1               5                   10                  15

Leu Arg Leu Thr Cys Thr Val Ala Gly Tyr Ser Leu Ser Arg Tyr His
            20                  25                  30

Met Cys Trp Val Arg Gln Ala Pro Gly Lys Gly Leu Glu Trp Ile Gly
        35                  40                  45

Met Ile Gly Gly Ser Gly Arg Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ser Thr Val Tyr
                85                  90                  95

Thr Asp Ser Asp Gly Asp Phe Trp Gly Pro Gly Thr Leu Val Thr Val
            100                 105                 110

Ser Ser

<210> SEQ ID NO 4
<211> LENGTH: 113
<212> TYPE: PRT
<213> ORGANISM: Artificial Sequence
<220> FEATURE:
<223> OTHER INFORMATION: 1A3 antibody, Light chain

<400> SEQUENCE: 4

Ala Glu Leu Asp Met Thr Gln Thr Pro Ser Ser Lys Ser Val Pro Val
1               5                   10                  15

Gly Gly Thr Val Thr Ile Asn Cys Gln Ala Ser Glu Ser Val Tyr Ser
            20                  25                  30

Asn Asp Arg Leu Ala Trp Phe Gln Gln Lys Pro Gly Gln Pro Pro Lys
        35                  40                  45
```

```
Leu Leu Ile Tyr Tyr Ala Ser Thr Leu Ala Ser Gly Val Pro Ser Arg
 50                  55                  60
Phe Lys Gly Ser Gly Ser Gly Thr Gln Phe Thr Leu Thr Ile Ser Asp
 65                  70                  75                  80
Leu Glu Cys Ala Asp Ala Ala Thr Tyr Tyr Cys Gln Ser Cys Tyr Asp
                 85                  90                  95
Met Ser Ser Tyr Gly Val Ala Phe Gly Gly Gly Thr Glu Leu Glu Ile
                100                 105                 110
Leu
```

<210> SEQ ID NO 5
<211> LENGTH: 119
<212> TYPE: PRT
<213> ORGANISM: Artificial Sequence
<220> FEATURE:
<223> OTHER INFORMATION: 3A3 antibody, Heavy chain

<400> SEQUENCE: 5

```
Gln Gln Gln Leu Val Glu Ser Gly Gly Arg Leu Val Thr Pro Gly Thr
 1               5                  10                  15
Pro Leu Thr Leu Thr Tyr Thr Val Ser Gly Phe Ser Leu Ser Asp Tyr
                 20                  25                  30
His Met Ser Trp Val Arg Gln Ala Pro Gly Lys Gly Leu Gln Trp Ile
             35                  40                  45
Ala Thr Ile Ser Asn Arg Gly Asn Thr Tyr Tyr Ala Ser Trp Ala Lys
 50                  55                  60
Gly Arg Phe Thr Ile Ser Lys Thr Ser Thr Thr Val Asp Leu Lys Ile
 65                  70                  75                  80
Thr Ser Pro Thr Thr Glu Asp Thr Ala Thr Tyr Phe Cys Ala Arg Asp
                 85                  90                  95
Asn Val His Gly Asp Gly Val Leu Val Phe Tyr Leu Trp Gly Pro Gly
                100                 105                 110
Thr Leu Val Thr Val Ser Ser
            115
```

<210> SEQ ID NO 6
<211> LENGTH: 109
<212> TYPE: PRT
<213> ORGANISM: Artificial Sequence
<220> FEATURE:
<223> OTHER INFORMATION: 3A3 antibody, Light chain

<400> SEQUENCE: 6

```
Ala Glu Leu Val Met Thr Gln Thr Pro Ala Ser Val Ser Glu Pro Val
 1               5                  10                  15
Gly Gly Thr Val Thr Ile Lys Cys Gln Ala Ser Gln Ser Ile Gly Thr
                 20                  25                  30
Asn Leu Ala Trp Tyr Gln Gln Lys Pro Gly Gln Pro Pro Lys Arg Leu
             35                  40                  45
Ile Tyr Lys Ala Ser Thr Leu Ala Ser Gly Val Ser Ser Arg Phe Lys
 50                  55                  60
Gly Ser Gly Ser Gly Thr Glu Phe Thr Leu Thr Ile Ser Asp Leu Glu
 65                  70                  75                  80
Cys Ala Asp Ala Ala Thr Tyr Tyr Cys Gln Gly Tyr Tyr Ser Gly Asp
                 85                  90                  95
Ser Asn Ala Phe Gly Gly Gly Thr Glu Val Val Val Lys
                100                 105
```

<210> SEQ ID NO 7
<211> LENGTH: 117
<212> TYPE: PRT
<213> ORGANISM: Artificial Sequence
<220> FEATURE:
<223> OTHER INFORMATION: 3E4 antibody, Heavy chain

<400> SEQUENCE: 7

```
Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Asp Tyr Trp
            20                  25                  30

Met Ser Trp Val Arg Gln Ala Pro Gly Lys Gly Leu Glu Trp Ile Gly
        35                  40                  45

Ile Ala Gly Tyr Ser Asp Asn Thr Tyr Tyr Ala Ser Arg Ala Lys Gly
    50                  55                  60

Arg Phe Thr Ile Ser Lys Thr Ser Thr Thr Val Val Leu Lys Ile Thr
65                  70                  75                  80

Arg Pro Thr Thr Glu Asp Thr Ala Thr Tyr Phe Cys Val Arg Asp Leu
                85                  90                  95

Tyr Gly Val Tyr Ser Ser Gly Thr Thr Leu Trp Gly Pro Gly Thr Leu
            100                 105                 110

Val Thr Val Ser Ser
        115
```

<210> SEQ ID NO 8
<211> LENGTH: 111
<212> TYPE: PRT
<213> ORGANISM: Artificial Sequence
<220> FEATURE:
<223> OTHER INFORMATION: 3E4 antibody, Light chain

<400> SEQUENCE: 8

```
Ala Glu Leu Val Met Thr Gln Thr Pro Ser Pro Val Ser Ala Ala Val
1               5                   10                  15

Gly Gly Thr Val Thr Ile Ser Cys Gln Ser Ser Gln Ser Val Tyr Asn
            20                  25                  30

Asn Asn Arg Leu Ala Trp Phe Gln Gln Lys Pro Gly Gln Pro Pro Lys
        35                  40                  45

Leu Leu Ile Tyr Tyr Ala Ser Thr Leu Ala Ser Gly Val Ser Ser Arg
    50                  55                  60

Phe Lys Gly Ser Gly Ser Gly Thr Gln Phe Thr Leu Ile Ile Ser Asp
65                  70                  75                  80

Val Val Cys Asp Asp Ala Ala Thr Tyr Tyr Cys Gln Gly Tyr Tyr Ser
                85                  90                  95

Gly Gly Ile Thr Gly Phe Gly Gly Thr Glu Val Val Val Lys
            100                 105                 110
```

<210> SEQ ID NO 9
<211> LENGTH: 17
<212> TYPE: PRT
<213> ORGANISM: Artificial Sequence
<220> FEATURE:
<223> OTHER INFORMATION: Sequence representing uncleaved AREG, used for
      antibody identification

```
<400> SEQUENCE: 9

Ser Met Lys Thr His Ser Met Ile Asp Ser Ser Leu Ser Lys Ile Ala
1               5                   10                  15
Cys
```

ANTIBODIES TARGETING AN AMPHIREGULIN-DERIVED CELL SURFACE NEO-EPITOPE

FEDERAL FUNDING STATEMENT

This invention was made with government support under W81XWH-14-1-0294 awarded by the U.S. Department of Defense. The government has certain rights in the invention.

BACKGROUND

Breast cancer is the second most frequently diagnosed cancer in women and is classified into clinical subtypes by the expression status of the estrogen and progesterone receptors (ER, PR) and the presence or absence of HER2 amplification. ER+ tumors comprise approximately 70% of all breast tumors.[1] Patients with ER+ disease receive treatment with endocrine targeting therapies such as tamoxifen and aromatase inhibitors with significant initial success; however, the emergence of ER independent or endocrine therapy-resistant disease is problematic.[2] As such, the development of alternative therapeutics for endocrine-insensitive disease is of critical importance.

Amphiregulin (AREG) is a transmembrane protein which, following TACE/ADAM17-dependent cleavage,[3] releases a soluble EGFR ligand domain which promotes proliferation of normal and malignant cells. The inhibition of ADAM17 with protease inhibitors prevents AREG shedding and effectively interrupts this EGFR-activating signal.[4] AREG is transcriptionally regulated by estrogen during normal mammary gland development[5] and in breast cancer[6] and is a required effector for estrogen's proliferation signal in both settings.[6-7] High AREG expression levels are correlated to ER-alpha expression in breast cancer[4,6] and, when overexpressed experimentally, AREG promotes EGF signaling self-sufficiency.[8] While the primary focus has been on the role of AREG in breast cancer, AREG is noted to be expressed in several other cancer types.[9] Thus, the potential utility of a therapeutic antibody and antibody-drug conjugates (ADCs) extends to other malignancies.

ADCs consist of an antibody against a specifically targeted epitope that is used to deliver locally high concentrations of a toxic payload to a cell of interest. The payload can be toxins or chemicals that induce DNA damage, disrupt cytoskeletal integrity or interfere with the process of DNA replication. The value of ADCs is the specific delivery to a tumor of drugs that may be too toxic for patients or have complicating side effects if given at a dose high enough for tumor eradication. At least 34 unique ADCs are in various stages of clinical trials in the USA for treating solid tumors, with only three being Food and Drug Administration approved for clinical use in breast cancer at the time of publication: two targeting HER2 (trastuzumab emtansine, trastuzumab deruxtecan) and sacituzumab govitecan, which targets Trop-2 in metastatic triple-negative breast cancer patients.[10] ADC development in breast cancer has mostly been directed toward HER2+ disease, with relatively little attention given to ER+ disease due to a paucity of targets. Thus, the identification of novel epitopes to be targeted in the context of ER+ disease is of value. Given the strong requirement for AREG expression and proteolytic cleavage in ER+ breast cancer,[6] the residual cell-bound stalk resulting from AREG cleavage could serve as a neo-epitope for therapeutic antibody and ADC development (FIG. 1D).

SUMMARY

The present disclosure addresses the need for improved diagnostic methods and treatment protocols for ER+ tumors. Disclosed herein is an epitope on ER+ tumor cells. Also disclosed herein are novel antibodies that recognize the epitope and are thus useful to diagnose the presence of neoplasms and to inhibit their growth.

Disclosed herein are isolated antibodies, or isolated fragments of antibodies, which selectively bind to a membrane-associated extracellular portion of a cleaved amphiregulin precursor protein (e.g., an amino acid having at least 60% sequence identity to SEQ ID NO:2).

The antibodies disclosed herein include human, humanized, and chimeric antibodies. The antibodies may be whole antibodies or antibody fragments. In preferred versions, the antibody fragments include Fab, Fab', F(ab')$_2$, Fd, Fv, complementarity determining region (CDR), and/or single chain antibodies (scFv). The antibodies may be monoclonal antibodies or polyclonal antibodies. Monoclonal antibodies are preferred.

The antibodies provided herein include antibodies with 60% or greater sequence identity to the amino acid sequences of the $V_H$ and $V_L$ regions disclosed in SEQ ID NOs: 3-8). In one preferred version, the antibody comprises a $V_H$ region amino acid sequence having at least 60% sequence identity to a sequence selected from SEQ ID NOs: 3, 5, and 7, and/or a $V_L$ region amino acid sequence selected from SEQ ID NOs: 4, 6, and 8. In one embodiment, the antibody comprises an amino acid sequence having at least 60% sequence identity to SEQ ID NO: 3 and/or SEQ ID NO: 4, which correspond to the $V_H$ and $V_L$ regions of the 1A3 antibody, respectively. In another embodiment, the antibody comprises a polypeptide having at least 60% sequence identity to SEQ ID NO:5 and/or SEQ ID NO:6, which correspond to the $V_H$ and $V_L$ regions of the 3A3 antibody, respectively. In another version, the antibody comprises SEQ ID NO:7 and/or SEQ ID NO:8, or a sequence having at least 60% sequence identity thereto, which correspond to the $V_H$ and $V_L$, regions of the 3E4 antibody, respectively.

The antibody may be conjugated to an effector moiety or component. The effector moiety may be a label (e.g., a fluorescent label, an effector domain, e.g., MicA) or can be a cytotoxic agent (e.g., a radioisotope or a cytotoxic chemical). In one preferred version, the antibody is conjugated to a cytotoxic agent, such as auristatin (e.g., monomethyl auristatin E (MMAE)).

Also disclosed herein are pharmaceutical compositions comprising the isolated antibodies or the isolated fragments of the antibodies described herein. Preferably, the antibody selectively binds the cleaved amphiregulin, and more preferably it is conjugated to an effector moiety, such as a cytotoxic agent (e.g., auristatin). The pharmaceutical composition inhibits proliferation of tumor cells in vivo, wherein the cells are amphiregulin-expressing tumor cells. The pharmaceutical composition may comprise a pharmaceutically acceptable carrier or excipient. In one version, the pharmaceutical composiiGon comprises an anti-cleaved amphireguin andbodiy comprising a heavy chain variable region (Vrr) having an amino acid sequence selected from SEQ ID NOs: 3, 5, and 7 and/or a light chain variable region ($V_L$) having an amino acid sequence selected from SEQ ID NOs: 4, 6 and 8, or a polypeptide having at least 60% sequence identity thereto.

In some embodiments of the pharmaceutica composition, the anti-cleaved amphiregulin antibody is conjugated to an effector moiety or component. The effector component may be a label (e.g. a fluorescent label) or can be cytotoxic agent (e.g., a radioisotope or a cytotoxic chemical moiety). A variety of cytotoxic agents may be conjugated to the anti-cleaved anphireguin antibody disclosed herein, including:

diphtheria A chain, exotoxin A chain, ricin A chain, abrin A chain, curcin, crotin, phenorycin, neomycin, doxorubicin, Rhenium-188, naytaFsinoids, deruxtecan, and auristatin. The anti-cleaved amphiregulin antbodies in the pharmaceutical compositions may be whole antibodies or may be antibody fragments (e.g., Fab, Fab', F(ab')$_2$, Fd, Fv, complementarity determining region (CDR), and single chain antibodies (scFv)). As noted above, the pharmaceutical composition may include a human, humanized, or chireric anti-cleaved amphiregulin anibody.

Also disclosed herein are methods of inhibiting proliferation of a cancer cell or other neoplastic cell type. The method comprises contacting the cell with an anti-cleaved amphiregulin antibody disclosed herein conjugated to an effector moiety, such as a cytotoxic agent. The anti-cleaved amphiregulin antibody is dimensioned and configured to selectively bind to a membrane-associated extracellular portion of a cleaved amphiregulin precursor protein (e.g., SEQ ID NO:2). The cancer-associated cell is typically in a mammalian subject, including humans. The subject may be diagnosed with a cancerous condition or may simply be suspected of having cancer.

Additionally disclosed herein is a method of inhibiting neoplastic cell growth in a subject in need of such a treatment by administering to the subject a pharmaceutically effective amount of anti-cleaved amphiregulin antibodies comprising a heavy chain variable region ($V_H$) having an amino acid sequence selected from SEQ ID NOs: 3, 5, and 7 and/or a light chain variable region ($V_L$) having an amino acid sequence selected from SEQ ID NOs: 4, 6 and 8, (or a protein having at least 60% sequence identity thereto) and a therapeutically effective amount of a cytotoxic agent to a patient wherein the antibodies and cytotoxic agent may be administered simultaneously, or either one before the other. In another alternative, the cytotoxic agent is conjugated to the antibody and thereby added simultaneously.

Also disclosed herein are diagnostic tests and immunoassays employing the various anti-amphiregulin antibodies disclosed herein. In preferred embodiments, these methods involve detecting a cancer cell in a biologic sample from a patient by contacting the biological sample with an anti-amphiregulin antibody as disclosed herein. In some embodiments, the antibody is conjugated to a label such as fluorescent label, radioisotope or an enzyme such as horseradish peroxidase.

Further disclosed herein is a method of diagnosing a cancer in a mammal. comprising contacting an anti-amphiregulin antibody with a test sample obtained from the mammal and detecting the formation of a complex between the antibody and a polypeptide of the test sample. At least a portion of the antibody selectively binds to a membrane-associated extracellular portion of a cleaved amphiregulin precursor protein (e.g., SEQ ID NO:2) In preferred embodiments of this method, the test sample is obtained from an individual suspected of having cancer.

The objects and advantages of the disclosure will appear more fully from the following detailed description of the preferred embodiment of the disclosure made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: Schematic representation of the AREG cleavage and EGFR activation process, one consequence of which is the internalization of the small transmembrane fragment that remains cell-associated after TACE/ADAM17-mediated cleavage. FIG. 1B: Schematic representation of phage panning strategy using a peptide representing the cleaved AREG neo-epitope adhered to the well and a peptide representing the non-cleaved AREG region in the liquid phase. FIG. 1C: ELISA analysis of the three lead candidate rabbit IgG molecules demonstrating their relative affinities for peptides representing the full length and cleaved/truncated AREG FIG. 1D. Schematics depicting that conjugation of antibody with a chemotherapeutic yield an agent that selectively targets high doses of therapy to cancer cells shedding large quantities of amphiregulin.

FIG. 2A: MCF-7 cells labeled with Hoechst 33342 (blue) and Lysotracker (green) were treated with 1A3-pHrodo (red) and monitored with live-cell imaging (40×). Note the appearance of yellow in the merged image indicating trafficking of the antibody to lysosomes. FIG. 2B: MCF-7 cells were pretreated with TAPI-2 overnight to prevent AREG cleavage, labeled with Hoechst and Lysotracker, and imaged as in FIG. 2A (40×). Merged images are shown. Comparative absence of red and yellow signal in the TAPI-2 treated cells shows failure to internalize 1A3-pHrodo.

FIG. 3A: SDS-PAGE of TRF, and TRF conjugated AREG peptides including the cleavage site (FL-AREG) or a mimic of cleaved AREG (Trunc AREG). Samples were blotted with 1A3 or 1A3-MMAE antibody. FIG. 3B: ELISA comparing binding of 1A3 and 1A3-MMAE to a cleaved AREG peptide. FIG. 3C: HIC-HPLC profile of unconjugated 1A3 antibody (blue) and the 1A3-MMAE conjugate (red).

FIG. 4C: Clonogenic growth of MCF-7 or MCF-7F cells after exposure to 1A3-MMAE and replating. FIG. 4D: The quantification of clonogenic growth assays in FIG. 4C. (FIG. 4E). Tubulin staining of MCF-7 cells after 48 h treatment with MMAE, 1A3, 1A3-MMAE (40× magnification).

FIG. 5A: Caliper measurements of MCF-7 (left) and MCF7-F (right) orthotopic xenografts after treatment initiation. Each curve represents an individual tumor. Treatment times for the six treatments are indicated. FIG. 5B: Representative in vivo luminescence of MCF7 (left panels) and MCF7-F (right panels) xenograft tumors from FIG. 5A during the course of treatment. A red X indicates an animal euthanized due to tumor burden. The heatmap indicates the intensity range of the luminescence signal. FIG. 5C: Waterfall plot showing maximum response of the MCF7 (left) and MCF7-F (right) xenograft tumors to the treatment course. The Y-axis is truncated at 300%.

FIG. 6A: Representative examples of immunohistochemical staining intensities observed (×20 magnification) in a human breast tissue array using an antibody to FL AREG (top row), or 1A3 targeting cleaved AREG (bottom row). FIG. 6B: Cross-comparison of intensity scores for FL and cleaved AREG (1A3) from the breast tissue array.

FIG. 7A: Representative examples of immunohistochemical staining for cleaved Amphiregulin at each of the three detected staining intensities. Images from the same cores were captured at 10× and 40× magnification. FIG. 7B: Quantification of cleaved Amphiregulin intensity scores in 380 tumors from ten different cancer types.

FIG. 8A: Cross-comparison of intensity scores for both cleaved (Y-axis) and total (X-axis) Amphiregulin in 380 tumors. Data point size is proportional to the number of cases in each pairwise group and the number of cases in each group is indicated. FIG. 8B: Representative examples of tissue cores in which both total and cleaved Amphiregulin both had low, medium or high immunostaining intensity.

FIG. 9A=breast cancer, FIG. 9B=prostate cancer, FIG. 9C=liver cancer, FIG. 9D=lung cancer, FIG. 9E=colon cancer, FIG. 9F=pancreatic cancer, FIG. 9G=stomach cancer, FIG. 9H=uterine cancer, FIG. 9I=ovarian cancer. FIG. 9J=oral cavity cancer.

DETAILED DESCRIPTION

Figure 1A:
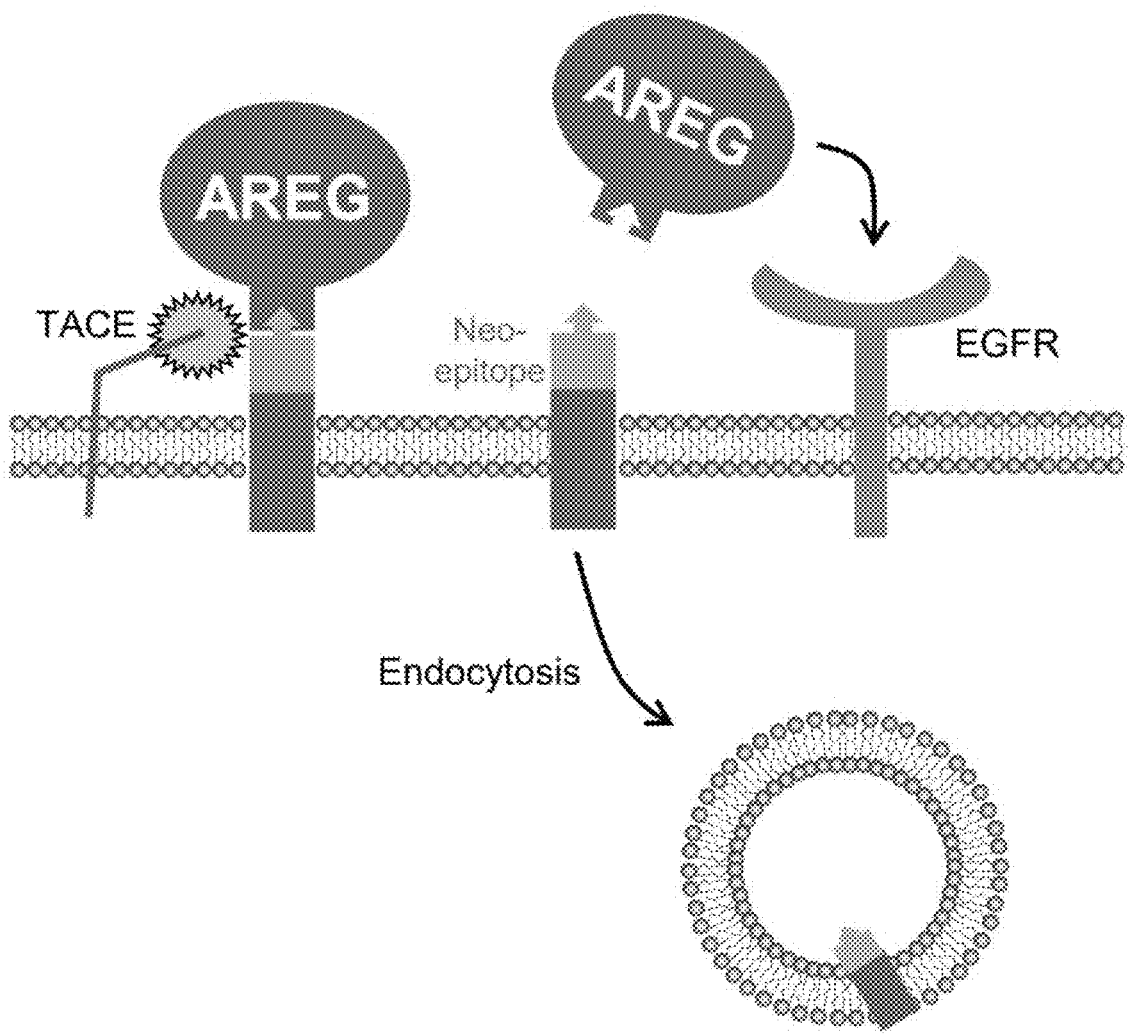
FIGS. 1A-1C. Isolation of antibodies that selectively recognize a peptide representing cleaved AREG.

As used herein, "aintibody" includes reference to an immunoglobulin molecule immunologically reactive with a particular antigen and includes both polyclonal and monoclonal antibodies. An antibody immunologically reactive with a particular antigen can be generated by recombinant methods such as selection of libraries of recombinant antibodies in phage or similar vectors, see, e.g., Huse et al., Science 246:1275-1281(1989); Ward et al., Nature 341:544-546 (1989); and Vaughan et al., Nature Biotech. 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three-dimensional space.

References to "$V_H$" or a "$V_H$" refer to the variable region of an immunoglobulin heavy chain of an antibody, including the heavy chain of an Fv, scFv, or Fab. References to "$V_L$" or a "$V_L$" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

As used herein, term "antibody" refers to an intact antibody, i.e., with complete Fc and Fv regions. "Fragment" refers to any portion of an antibody, or portions of an antibody linked together, such as a single-chain antibody (scFv), which is less than the whole. antibody, but which is an antigen-binding portion, and which competes with the intact antibody of which it is a fragment for specific binding. As such a fragment can be prepared, for example, by cleaving an intact antibody or by recombinant means, See generally, Fundamental Immunology, Ch. 7 (Paul, W., ed., 2nd ed. Raven Press, N.Y. (1989)). Antigen-binding fragments may be produced by recombinant DNA techniques or by enzymatic or, for example, chemical cleavage of intact antibodies or by molecular biology techniques. In some embodiments, a fragment is a Fab. Fab, $F(ab')_2$, $F_d$, $F_v$, complementarity determining region (CDR) fragment and single-chain antibody (scFv). In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies may be prepared using a wide variety of techniques known in the art including hybridoma, recombinant, and phage display technologies, or a combination thereof. For example, monoclonal antibodies can be produced using hybridoma techniques including those known in the art and taught, for example, in Harlow and Lane, "Antibodies: A Laboratory Manual, Second Edition" Cold Spring Harbor Laboratory Press, New York (2013; ISBN-13: 978-1936113811); Hammerling et al., in: "Monoclonal Antibodies and T-Cell Hybridomas," Elsevier, New York (1981), pp. 563-681.

As used herein, a "human antibody" unless otherwise indicated is one whose sequences correspond to (i.e., are identical in sequence to) an antibody that could be produced by a human and/or has been made using any of the techniques for making human antibodies as disclosed herein. This definition of a human antibody specifically excludes a humanized antibody and also excludes an antibody actually made in a human. A "human antibody" as used herein can be produced using various techniques known in the art, including phage-display libraries (e.g., Hoogenboom and Winter, J. Mol. Biol., 227:381 (1991); Marks et al., J. Mol. Biol., 222:581 (1991)), by methods described in Cole et al., Monoclonal Antibodies and Cancer Therapy, Alan R. Liss, p. 77 (1985); Boerner et al., J. Immunol., 147(1):86-95 (1991), van Dijk and van de Winkel, Curr. Opin. Pharmacol., 5: 368-74 (2001), and by administering the antigen (e.g., cleaved amphiregulin, or cleaved amphiregulin in membrane portion) to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOMOUSE™ technology), e.g., Veloclmmune® (Regeneron, Tarrytown, N.Y.), e.g. UltiMab® platform (Medarex, now Bristol Myers Squibb, Princeton, N.J.). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome. In each of these systems, the transgenes and/or transchromosomes carried by the mice comprise human immunoglobulin variable and constant region sequences.

The term "human antibody", as used herein, is intended to include antibodies having variable regions in which both the framework and CDR regions are sequences of human origin or identical thereto. Furthermore, if the antibody (e.g., an intact antibody rather than, for example, a Fab fragment) contains a constant region, the constant region also is derived from such human sequences, e.g., human germline sequences, or mutated versions of human germline sequences. The human antibodies of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from a non-human animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., *Nature* 321:522-525 (1986); Riechmann et al., *Nature* 332:323-329 (1988); Presta, *Curr. Op. Struct. Biol.* 2:593-596 (1992); Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409. In one embodiment where the humanized antibodies do comprise residues that are not found in the recipient antibody or in the donor antibody, the Fc regions of the antibodies are modified as described in WO 99/58572.

Techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370.

Several "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. *Nature* 349: 293-299 (1991), Lobuglio et al. *Proc. Nat. Acad. Sci. USA* 86: 4220-4224 (1989), Shaw et al. *J. Immunol.* 138: 4534-4538 (1987), and Brown et al. *Cancer Res.* 47: 3577-3583 (1987). Other references describe rodent hypervariable regions or CDRs grafted into a human supporting framework region (FR) prior to fusion with an appropriate human antibody constant domain. See, for example, Riechmann et al. *Nature* 332: 323-327 (1988), Verhoeyen et al. *Science* 239: 1534-1536 (1988), and Jones et al. *Nature* 321: 522-525 (1986). Another reference describes rodent CDRs supported by recombinantly engineered rodent framework regions-European Patent Publication No. 0519596. These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g., PCT Publication No. WO99/58572; UK Patent Application No. 9809951.8. Other methods of humanizing antibodies that may also be utilized are disclosed by Daugherty et al., *Nucl. Acids Res.* 19: 2471-2476 (1991) and in U.S. Pat. Nos. 6,180,377; 6,054,297; 5,997,867; 5,866,692; 6,210,671; and 6,350,861; and in PCT Publication No. WO 01/27160.

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Methods for producing chimeric antibodies are known in the art. See e.g., Morrison, *Science* 229:1202-1207 (1985); Oi et al., *BioTechniques* 4:214-221 (1986); Gillies et al., *J. Immunol. Methods* 125:191-202 (1989); U.S. Pat. Nos. 5,807,715; 4,816,567; and 4,816,397.

The term "epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., "Epitope Mapping Protocols" in Methods in Molecular Biology, Vol. 66, Glenn E. Morris, Ed (1996). Two antibodies are said to bind to the same epitope of a protein if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI BLAST web site or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

A "host cell" is a naturally occurring cell or a transformed cell that contains an expression vector and supports the replication or expression of the expression vector. I-lost cells may be cultured cells, explants, cells in vivo, and the like. Host cells may be prokaryotic cells such as F *coli*, or eukaryotic cells such as yeast, insect, amphibian, or mammalian cells such as CH0, HeLa, and the like (see, e.g. the American Type Culture Collection catalog or the ATCC web site).

The terms "isolated," "purified," or "biologically pure" refer to material that is substantially or essentially free from components that normally accompany it as found in its native state-Purity and homogeneity are typically determined using analytical chemistry techniques such as polyacrylamide gel electrophoresis or high-performance liquid chromatography. A protein or nucleic acid that is the predominant species present in a preparation is substantially purified. Specifically, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

"Biological sample" as used herein is a sample of biological tissue or fluid that contains nucleic acids or polypeptides, e.g. of an amphiregulin protein, polynucleotide or transcript. Such samples include, but are not limited to, tissue isolated from primates (e.g. humans), or from rodents (e.g., mice, and rats). Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat: a rodent, e.g., guinea pig, rat, mouse; rabbit; or a bird; reptile; or fish.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g. as commonly used in an ELISA), biotin, digoxigenin, colloidal gold, luminescent nanocrystals (e.g., quantum dots), haptens and proteins or other entities which can be made detectable, e.g., by incorporating a radiolabel into the peptide or used to detect antibodies specifically reactive with the peptide. The radioisotope may be, for example, $^3$H, $^{14}$C, $^{32}$P, $^{35}$S, or $^{125}$I. In some cases, particularly using antibodies against the proteins of the disclosure, the radioisotopes are used as toxic moieties, as described below. The labels may be incorporated into the amphiregulin nucleic acids, proteins and antibodies at any position. Any method known in the art for conjugating the antibody to the label may be employed, including those methods described by Hunter et al, *Nature*, 144:945 (1962); David et at, *Biochemistry*, 13:1014 (1974); Pain et al. *J. Immunol. Med.*, 40:219 (1981); and Nygren, J.

Histochem. and Cytochem., 30:407 (1982)—The lifetime of radiolabeled peptides or radiolabeled antibody compositions may be extended by the addition of substances that stabilize the radiolabeled peptide or antibody and protect it from degradation. Any substance or combination of substances that stabilize the radiolabeled peptide or antibody may be used including those substances disclosed in U.S. Pat. No. 5,961,955.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin, activatable moieties, a chemotherapeutic or cytotoxic agent, a chemoattractant, a lipase; an antibiotic; or a radioisotope emitting "hard" e.g., beta radiation.

The term "cytotoxic agent as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.). and doxetaxel (Taxotere, Rhone-Poulenc Rorer. Antony, Rnace), toxotere, methotrexate, cisplatin, melphalan, vinblastine, bleomycin, etoposide, ifosfamide, mitomycin C, mitoxantrone, vincrisitine, vinorelbine, carboplatin, teniposide, daunomycin, caminomycin, aminopterin, dactinomycin, mitomycins, esperamicins (see U.S. Pat. No. 4,675,187), 5-FU, 6-thioguanine, 6-mercaptopurine, actinomycin D, VP-16, chloranbucil, melphalan, and other related nitrogen mustards. Also included in this definition are hormonal agents that act to regulate or inhibit hormone action on tumors such as tamoxifen and onapristone.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids. antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins: chelating agents such as EDTA; sugar alcohols such as mannitol or sorbitol; salt-forming, counterions such as sodium; and/or nonionic surfactants such as TWEEN™, polyethlene glycol (PEG), and PLURONICS™.

A "pharmaceutically effective" or "therapeutically effective" amount, in reference to the treatment of tumor. refers to an amount capable of invoking one or more of the following effects: (1) inhibition, to some extent, of tumor growth, including, slowing down and complete growth arrest; (2) reduction in the number of tumor cells; (3) reduction in tumor si/e; (4) inhibition (i.e., reduction, slowing down or complete stopping) of tumor cell infiltration into peripheral organs; (5) inhibition (i.e., reduction. slowing down or complete stopping) of metastasis; (6) enhancement of anti-tumor immune response, which may, but does not have to, result in the regression or rejection of the tumor; and/or (7) relief, to sortie extent, of one or more symptoms associated with the disorder. A "therapeutically effective amount" of an anti-cleaved amphiregulin antibody for purposes of treatment of tumor may be determined empirically and in a routine manner.

"Treatment" refers to both therapeutic treatment and prophylactic or preventative measures. Those in need of treatment include those already with the disorder as well as those in which the disorder is to be prevented.

A "subject" refers to a vertebrate, preferably a mammal, more preferably a human.

The term "cancer" refers to any type of physiological condition found in mammals typically characterized by unregulated cell growth (e.g., neoplasm or malignant tumor) including carcinomas, lymphomas, blastomas, sarcomas, or hematopoietic neoplastic disorders, Examples of cancers include, but are not limited to. Hodgkin's Disease, Non-Hodgkin's Lymphoma, multiple myeloma, leukemia, neuroblastoma. breast cancer, ovarian cancer, lung cancer, cancers of head and neck, cancer of endothelium, cancers of bone, cancers of muscle, pancreatic cancer, rhabdomyosarcoma, primary thrombocytosis, primary macroglobulinemia, small-cell lung tumors, stomach cancer, colon cancer, kidney cancer. malignant pancreatic insulanoma, malignant carcinoid, urinary bladder cancer, melanoma, premalignant skin lesions, testicular cancer, lymphomas, thyroid cancer, esophageal cancer, genitourinary tract cancer, malignant hypercalcemia, cervical cancer, endometrial cancer, epidermal cancer, adrenal cortical cancer, prostate cancer, or uterine cancer. Cancer cells are the cancerous cells of any type of cancers, which can be cells of cancer tissues from a patient or cells of an established cancer cell line.

"Tumor", as used herein, refers to all neoplastic cell growth and proliferation, whether malignant or benign, and all pre-cancerous and cancerous cells and tissues.

The term "amphiregulin" refers to nucleic acid and polypeptide polymorphic variants, alleles, mutants, and interspecies homologues of amphiregulin, including those that have an amino acid sequence that has greater than about 60% amino acid sequence identity, 65%. 70%. 75%. 80%, 85%, 90%, preferably 91%, 92%, 93%, 94%, 95%. 96%, 97%, 98% or 99% or greater amino sequence identity, preferably over a region of at least about 25. 50. 100, 200, or more amino acids, to an amino acid sequence of SEQ ID NO:1. An amphiregulin polynucleotide or polypeptide sequence is typically from a mammal, including. but not limited to, primate, e.g., human; rodent, e.g., rat, mouse, hamster; cow, pig, horse, sheep, or other mammal. An "amphiregulin polypeptide" and a "amphiregulin polynucleotide," include both naturally occurring and recombinant forms.

In one embodiment, the amphiregulin is human amphiregulin. The sequence of the precursor protein of human amphiregulin is set forth in SEQ ID NO: 1 (GenBank Accession No. AAA51781.1). The transmembrane sequence is residues 200 through 221 of SEQ ID NO: 1. The N-terminus of protein is outside cell. The C-terminus of protein is inside cell. The neo-epitope is revealed by cleavage between K187 and T188, leaving an extracellular epitope, the amphiregulin neo-epitope, of THSMIDSSLSKI (SEQ ID NO:2', i.e., residues 188 through 199 of SEQ ID NO:1. Thus, in an embodiment, a "cleaved" amphiregulin precursor protein would result from the cleavage of SEQ ID NO: 1 between K187 and T188 thereof, with the C-terminal portion remaining associated with the cell membrane. In an embodiment. the cleaved amphiregulin precursor protein consists of residues 188-252 of SEQ ID NO:1 and does not comprise residues 1-1-87 of SEQ ID NO:1.

(The transmembrane sequence is in BOLD; SEQ ID NO: 2 is underlined):

SEQ ID NO: 1

```
  1 MRAPLLPPAP VVLSLLILGS GHYAAGLDLN DTYSGKREPF SGDHSADGFE VTSRSEMSSG

61 SEISPVSEMP SSSEPSSGAD YDYSEEYDNE PQIPGYIVDD SVRVEQVVKP PQNKTESENT

121 SDKPKRKKKG GKNGKNRRNR KKKNPCNAEF QNFCIHGECK YIEHLEAVTC KCQQEYFGER

181 CGEKSMKTHS MIDSSLSKIA LAAIAAFMSA VILTAVAVIT VQLRRQYVRK YEGEAEERKK

241 LRQENGNVHA IA
```

The antibodies against cleaved amphiregulin (i.e., anti-cleaved amphiregulin antibodies) disclosed herein may be in a polyclonal or monoclonal form and should selectively bind to the epitope with the amino acid sequence that has at least 60% identity, 65%, 70%, 75%, 80%, 85%, 90%, preferably 91%, 92%, 93%. 94%, 95%. 96%, 97%, 98% or 99% or greater amino sequence identity to SEQ ID NO:2, preferably in a cleaved human amphiregulin. The antibodies include antibodies having all types of constant regions, including IgM, IgG, IgD, IgA and IgE, and any isotype, including IgG1, IgG2a, Ig32b, IgG3 and IgG4. The light chain can be kappa or lambda light chain.

In a preferred aspect, anti-cleaved amphiregulin antibodies preferably bind to the epitope at a binding affinity of at least $10^6 M^{-1}$, $10^7 M^{-1}$, $10^8 M^{-1}$, $10^9 M^{-1}$ and $10^{10} M^{-1}$.

Disclosed herein are anti-cleaved amphiregulin antibodies comprising a heavy chain variable region comprising an amino acid sequence selected from SEQ ID NOs: 3, 5, and 7 and polypeptides having at least 60% sequence identity thereto. These antibodies may further comprise a light chain variable region comprising amino acid sequence selected from SEQ ID NOs: 4, 6 and 8 and polypeptides having at least 60% sequence identity thereto. The determination of epitope type is accomplished by methods known in the art, such as a competition assay, which, for example, may be detected by changes in fluorescence intensity as measured by flow cytometry. In cases where the epitopes of the two or more antibodies are similar, the antigen-binding sites will be occupied by the first antibody and the second antibody conjugate will be unable to bind cells. This results in loss of signal of this conjugate, so that the fluorescence intensity will be reduced.

The various amino acid sequences disclosed herein have been assigned the following Sequence Identification Numbers (SEQ ID NOs), which are also submitted herewith in a formal Sequence List:

SEQ ID NO: 1 (Precursor protein of human amphiregulin; GenBank Accession No. AAA51781.1)
(SEQ ID NO: 1)
MRAPLLPPAPVVLSLLILGSGHYAAGLDLNDTYSGKREPFSGDHSADGF

EVTSRSEMSSGSEISPVSEMPSSSEPSSGADYDYSEEYDNEPQIPGYIV

DDSVRVEQVVKPPQNKTESENTSDKPKRKKKGGKNGKNRRNRKKKNPCN

AEFQNFCIHGECKYIEHLEAVTCKCQQEYFGERCGEKSMKTHSMIDSSL

SKIALAAIAAFMSAVILTAVAVITVQLRRQYVRKYEGEAEERKKLRQEN

GNVHAIA

SEQ ID NO: 2 (Sequence of the extracellular portion of cleaved amphiregulin, starting with the first post-cleavage amino acid residue)

(SEQ ID NO: 2)
THSMIDSSLSKI

SEQ ID NO: 3 (1A3 antibody, Heavy chain $V_H$)
(SEQ ID NO: 3)
QSVKESEGRLVTPGTPLRLTCTVAGYSLSRYHMCWVRQAPGKGLEWIGM

IGGSGRTDYASWAKGRFTISKTSTTVDLKITSPTTEDTATYFCSTVYTD

SDGDFWGPGTLVTVSS

SEQ ID NO: 4 (1A3 antibody, Light chain $V_L$)
(SEQ ID NO: 4)
AELDMTQTPSSKSVPVGGTVTINCQASESVYSNDRLAWFQQKPGQPPKL

LIYYASTLASGVPSRFKGSGSGTQFTLTISDLECADAATYYCQSCYDMS

SYGVAFGGGTELEIL

SEQ ID NO: 5 (3A3 antibody, Heavy chain $V_H$)
(SEQ ID NO: 5)
QQQLVESGGRLVTPGTPLTLTYTVSGFSLSDYHMSWVRQAPGKGLQWIA

TISNRGNTYYASWAKGRFTISKTSTTVDLKITSPTTEDTATYFCARDNV

HGDGVLVFYLWGPGTLVTVSS

SEQ ID NO: 6 (3A3 antibody, Light chain $V_L$)
(SEQ ID NO: 6)
AELVMTQTPASVSEPVGGTVTIKCQASQSIGTNLAWYQQKPGQPPKRLI

YKASTLASGVSSRFKGSGSGTEFTLTISDLECADAATYYCQGYYSGDSN

AFGGGTEVVVK

SEQ ID NO: 7 (3E4 antibody, Heavy chain $V_H$)
(SEQ ID NO: 7)
QSVKESEGRLVTPGTPLTLTCTVSGFSLSDYWMSWVRQAPGKGLEWIGI

AGYSDNTYYASRAKGRFTISKTSTTVVLKITRPTTEDTATYFCVRDLYG

VYSSGTTLWGPGTLVTVSS

SEQ ID NO: 8 (3E4 antibody, Light chain $V_L$)
(SEQ ID NO: 8)
AELVMTQTPSPVSAAVGGTVTISCQSSQSVYNNNRLAWFQQKPGQPPKL

LIYYASTLASGVSSRFKGSGSGTQFTLIISDVVCDDAATYYCQGYYSGG

ITGFGGGTEVVVK

SEQ ID NO: 9 (Uncleaved AREG)
(SEQ ID NO: 9)
SMKTHSMIDSSLSKIAC

Also disclosed herein are analogs of the antibodies described herein. Preferred analogs include antibodies comprising heavy chain variable regions having about at least 60%, 80% or 90-95% amino acid sequence identity of SEQ ID NOs: 3, 5, and 7 and/or comprising light chain variable regions having about at least 60%, 80% or 90-95% amino acid sequence identity of SEQ ID NOs:4, 6 and 8.

Methods of determining percent identity are known in the art. "Percent (%) sequence identity" with respect to a specified subject sequence, or a specified portion thereof, may be defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.* 215:403-410 (1997); blast.wustl web site) with search parameters set to default values. The HSP S and HSP S2 parameters are dynamic values and are established by the program itself depending upon the composition of the sequence and composition of the database against which the sequence of interest is being searched. Any two antibody sequences can only be aligned in one way, by using the numbering scheme in Kabat ("Sequences of Proteins of Immunological Interest" Kabat, E. et al., U.S. *Department of Health and Human Service* (1983)). Therefore, for antibodies, percent identity has a unique and well-defined meaning. A "% identity value" is determined by the number of matching identical nucleotides or amino acids divided by the sequence length for which the percent identity is being reported.

Additional preferred analogs of exemplified antibodies differ from exemplified antibodies by conservative amino acid substitutions. For purposes of classifying amino acids substitutions as conservative or nonconservative, amino acids may be grouped as follows: Group I (hydrophobic sidechains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Antibodies against cleaved amphiregulin of all species of origins are included in this disclosure. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584). Natural antibodies are the antibodies produced by a host animal. In a preferred embodiment, the antibody is an isolated monoclonal antibody that selectively binds to cleaved amphiregulin.

The monoclonal antibodies are produced by conventional hybridoma methodology known in the art. The hybridoma technique described originally by Kohler and Milstein, *Nature* 256: 495-7 (1975); *Eur. J. Immunol.* 6: 511 (1976)) has been widely applied to produce hybrid cell lines that secrete high levels of monoclonal antibodies against many specific antigens.

The polyclonal forms of the anti-cleaved amphiregulin antibodies are also included in the present disclosure. Preferably, these antibodies selectively bind to the epitopes that the described monoclonal antibodies bind to in the present disclosure. The polyclonal antibody can be produced by immunization of host animals by cleaved amphiregulin or fragment thereof. The polyclonal antibodies are secreted into the bloodstream and can be recovered using known techniques. Purified forms of these antibodies can, of course, be readily prepared by standard purification techniques, preferably including affinity chromatography with Protein A, anti-immunoglobulin, or the antigen itself. In any case, in order to monitor the success of immunization, the antibody levels with respect to the antigen in serum will be monitored using standard techniques such as ELISA, RIA and the like.

Genetically-altered (i.e. recombinant) antibodies against cleaved amphiregulin are also included in the present disclosure. These recombinant antibodies have the same amino acid sequence as the natural antibodies or have altered amino acid sequences of the natural antibodies in the present disclosure. They can be made in any expression systems including both prokaryotic and eukaryotic expression systems or using phage display methods (see, e.g., Dower et al., WO91/17271 and McCafferty et al., WO92/01047; U.S. Pat. No. 5,969,108).

The genetically altered anti-cleaved amphiregulin antibodies should be functionally equivalent to the above-mentioned natural antibodies and recombinant antibodies (although specific functionalities, for example binding affinity, may differ). Modified antibodies providing improved stability and/or therapeutic efficacy are preferred. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this disclosure can be modified post-translationally (e.g., acetylation, and phosphorylation) or can be modified synthetically (e.g., the attachment of a labeling group, such as a cytotoxic agent). Preferred genetically altered antibodies are chimeric antibodies and humanized antibodies.

Included in this disclosure are chimeric antibodies comprising a variable region derived from a rabbit and a constant region derived from human, so that the chimeric antibody has a longer half-life and is less immunogenic when administered to a human subject. In one embodiment, the murine variable regions are derived from any one of the monoclonal antibodies described herein, including the non-limiting examples: a) the monoclonal antibodies comprising a mature heavy chain variable region comprising amino acid sequence selected from SEQ ID NOs:3, 5 and 7 and/or a mature light chain variable region comprising amino acid sequence selected from SEQ ID NOs:4, 6 and 8; b) the antibodies that bind to the same epitope of a); or c) the analogs of a).

To produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making the chimeric antibody is disclosed in U.S. Pat. Nos. 5,677,427; 6,120,767; and 6,329,508.

The genetically altered antibodies disclosed herein also include humanized antibodies that bind to cleaved amphiregulin. Methods of making humanized antibody are disclosed in U.S. Pat. Nos. 5,530,101; 5,585,089; 5,693,761; 5,693,762; and 6,180,370. In one embodiment of the present disclosure, the humanized antibody comprises CDRs of a rabbit donor immunoglobulin and heavy chain and light chain frameworks of a human acceptor immunoglobulin. For example, the humanized versions of a) the monoclonal antibodies comprising a mature heavy chain variable region comprising amino acid sequence of SEQ ID NOs:3, 5 or 7 and/or a mature light chain variable region comprising amino acid sequence of SEQ ID NOs:4, 6 or 8; b) the antibodies that bind to the same epitope of a); or c) the analogs of a).

Anti-cleaved amphiregulin primatized or fully human antibodies are also included in the present disclosure. Fully human antibodies against cleaved amphiregulin are produced by a variety of techniques. One example is trioma methodology. The basic approach and an exemplary cell fusion partner, SPAZ-4, for use in this approach have been described by Oestberg et al., *Hybridoma* 2:361-367 (1983); Oestberg, U.S. Pat. No. 4,634,664; and Engleman et al., U.S. Pat. No. 4,634,666.

Human antibodies against cleaved amphiregulin can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584.

Various recombinant antibody library technologies may also be utilized to produce fully human antibodies. For example, one approach is to screen a DNA library from human B cells according to the general protocol outlined by Huse et al., *Science* 246:1275-1281 (1989). Antibodies binding cleaved amphiregulin or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047; U.S. Pat. No. 5,969,108. In these methods, libraries of phage are produced in which members display different antibodies on their outer surfaces. Antibodies are usually displayed as Fv or Fab fragments. Phage displaying antibodies with a desired specificity are selected by affinity enrichment to cleaved amphiregulin or fragment thereof.

Eukaryotic ribosome can also be used as a mean to display a library of antibodies and isolate the binding human antibodies by screening against the target antigen, such as AR, as described in Coia G, et al., *J. Immunol. Methods* 1: 254 (1-2): 191-7 (2001); Hanes J. et al., *Nat. Biotechnol.* 18(12): 1287-92 (2000); *Proc. Natl. Acad. Sci. U.S.A.* 95(24): 14130-5 (1998); *Proc. Natl. Acad. Sci. U.S.A.* 94(10): 4937-42 (1997).

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., *Biotechnol. Prog.* 18(2):212-20 (2002); Boeder, E. T., et al., *Nat. Biotechnol.* 15(6):553-7 (1997). Alternatively, human antibody libraries may be expressed intracellularly and screened via yeast two-hybrid system (WO0200729A2).

Fragments of the anti-cleaved amphiregulin antibodies, which retain the binding specificity to cleaved amphiregulin, are also disclosed. Examples include, but are not limited to, partial or full heavy chains or light chains, variable regions, or CDR regions of any anti-cleaved amphiregulin antibodies described herein.

The antibody fragments may optionally be truncated chains (truncated at the carboxyl end). Preferably, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dab fragments (consisting of a $V_H$ domain); isolated CDR regions; (Fab')2 fragments, bivalent fragments (comprising two Fab fragments linked by a disulphide bridge at the hinge region). The truncated chains can be produced by conventional biochemistry techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')2 fragments. Single chain antibodies may be produced by joining VL and VH coding regions with a DNA that encodes a peptide linker connecting the VL and VH protein fragments.

Because the immunoglobulin-related genes contain separate functional regions, each having one or more distinct biological activities, the genes of the antibody fragments may be fused to functional regions from other genes (e.g., enzymes, U.S. Pat. No. 5,004,692) to produce fusion proteins (e.g., immunotoxins) or conjugates having novel properties.

One version of the method comprises the use of anti-cleaved amphiregulin antibodies conjugated to various effector moieties including but not limited to immunotoxins. Conjugates that are immunotoxins including antibodies have been widely described in the art. The toxins may be coupled to the antibodies by conventional coupling techniques or immunotoxins containing protein toxin portions can be produced as fusion proteins. The conjugates disclosed herein can be used in a corresponding way to obtain such immunotoxins. Illustrative of such immunotoxins are those described by Byers, B. S. et al., *Seminars Cell Biol* 2:59-70 (1991) and by Fanger, M. W. et al., *Immunol Today* 12:51-54 (1991).

Recombinant DNA techniques can be used to produce the recombinant anti-cleaved amphiregulin antibodies, as well as the chimeric or humanized anti-cleaved amphiregulin antibodies or any other anti-cleaved amphiregulin genetically altered antibodies and the fragments or conjugate thereof in any expression systems including both prokaryotic and eukaryotic expression systems, such as bacteria, yeast, insect cells, plant cells, mammalian cells (for example, NSO cells).

Once produced, the whole antibodies, their dimers, individual light and heavy chains, or other immunoglobulin forms of the present disclosure can be purified according to standard procedures of the art, including ammonium sulfate precipitation, affinity columns, column chromatography, gel electrophoresis and the like (see, generally, Scopes, R., "Protein Purification" (Springer-Verlag, N.Y., 1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent staining, and the like. (See, generally, Immunological Methods, Vols. I and II (Lefkovits and Pernis, eds., Academic Press, N Y, 1979 and 1981).

The anti-cleaved amphiregulin antibodies disclosed herein are useful in cancer prevention or treatment. In one preferred aspect, the present disclosure provides for a method of inhibiting the proliferation of tumor cells comprising contacting the tumor cells with the anti-cleaved amphiregulin antibodies conjugated to an effector moiety, such as a cytotoxic agent, in a pharmaceutically effective amount. The conjugates contact with tumor cells in vitro, ex vivo or in vivo (such as in a subject, preferably in a mammal, and more preferably in a human). In one embodiment, the tumor is an ER+ tumor. In an embodiment, the tumor is a tumor of the breast. In an embodiment, the tumor is a tumor of the lung, liver, prostate, or is a colorectal tumor. Such an inhibition reduces the tumor cell proliferation by at least 10%, 30%, 50%, 70%, 80%, or 90%.

The inhibitory effect of the antibody-drug conjugates on the tumor proliferation can be measured by cell-based assays, such as bromodeoxyuridine (BRDU) incorporation (Hoshino et al., *Int. J. Cancer* 38, 369 (1986); Campana et al., *J. Immunol. Meth.* 107:79 (1988)); [3H]-thymidine incorporation (Chen, J., Oncogene 13:1395-403 (1996); Jeoung, J., *J. Biol. Chem.* 270:18367-73(1995); the dye Alamar Blue (available from Biosource International) (Voytik-Harbin SL et al., *In Vitro Cell Dev Biol Anim* 34:239-46 (1998)); colony formation assay in soft agar (Green and Sambrook, "*Molecular Cloning: A Laboratory Manual* (Fourth Edition), Cold Spring Harbor Press, 2012, ISBN-10: 1936113422).

The inhibition is also assessed via tumorigenicity assays. In one example, a xenograft comprises human cells from a pre-existing tumor or from a tumor cell line. Tumor xenograft assays are known in the art (see, e.g., Ogawa K et al., *Oncogene* 19:6043-6052 (2000)). In another preferred embodiment, tumorigenicity is monitored using a hollow fiber assay, which is described in U.S. Pat. No. 5,698,413.

In certain embodiments, a cytotoxic drug or other therapeutic or diagnostic agent may be covalently attached to an antibody or antibody fragment to form an immunoconjugate. In some versions, a drug or other agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation.

Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, Chemistry of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in *Monoclonal Antibodies: Production, Engineering and Clinical Application*, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., *Int. J Cancer* 41: 832 (1988); Shih et al., *Int. J. Cancer* 46: 1101 (1990); and Shih et al., U.S. Pat. No. 5,057,313. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, *Angew Chem Int Ed* 40:3004-31; Evans, 2007, *Aust J Chem* 60:384-95.) Various forms of click chemistry reaction are known in the art, such as the Huisgen 1,3-dipolar cycloaddition copper catalyzed reaction (Tornoe et al., 2002, *J Organic Chem* 67:3057-64), which is often referred to as the "click reaction." Other alternatives include cycloaddition reactions such as the Diels-Alder, nucleophilic substitution reactions (especially to small, strained rings like epoxy and aziridine compounds), carbonyl chemistry formation of urea compounds and reactions involving carbon-carbon double bonds, such as alkynes in thiol-yne reactions.

Alternatively, methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240.

The above-described methods of the present disclosure inhibit, reverse tumor proliferation, or metastasis, or reduce the size of tumor in the subject.

Examples disclosed herein exemplify assays demonstrating effects of anti-cleaved amphiregulin antibodies conjugated to a cytotoxic agent on inhibiting cell proliferation and xenograft tumor growth.

The antibodies described herein can be used for the wound healing, enhancing skin qualities, or providing benefit to any other disorders caused by the abnormal hyperactivity of amphiregulin.

Therapeutic methods are usually applied to human patients but may be applied to other mammals.

There are various methods of administering the antibodies disclosed herein. Parenteral administration is preferred. The antibody may be administered to a patient intravenously as a bolus or by continuous infusion over time; or by intramuscular, subcutaneous, intraperitoneal, or intra-cerebrospinal routes. Oral, topical, inhalation routes, or other delivery means known to those skilled in the art are also included in the present disclosure.

The pharmaceutical compositions disclosed herein commonly comprise a solution of antibodies or a cocktail thereof dissolved in an acceptable carrier, preferably an aqueous carrier. That is, the antibodies can be used in the manufacture of a medicament for treatment of patients. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc. to make isotonic. The carrier can also contain excipients such as human serum albumin, polysorbate 80, sugars or amino acids to protect the active protein. The concentration of antibodies in these formulations varies widely from about 0.1 to 100 mg/ml but is often in the range 1 to 10 mg/ml. The formulated monoclonal antibody is particularly suitable for parenteral administration and can be administered as an intravenous infusion or by subcutaneous, intramuscular or intravenous injection. Actual methods for preparing parentally administrable compositions are known or apparent to those skilled in the art and are described in more detail in, for example, *Remington: The Science and Practice of Pharmacy* (23rd Ed., Academic Press, Cambridge, MA; 2020; ISBN-13: 978-0128200070).

Disclosed herein is a pharmaceutical composition comprising an antibody that binds to cleaved amphiregulin, preferably one of the antibodies described herein. In certain embodiments, the antibody is conjugated to an effector moiety, such as a cytotoxic agent, and administered for prophylactic and/or therapeutic treatments. An amount adequate to accomplish the desired effect is defined as a "pharmaceutically effective amount". Preferred optimal dosing may include a dosage. of between 4 mg/kg and 18 mg/k. Exemplary dosages of use may include 1 mg/kg, 2 mg/kg, 3 mg/kg, 4 mg/kg, 5 mg/kg, 6 mg/kg, 7 mg/kg, 8 mg/kg. 9 mg/kg, 10 mg/kg, 11 mg/kg, 12 mg/kg, 13 mg/kg, 14 mg/kg, 15 mg/kg, 16 mg/kg, 17 mg/kg. 18 mg/kg, 19 mg/kg, 20 mg/kg, 22 mg/kg and 24 mg/kg. Preferred dosages are 4. 6. 8, 9, 10, 12, 14, 16 or 18 ng/kg. More preferred dosages are 6-12. 6-8, 7-8, 8-10, 10-12 or 8-12 mg/kg. The antibody-drug conjugate can be delivered into a patient by single or multiple administration, e.g., 1, 2 or 3 times per day. week or month for one to several days, weeks, months or years, or chronically, depending upon the nature and severity of the disease.

For inhibiting the growth of neoplastic cells, the appropriate dosage of the antibodies will depend on the severity and course of disease, the patient's clinical history and response, the toxicity of the antibodies, and the discretion of the attending physician. The antibody-drug conjugate is suitably administered to the patient at one time or over a series of discrete treatments. The initial candidate dosage may be administered to a patient. The proper dosage and treatment regimen can be established by monitoring the progress of therapy using conventional techniques known to the people skilled of the art.

Additionally, the antibodies can be utilized alone in substantially pure form, or together with therapeutic agents, as are known to those of skill in the art (see, e.g., *Cancer: Principles and Practice of Oncology,* 11th ed., Devita et al., Lippincott-Ravel Publishers, 2018; ISBN-13: 978-1496394637). Other therapies that may be used in conjunction with treatment with the antibodies include administration of anti-sense nucleic acid molecules or biologicals, such as additional therapeutic antibodies. Thus, the treatment disclosed herein is formulated in a manner allowing it to be administered serially or in combination with another therapeutic methods for the treatment of cancer, such as chemotherapy, radiation therapy and surgery.

The antibodies disclosed herein are useful in diagnostic and prognostic evaluation of diseases and disorders, particularly cancers associated with amphiregulin expression. At each stage of disease, the antibodies disclosed herein may be used to improve diagnostic accuracy and facilitate treatment decisions.

Methods of diagnosis can be performed in vitro using a cellular sample (e.g., blood sample, lymph node biopsy or tissue) from a patient or can be performed by in vivo imaging.

In specific embodiments, the present disclosure provides an antibody conjugate wherein the antibodies disclosed herein are conjugated to a diagnostic imaging agent.

Compositions comprising the antibodies disclosed herein can be used to detect cleaved amphiregulin, for example, by radioimmunoassay, ELISA, FACS, etc. One or more labeling moieties can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

Also disclosed herein is a method of detecting a cancer comprising detecting the differential expression of mRNA or protein of cleaved amphiregulin in the cancer cells in a subject in need of such detection.

In one exemplary embodiment, the method of detecting cancer comprises: a) isolating a sample from a patient; b) contacting cells of the sample with the antibodies disclosed herein; c) contact non-cancerous cells of the same type of cells of the sample cells with the antibodies disclosed herein; and d) detecting and comparing the difference of expression of cleaved amphiregulin in the sample cells with the non-cancerous cells.

In addition to detecting the cancer at pre- or early disease stage, the antibodies disclosed herein can also be used to evaluate the treatment efficacy of a therapeutic approach. Antibodies are utilized to detect the expression level of cleaved amphiregulin before and after certain treatment. Reduction in cleaved amphiregulin expression level may be an indicator of the effectiveness of the treatment.

The antibodies disclosed herein can also be used as detecting agents for in vitro assays for research purposes. For example, the antibodies can be used to identify or isolate the novel receptors or other binding proteins for cleaved amphiregulin via the methods known in the art, such as by screening protein expression libraries.

Also disclosed herein is a diagnostic kit comprising anti-cleaved amphiregulin antibodies. Such a diagnostic kit further comprises a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

Though the antibodies described herein are primarily concerned with the treatment of human subjects, they may also be employed for treating other mammalian subjects such as dogs and cats for veterinary purposes.

The following examples are offered by way of illustration and not by way of limitation.

EXAMPLES

Example 1

SUMMARY

The Epidermal Growth Factor Receptor (EGFR) ligand, Amphiregulin (AREG), is a key proliferative effector of estrogen receptor signaling in breast cancer and also plays a role in other malignancies. AREG is a single-pass transmembrane protein proteolytically processed by TACE/ADAM17 to release the soluble EGFR ligand, leaving a residual transmembrane stalk that is subsequently internalized. Using phage display, this Example identified antibodies that selectively recognize the residual transmembrane stalk of cleaved AREG. Conjugation with fluorescence labels and monomethyl auristatin E (MMAE) was used to study their intracellular trafficking and anti-cancer effects, respectively. Thus, reported herein is the development of an antibody-drug conjugate (ADC), GMF-1A3-MMAE, targeting an AREG neo-epitope revealed following ADAM17-mediated cleavage. The antibody does not interact with uncleaved AREG, providing a novel means of targeting cells with high rates of AREG shedding. Using fluorescent dye conjugation, it is demonstrated that the antibody is internalized by cancer cells in a manner dependent on the presence of cell surface cleaved AREG. Antibodies conjugated with MMAE were cytotoxic in vitro and induced rapid regression of established breast tumor xenografts in immunocompromised mice. It is further demonstrated that these antibodies recognize the AREG neo-epitope in formalin-fixed, paraffin-embedded tumor tissue, suggesting their utility as a companion diagnostic for patient selection. This ADC targeting AREG can be used in the treatment of breast and other tumors in which proteolytic AREG shedding is a frequent event.

Materials and Methods

Cell Lines and Culture Conditions:

Human breast cancer cell line MCF7 was obtained from American Type Culture Collection (Manassas, VA, USA). The cell line was cultured in high-glucose Dulbecco's modified Eagle medium (DMEM) supplemented with 10% fetal bovine serum (Gibco, Life Technologies, Carlsbad, CA, USA) at 37° C. in 5% $CO_2$. The MCF7 fulvestrant-resistant subline (MCF7-F) was kindly provided by Dr. Kenneth P. Nephew and cultured as previously described." Cell lines were authenticated by STR profiling.

Antibodies:

Rabbit monoclonal IgG antibodies specific to cleaved-AREG were identified in contracted screening (Oak Biosciences Inc., Sunnyvale, CA, USA) using a recombinant Rabbit naïve phage display library (scFv format, $V_K$-linker-$V_H$) screening platform after four rounds of panning and ELISA validation. For panning, phage was selected against a peptide modeling the ADAM17-cleaved cell-associated epitope of AREG,[12] represented by the N-terminal region of THSMIDSSLSKI (SEQ ID NO: 2), and counter-selected against a peptide spanning this region (SMKTHSMIDSSLSKIAC; SEQ ID NO: 9), representing uncleaved AREG. Three candidate clones-GMF-1A3, GMF-3A3 and GMF-3E4-were reformatted as IgG and selectivity for cleaved AREG was confirmed by ELISA. GMF-1A3, referred to hereafter as simply "1A3", was the antibody chosen for further characterization in this Example.

Immunohistochemistry:

A breast disease spectrum tissue micro-array was purchased from US Biomax Inc. (Derwood, MD, USA). The slides were deparaffinized in xylene and rehydrated by serial incubations in graded ethanol and then in water in a Histo-Tek® SL Slide Stainer (Sakura Finetek USA, Inc., Torrance, CA, USA). Antigen retrieval was performed in a steamer by boiling slides in a container of citrate buffer (pH 6.0) for 20 min, which was then removed for 15 min of cooling on the benchtop. Slides were washed in 1×Wash buffer (Dako Agilent, Santa Clara, CA, USA) and endogenous peroxidase was quenched by incubating with Dako Dual Endogenous Enzyme Block (S2003) for 10 min. Slides were washed in 1× Wash buffer, blocked (5% rabbit/10% goat serum in PBS), and immunostained with goat anti-AREG antibody (15 µg/mL; AF262, R&D Systems) or rabbit anti-cleaved AREG 1A3 antibody (10 µg/mL) overnight at 4° C. Slides were washed four times in 1× Wash buffer, followed by the incubation for 45 min at room temperature in 1:100 dilution of rabbit anti-goat immunoglobulins/HRP (Dako, P0160 or ready-to-use goat anti-rabbit HRP labeled polymer (Dako, K4003). The slides were washed twice in 1× Wash buffer and the color was developed with 3,3-diaminobenzidine tetrahydrochloride substrate chromogen system (K3468, DAKO, Santa Clara, CA, USA). Sections were washed with water and counterstained with hematoxylin, rinsed with water, dehydrated by serial ethanol washes to 100%, cleared and mounted in Permount (Thermo Fisher Scientific). The staining intensity was assessed semi-quantitatively using a four-point scale (negligible=0, low=1, medium=2, high=3) by two investigators working independently on blinded samples. Discordant scores were resolved by joint review.

Internalization and Intracellular Localization Analysis of Anti-Cleaved-AREG 1A3 Antibody:

In order to study internalization, 1A3 was conjugated with pHrodo iFL Red dye using pHrodo iFL Red Microscale Protein Labeling Kit (P36014, Thermo Fisher Scientific). MCF7 cells were seeded in 12 mm Nunc Glass Bottom Dish, at a density of 1 ×10$^5$ cells/dish. After allowing the cells to attach overnight, the cells were incubated for 60 min with 1 mg/mL Hoechst dye for nuclei staining and LysoTracker® Green DND-26 (Thermo Fisher Scientific) for lysosomal labeling. The cells were then incubated with 1A3-pHrodo (2 µg/mL) for 20 min at 37° C. After washing the wells with PBS, the cells were supplemented with 1× live-cell imaging solution (Molecular probes, Thermo Fisher Scientific). Fluorescence images were acquired at 30 min intervals for 2.5 h with the Olympus 1×71 inverted fluorescence microscope (Olympus, Shinjuku, Tokyo, Japan). TAPI-2 (20 µM)—pretreatment was performed overnight, with DMSO serving as a control.

Preparation and Characterization of ADCs

Monomethyl auristatin E (MMAE) conjugated 1A3 antibody (1A3-VC-PAB-MMAE) was prepared using a kit (CM11409) from CellMosaic Inc. (Woburn, MA, USA) following the manufacturer's instructions. Maleimide-activated valine-citrulline p-aminobenzylcarbamate (VCPAB) MMAE was coupled directly to the antibody after reduction through alkylation.[13] The specificity of 1A3 and 1A3-VC-PAB-MMAE to peptides representing human cleaved-AREG was confirmed by immunoblotting. Briefly, transferrin (TRF) conjugated peptides representing cleaved and uncleaved AREG (200 ng) were electrophoresed on SDS-PAGE gels, transferred to PVDF membrane and probed with 1 µg/mL of 1A3 and 1A3-VC-PAB-MMAE. Horseradish peroxidase-conjugated goat anti-rabbit IgG was used. Antibody binding was detected with enhanced chemiluminescence (ECL; Amersham, Arlington Heights, IL, USA). Furthermore, the characterization and purity of 1A3-VC-PAB-MMAE were analyzed using hydrophobic interaction chromatography (HIC) and size-exclusion chromatography (Cell Mosaic).

Binding affinity of 1A3 and 1A3-VC-PAB-MMAE by ELISA:

Maxisorp flat bottom 96-well plates (Thermo Fisher Scientific) were coated with 5 µg/mL cleaved-AREG peptide at 4° C. overnight. After washing thrice with PBST (PBS with 0.05% Tween20) and blocking for 2 h at RT with 5% non-fat dry milk in PBST, various concentrations of 1A3 and 1A3-VC-PAB-MMAE (0.001, 0.01, 0.1, 1 µg/mL) were added to the wells and incubated for 2 h at RT. The wells were washed four times with PBST and were incubated at RT with Goat anti-rabbit IgG (H+L) Cross-adsorbed-HRP conjugate secondary Ab (ThermoFisher G-21234) for 1 h. One-Step™ Turbo™ B-ELISA Substrate Solution (Thermo Fisher Scientific) was added to the wells for color development, incubated for 15 min and the reaction was stopped by adding 2 M $H_2SO_4$. The absorbance was measured at 450 nm using VersaMax Microplate Reader (Molecular Devices LLC, San Jose, California, USA).

In Vitro Antitumor Studies:

MTT assay: The cytotoxic effect of 1A3 and 1A3-VC-PAB-MMAE antibodies on MCF7 and MCF7-F breast cancer cells were determined using an MTT (3-(4,5-Dimethylthiazol2-yl)-2,5-Diphenyltetrazolium Bromide) assay. The cells were seeded at a density of 5000 cells/well in 96-well plates. Approximately 24 h after cell seeding, the cells were treated with varying doses (1.56, 3.125, 6.25, 12.5, 25, 50, 100 and 200 nM) of MMAE, 1A3 and 1A3-VC-PAB-MMAE. Untreated cells were used as control. After incubating for 72 h, the medium was aspirated and 50 µL of serum-free media and 50 µL of MTT solution (5 mg/mL solution in PBS) was added into each well; the cells were then incubated for 3 h at 37° C. The formazan crystals formed were dissolved with 4 mM HCl, 0.1% NP40 in isopropanol. The absorbance was measured at 590 nm using VersaMax Microplate Reader (Molecular Devices LLC, San Jose, California, USA). The assays were performed in triplicate.

Clonogenic Assay:

MCF7 breast cancer cells were plated in 48-well plates, allowed to attach overnight and treated with 12.5, 25 or 50 nM of 1A3-VC-PAB-MMAE for 72 h. A vehicle treated well served as control. After removing the ADC-containing medium, cells were washed using PBS, trypsinized and plated at a density of 1000 cells/well in 12-well plates. The cells were cultured for 14 days, with fresh medium addition every 3 days. The colonies were stained with 0.5% crystal violet solution. The number of colonies per well was counted.

In Vivo Antitumor Activity Studies: The animal experiments were approved by the Institutional Animal Care and Use Committee of University of Wisconsin La Crosse (La Crosse, Wisconsin, USA). Four-week-old female NOD.Cg-Prkdc$^{scid}$ Il2rg$^{tm1Wjl}$/SzJ mice (NSG; The Jackson Laboratory) were acclimated for 1 week before the experiments. For MCF7 breast cancer xenograft model, the mice were implanted subcutaneously with 0.72-mg 17β-estradiol 90-day release tablets (Innovative Research of America) 3 days prior to cell injection. The endocrine-resistant MCF7-F xenograft model did not require 17β-estradiol pellets. Firefly luciferase expressing MCF7 and MCF7-F cells (2×10$^6$ cells in a 1:1 mixture of serum-free DMEM and Matrigel) were injected orthotopically into the fourth inguinal mammary fat pad of each mouse. Once the tumors were well established, each cell line cohort was divided into three groups (n=5). Mean tumor volume at the start of treatment was 111 mm$^3$ for the MCF7 cohorts and 119 mm$^3$ for the MCF7-F cohorts. The mice were treated by intraperitoneal injection every 4 days for a total of six doses with unconjugated or MMAE conjugated anti-cleaved-AREG 1A3 antibody (5 mg/kg), or vehicle control (PBS). Tumor volumes were calculated from caliper data by using the formula: Volume (mm$^3$)=(Length× Width$^2$)/2. Mice were imaged weekly with the in vivo FX PRO imaging system (Carestream Molecular Imaging, Woodbridge, CA, USA) after injecting luciferin (150 mg/kg body weight). Tumor volume and body weight were monitored once a week.

Statistical Analysis:

Statistical analyses were performed using Graph Pad Prism 7 (San Diego, CA, USA) software. Comparisons between groups were made using unpaired t-test (two groups) or one-way/two-way analysis of variance (three or more groups) with Bonferroni (for intergroup comparisons) or Dunnett's (when comparing relative to a single control) multiple comparison tests. Spearman's rank order coefficient correlation was used to analyze full length vs cleaved AREG IHC results. P values <0.05 were considered as significant and are indicated by asterisks in figures (**$P<0.0001$; *$P<0.001$; **$P<0.01$; *$P<0.05$).

RESULTS

Figure 1B:
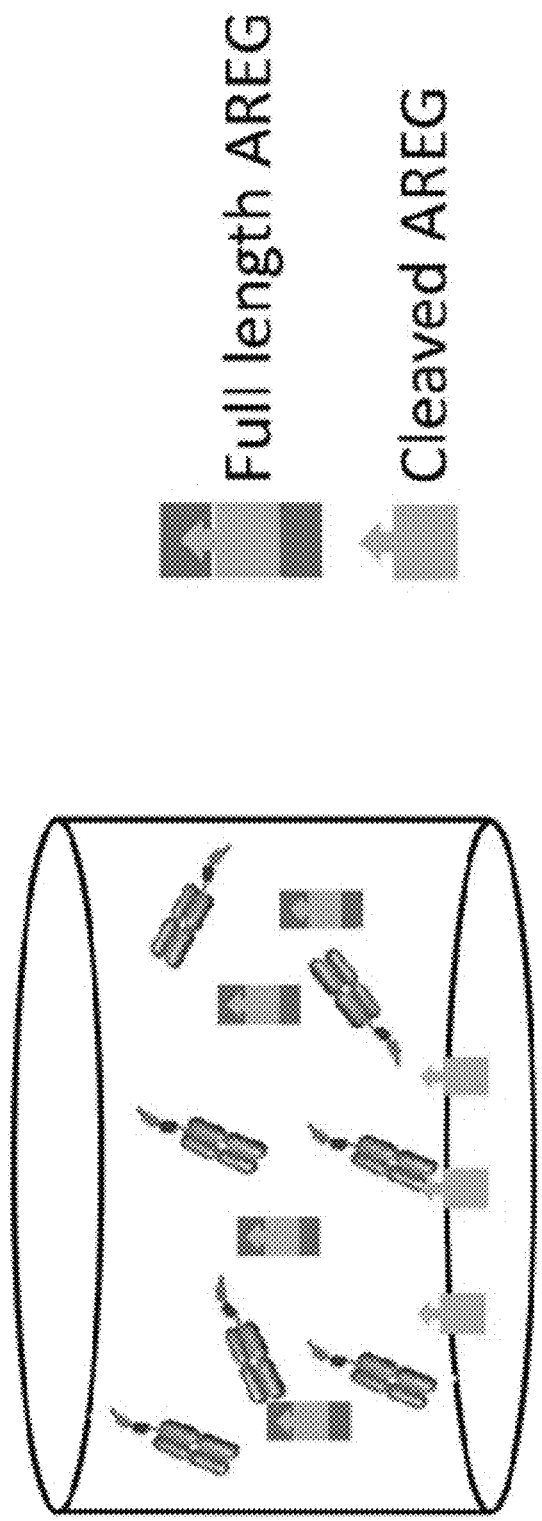
Figure 1C:
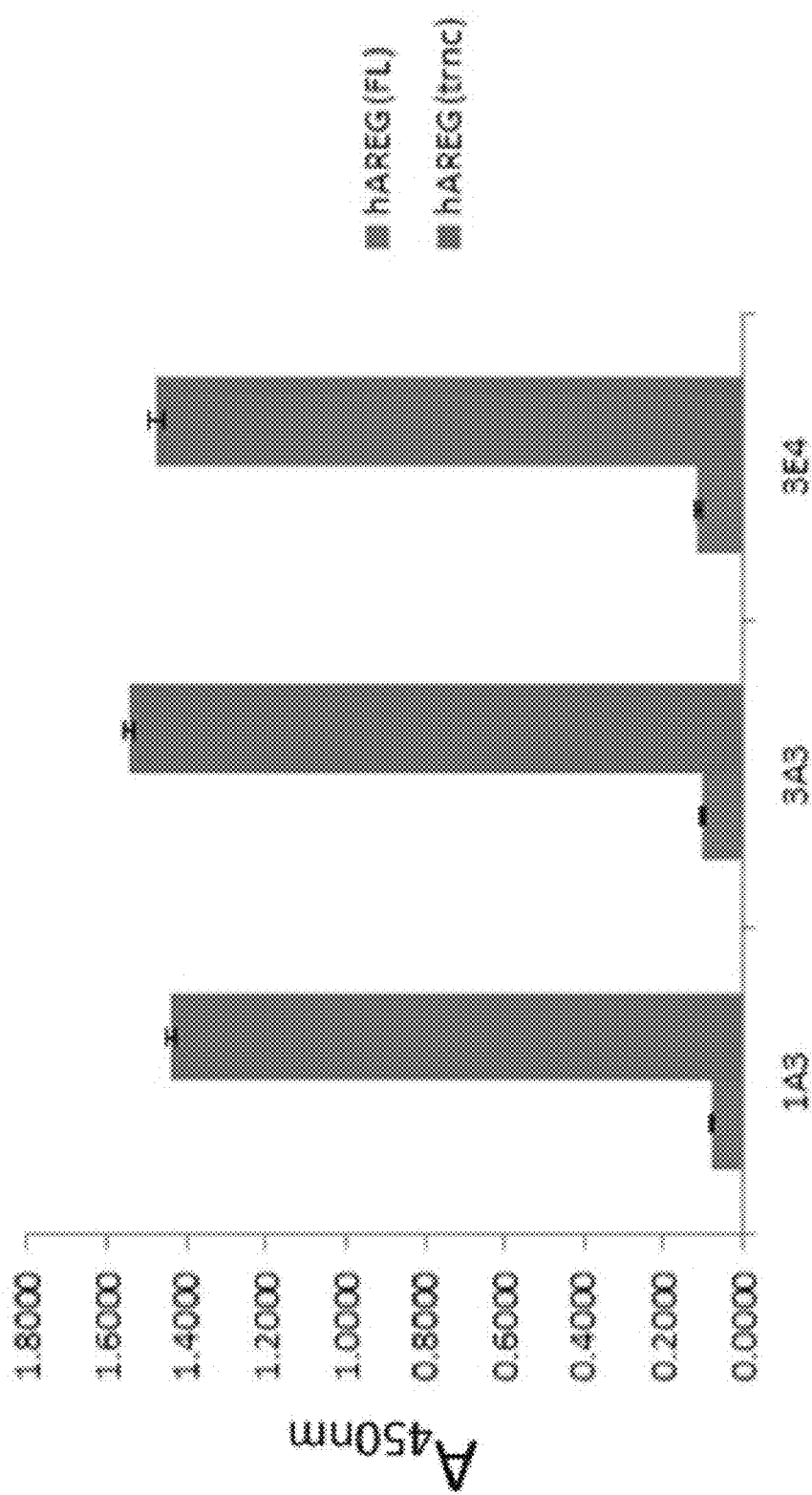
Figure 1D:
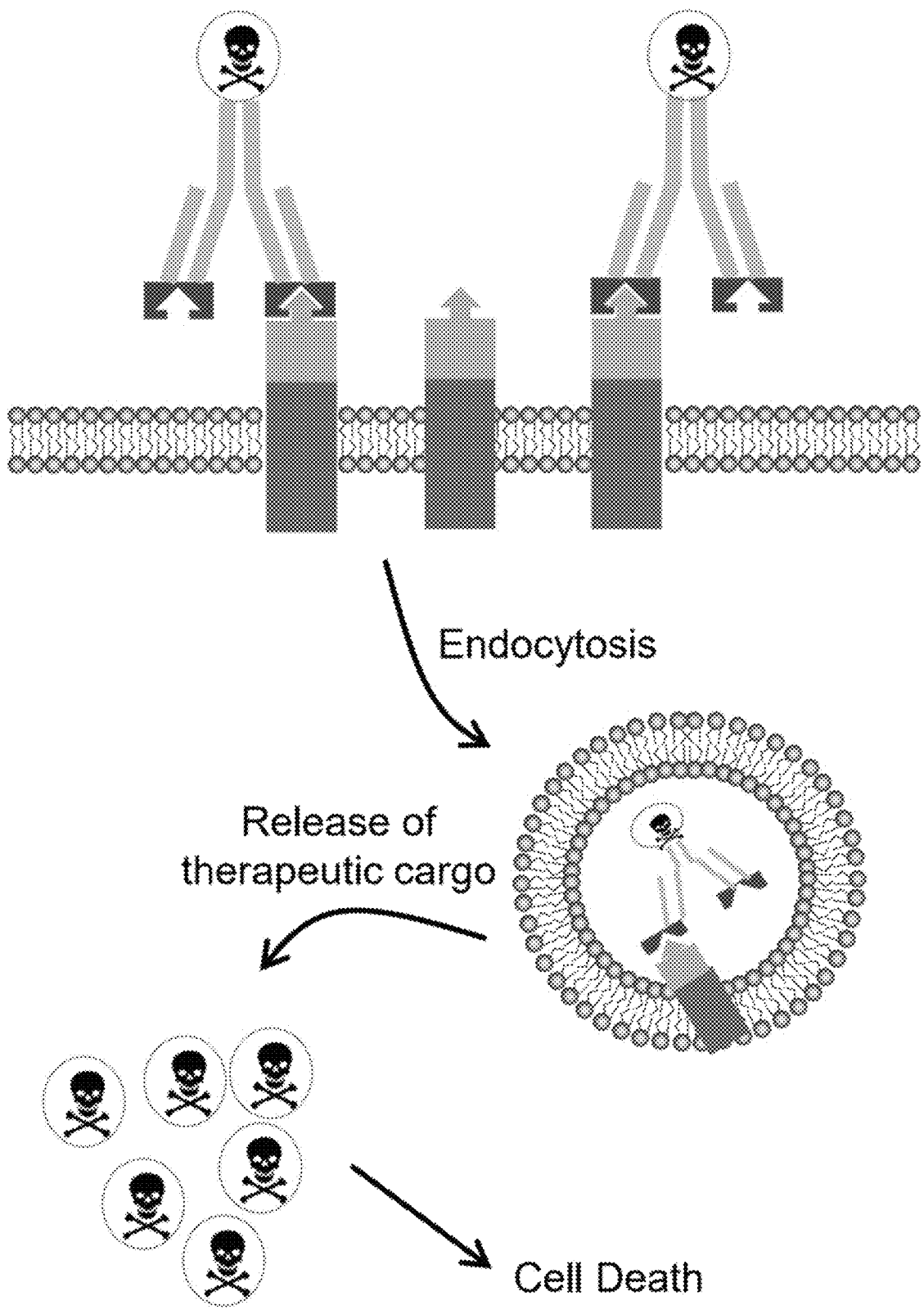

Candidate Antibody Identification:

The EGFR-activating signaling domain of AREG is inducibly released by ADAM17-mediated cleavage and the residual transmembrane stalk is internalized by endocytosis (FIG. 1A). We previously reported the N-terminal sequence of this residual transmembrane AREG fragment.[12] Reasoning that antibodies selectively recognizing this sequence in its cleaved but not uncleaved conformation might provide useful therapeutic reagents, we used phage display to isolate rabbit $V_K$-linker-$V_H$ scFVs with these binding characteristics (FIG. 1B). After IgG reformatting of the most favorable hits, we obtained three monoclonal rabbit IgG antibodies that selectively recognized a peptide representing the neo-epitope of the cell membrane-bound ADAM17-cleavage product of human AREG (FIG. 1C). We pursued further study with 1A3, the antibody which exhibited the highest binding ratio of cleaved AREG to intact AREG as determined by ELISA.

Figure 2A:
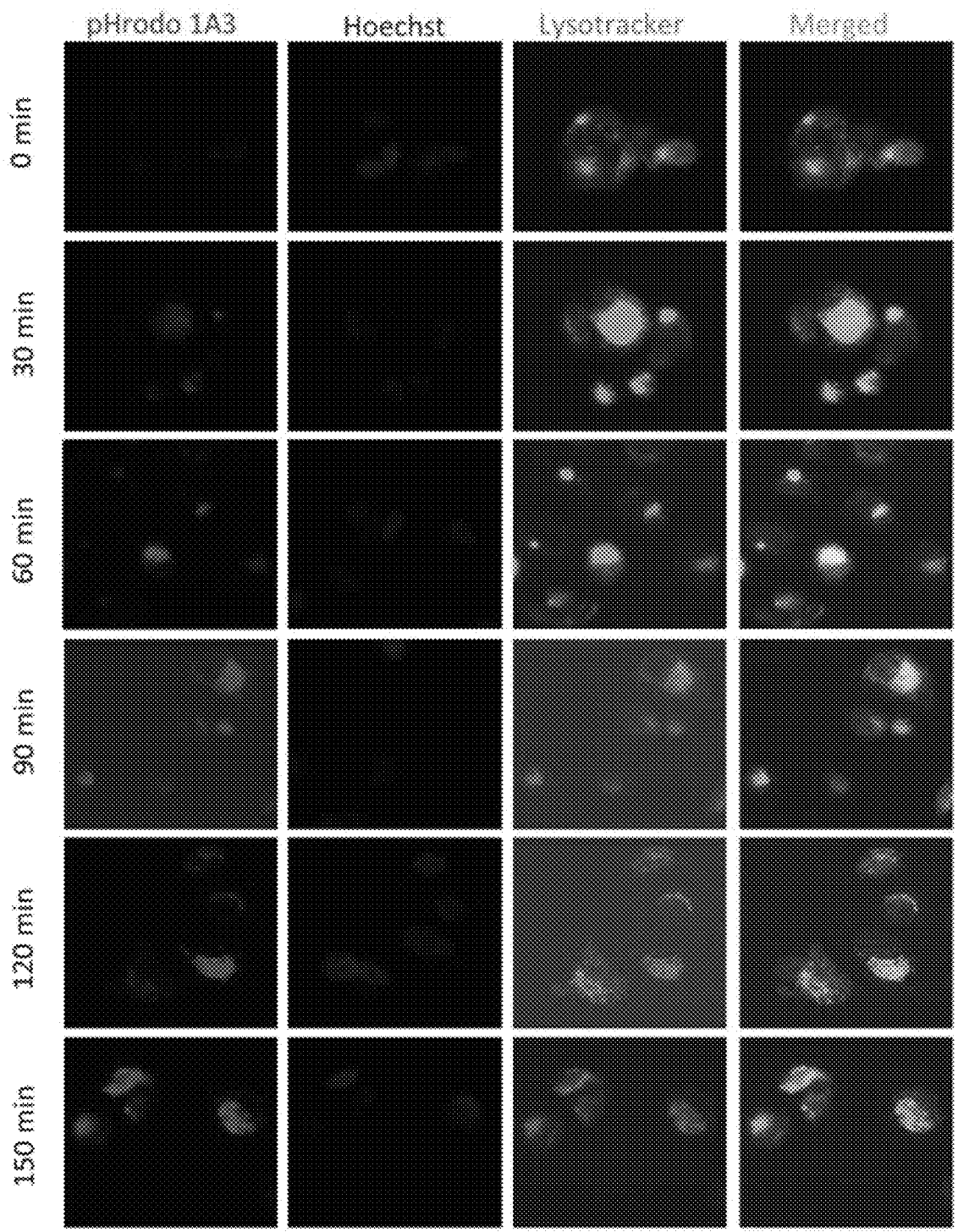
FIGS. 2A-2B. 1A3 recognizes the cleaved neo-epitope in its cellular context and can be used to internalize a fluorescent cargo.

Internalization of 1A3 Antibody is Dependent on AREG Cleavage:

Having demonstrated that the 1A3 antibody had the requisite selectivity profile against synthetic peptides (FIG. 1C), we then evaluated whether it could recognize endogenous cleaved AREG in its cellular context and, further, if it could be used to internalize a cargo. Conjugation with pHrodo, a dye that fluoresces in acidic environments, was used to evaluate both cell binding and internalization. We treated MCF7 cells with Hoechst and Lysotracker to visualize the nuclei and lysosomes, respectively, and then exposed them to 1A3-pHrodo. Red fluorescence, indicating the presence of 1A3 pHrodo in acidic endosomes, was evident after 30 min of 1A3-pHrodo treatment and increased in intensity over time (FIG. 2A). The colocalization of pHrodo and Lysotracker signals also increased throughout the time course, demonstrating that 1A3 was trafficked to the lysosome after internalization, a subcellular destination necessary for linker cleavage and release of the active drug.[14]

Figure 2B:
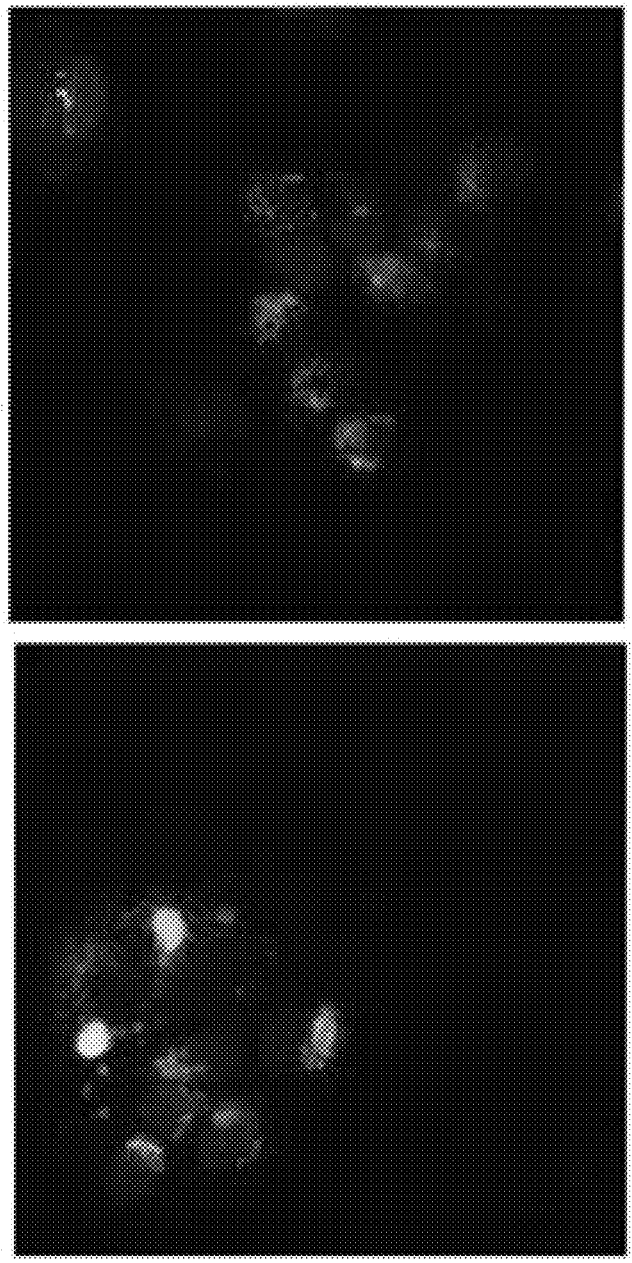

To determine whether ADAM17-mediated proteolytic generation of this neo-epitope was required for 1A3 internalization, we pretreated cells with the ADAM17 inhibitor, TAPI-2. This prevented the development of fluorescence after cells were incubated with 1A3-pHrodo treatment (FIG. 2B), from which we conclude that internalization of 1A3-pHrodo requires the generation of the neo-epitope by proteolytic cleavage.

Figure 3A:
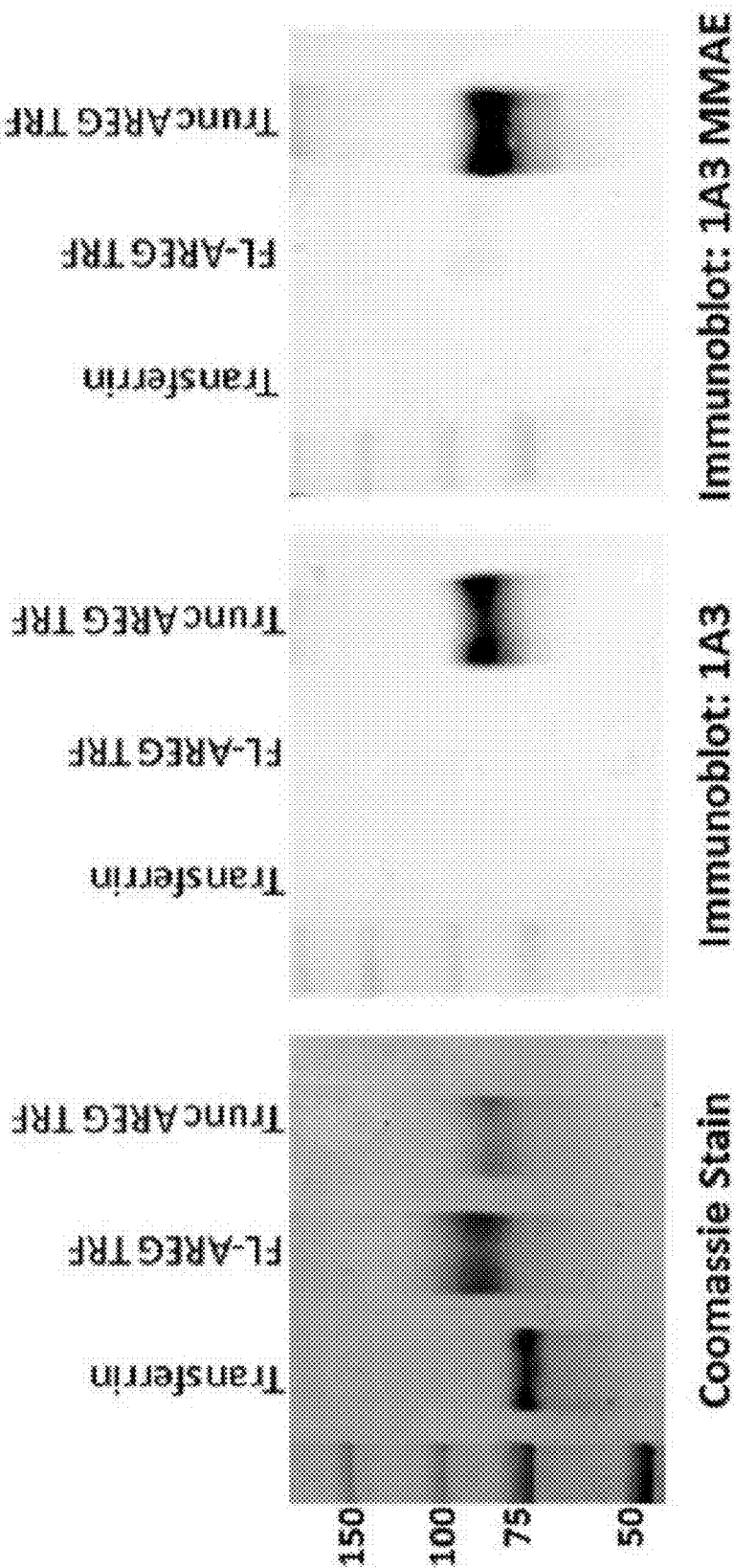
FIGS. 3A-3C. Conjugation of 1A3 with MMAE does not disrupt target recognition.
Figure 3B:
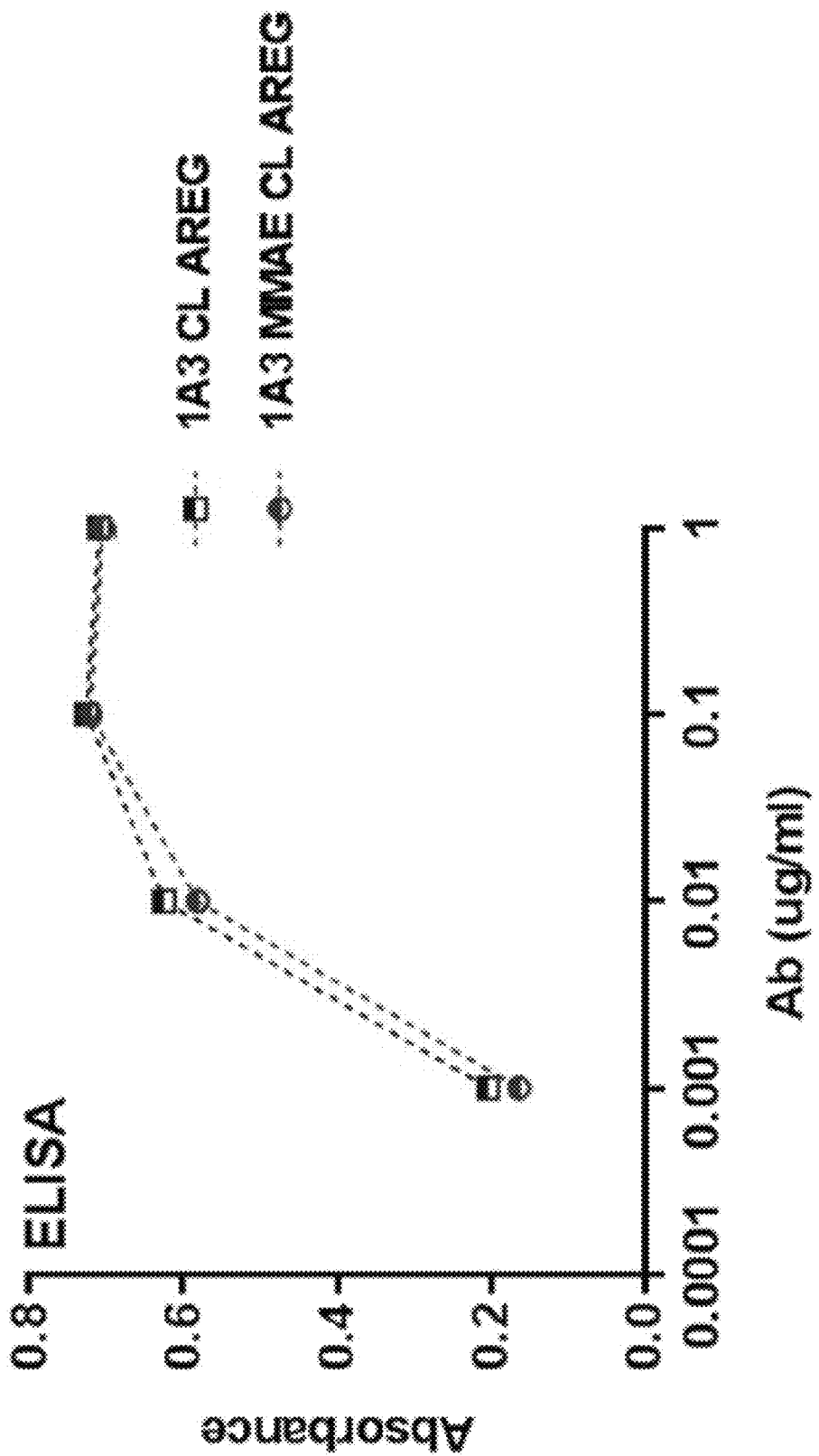
Figure 3C:
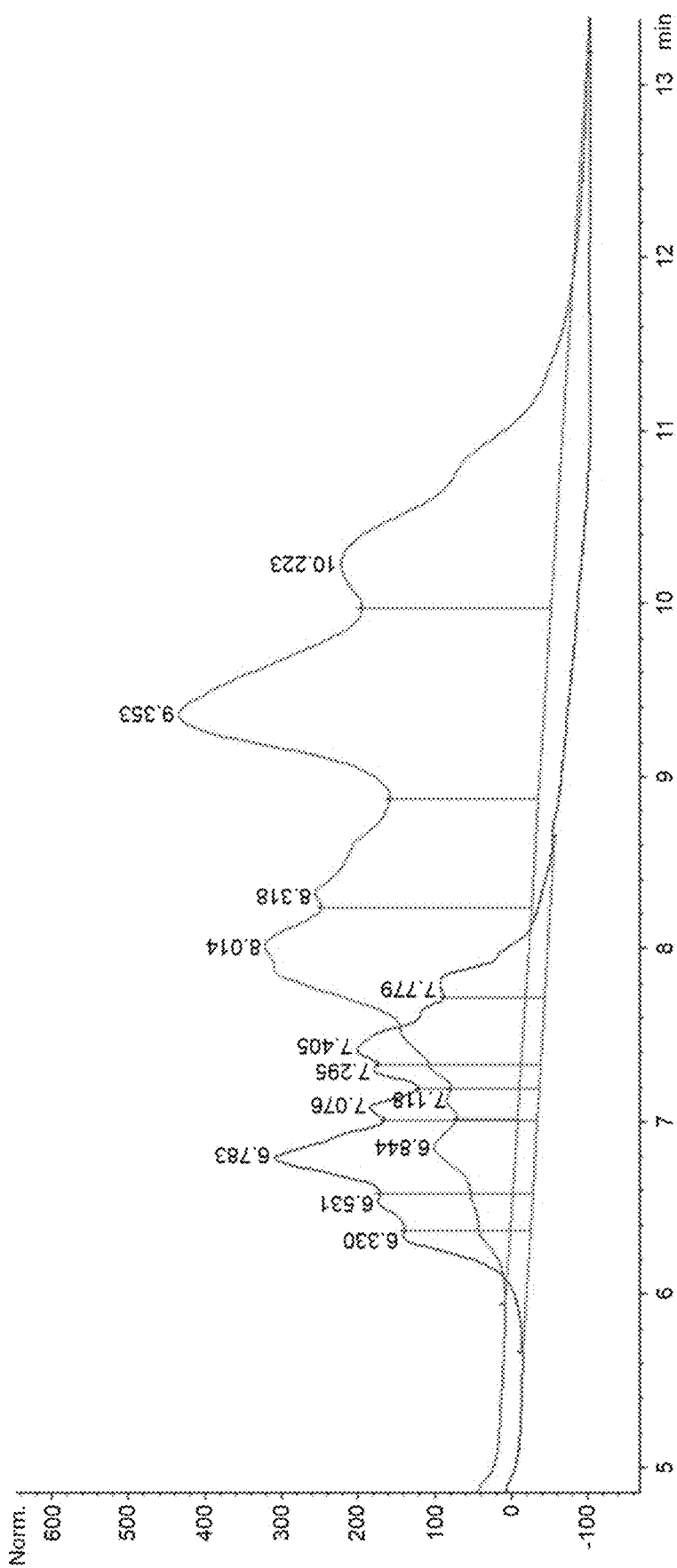

Retention of Epitope Selectivity Following MMAE Conjugation:

Using MMAE, we generated an ADC from 1A3 in order to assess the cytotoxicity in vitro and in vivo. To evaluate whether 1A3-MMAE retained the ability to selectively recognize the AREG neo-epitope after conjugation, immunoblots with 1A3 or 1A3-MMAE were performed with AREG peptides representing either an intact ADAM17-cleavage sequence (FL AREG) or the fragment that remains cell-bound after cleavage by ADAM17 (Trunc AREG). Both 1A3 and 1A3-MMAE specifically recognized the truncated AREG and also, did not react with the peptide representing uncleaved AREG (FIG. 3A). A capture ELISA using the cleaved AREG peptide also exhibited no substantial difference in binding between the unconjugated 1A3 and 1A3-MMAE (FIG. 3B). HIC-HPLC (FIG. 3C) of 1A3-MMAE (red) exhibited increased retention time relative to the unconjugated 1A3 (blue). Based on the ultraviolet light absorbance ratio (A248/A280) of the 1A3-MMAE antibody (0.715) and the equation derived by Hamblett et al.,[15] the estimated drug antibody ratio (DAR) was 3.98. This placed our ADC within the range of several previously investigated ADCs with DARS between 2 and 6 that was strikes a balance between ADC solubility with an effective degree of payload delivery.[15-18]

Figure 4A:
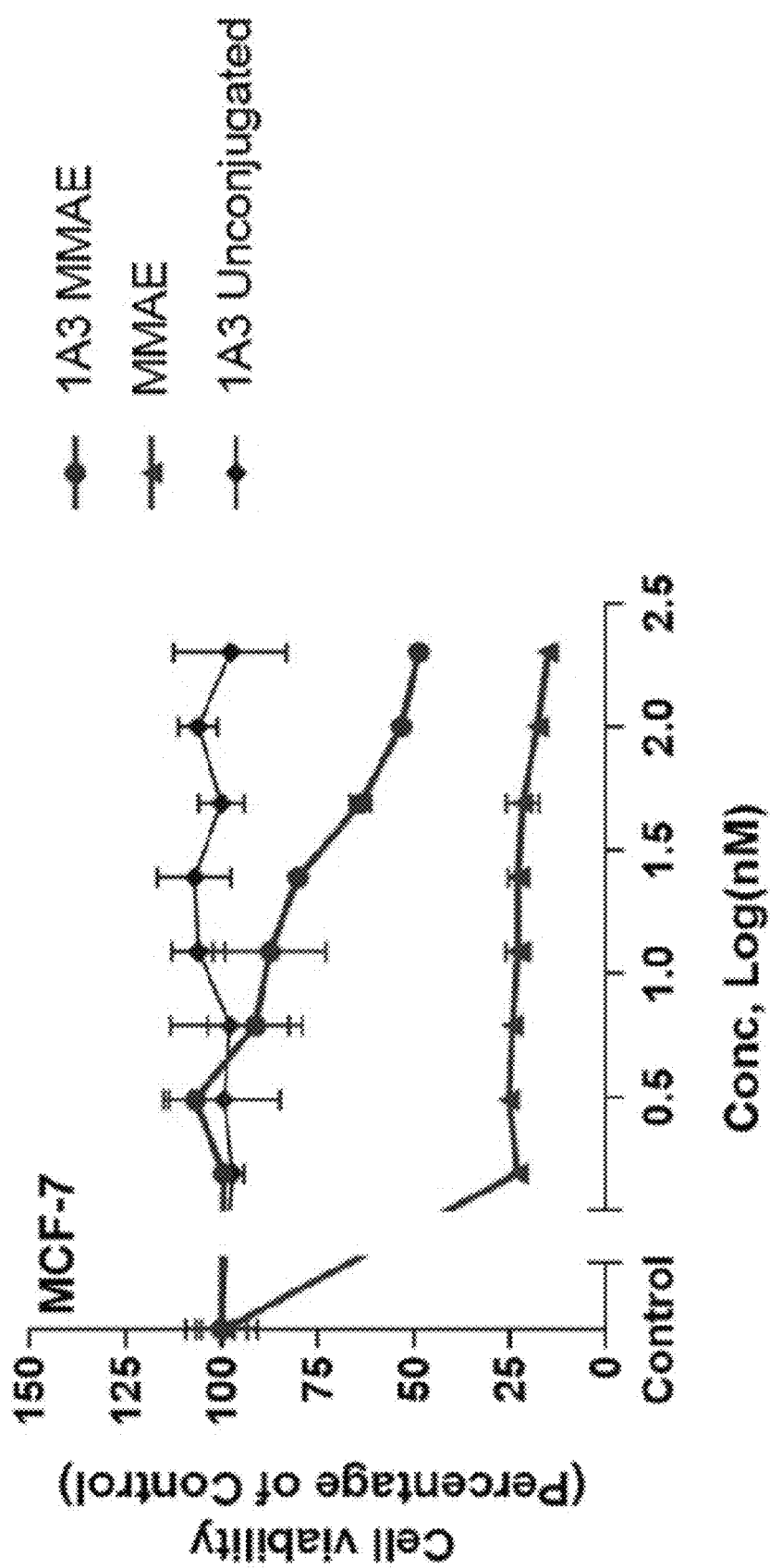
FIGS. 4A-4E. In vitro 1A3-MMAE cytotoxicity in MCF-7 (FIG. 4A) and MCF-7F (FIG. 4B) cells measured by MTT assay after treatment with 1A3-MMAE, 1A3 or MMAE.
Figure 4B:
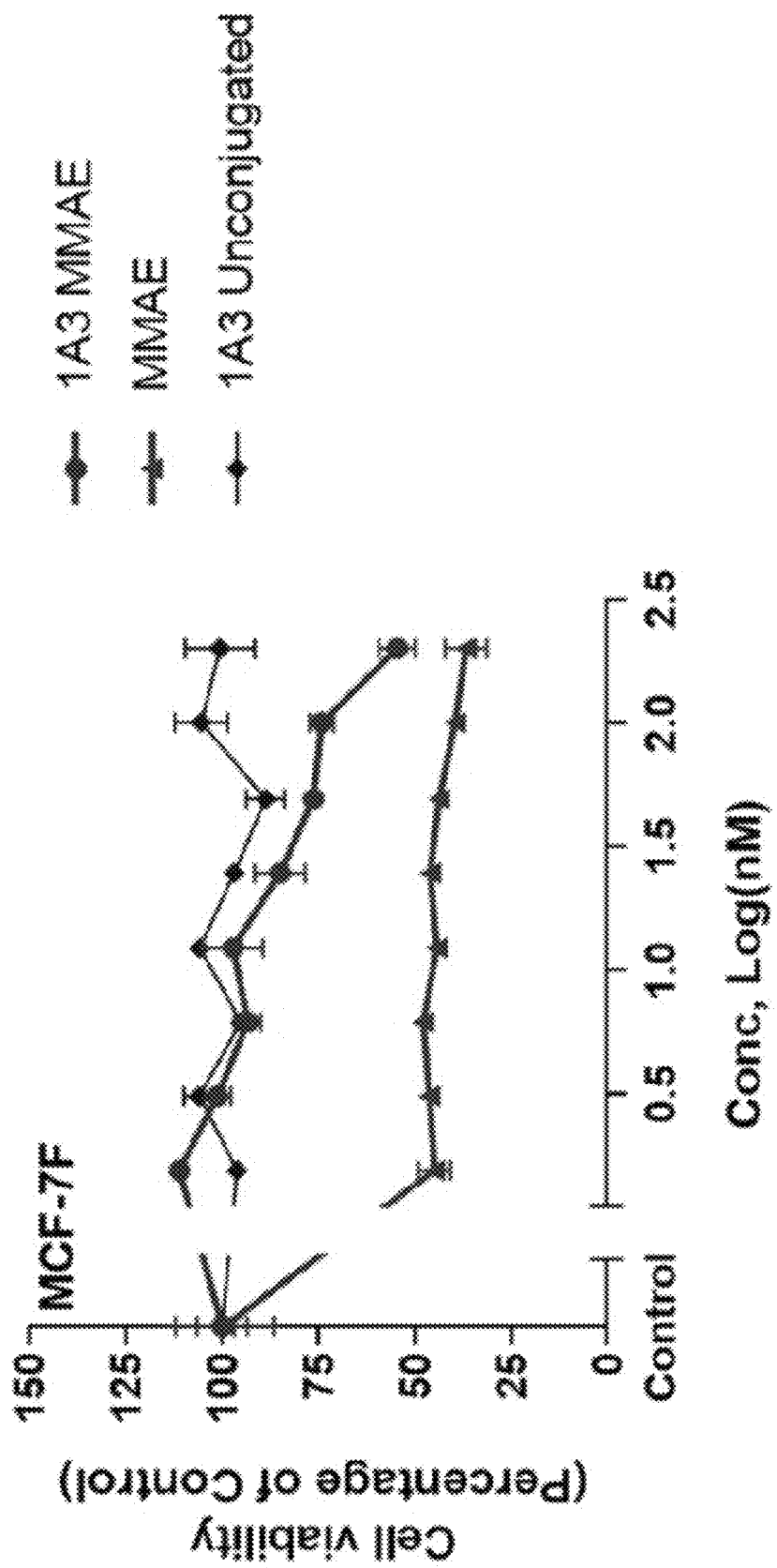
Figure 4C:
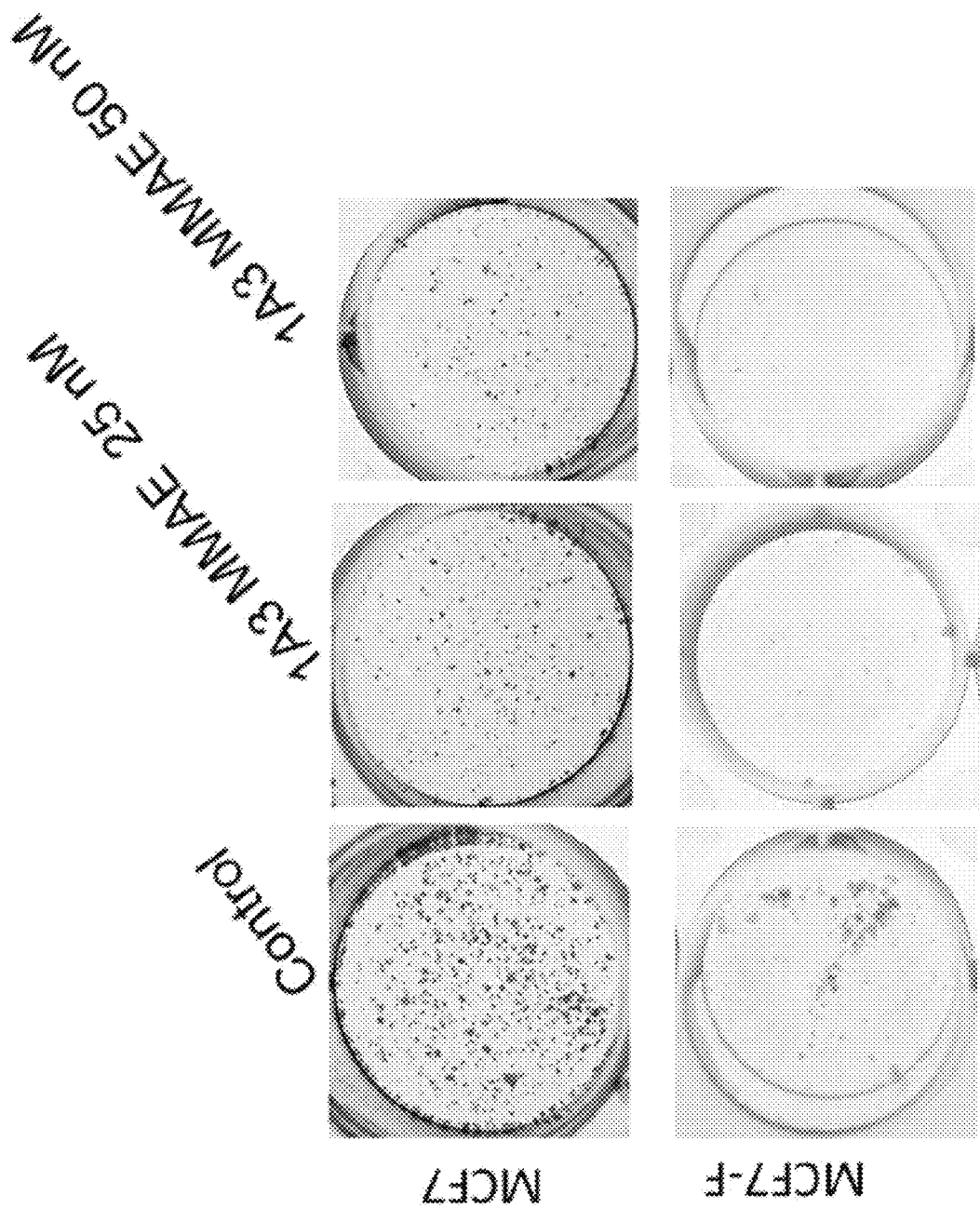
Figure 4D:
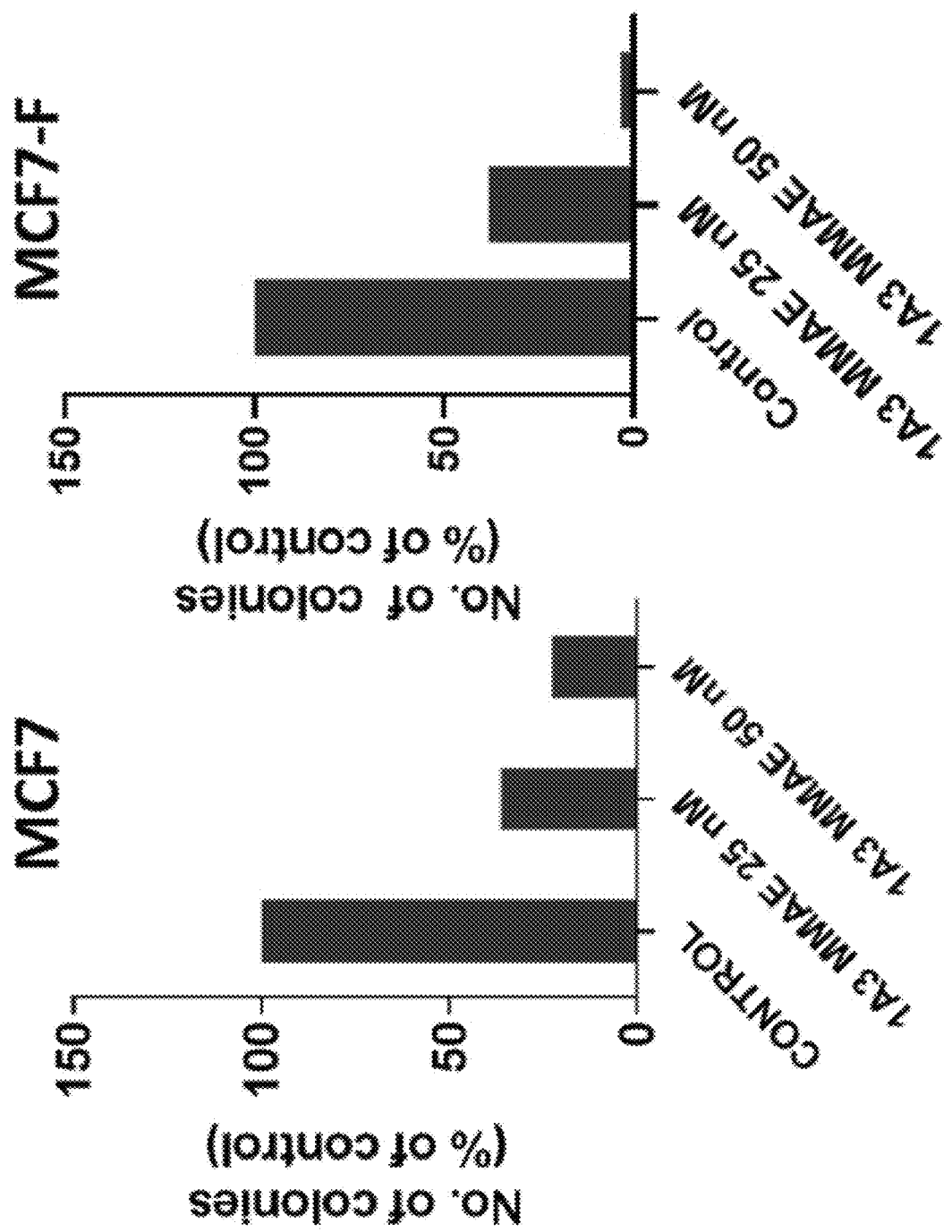
Figure 4E:
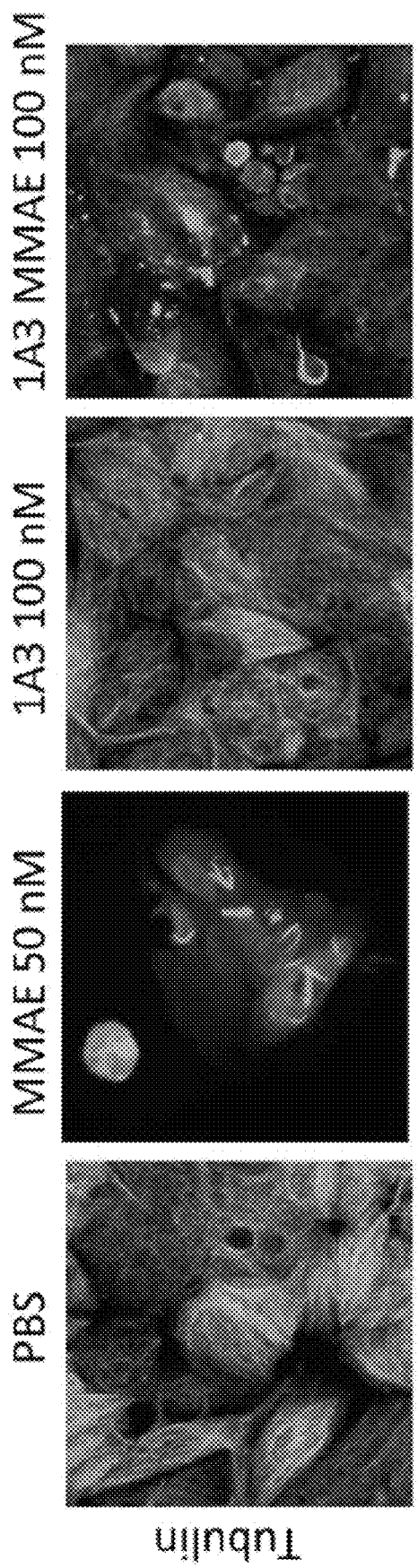

1A3-MMAE is Cytotoxic in Breast Cancer Cell Lines:

Treating MCF7 and Fulvestrant-resistant MCF7 (MCF7-F) with 1A3-MMAE resulted in considerable cytotoxicity, as measured by MTT assay (FIGS. 4A and 4B). Importantly, unconjugated 1A3 did not induce cell death, whereas free MMAE potently killed the cells. Clonogenic assays with 25 or 50 nM 1A3-MMAE also showed a dose-dependent effect on survival in both MCF7 and MCF7-F cell lines visually (FIG. 4C) and when quantified as number of colonies relative to the control (FIG. 4D). As MMAE acts to prevent tubulin polymerization, we evaluated microtubule integrity in cells exposed to 1A3-MMAE. Cells that received free MMAE or 1A3-MMAE exhibited tubulin disruption, whereas control treatments with PBS, unconjugated 1A3 or IgG-MMAE did not (FIG. 4E).

Figure 5A:
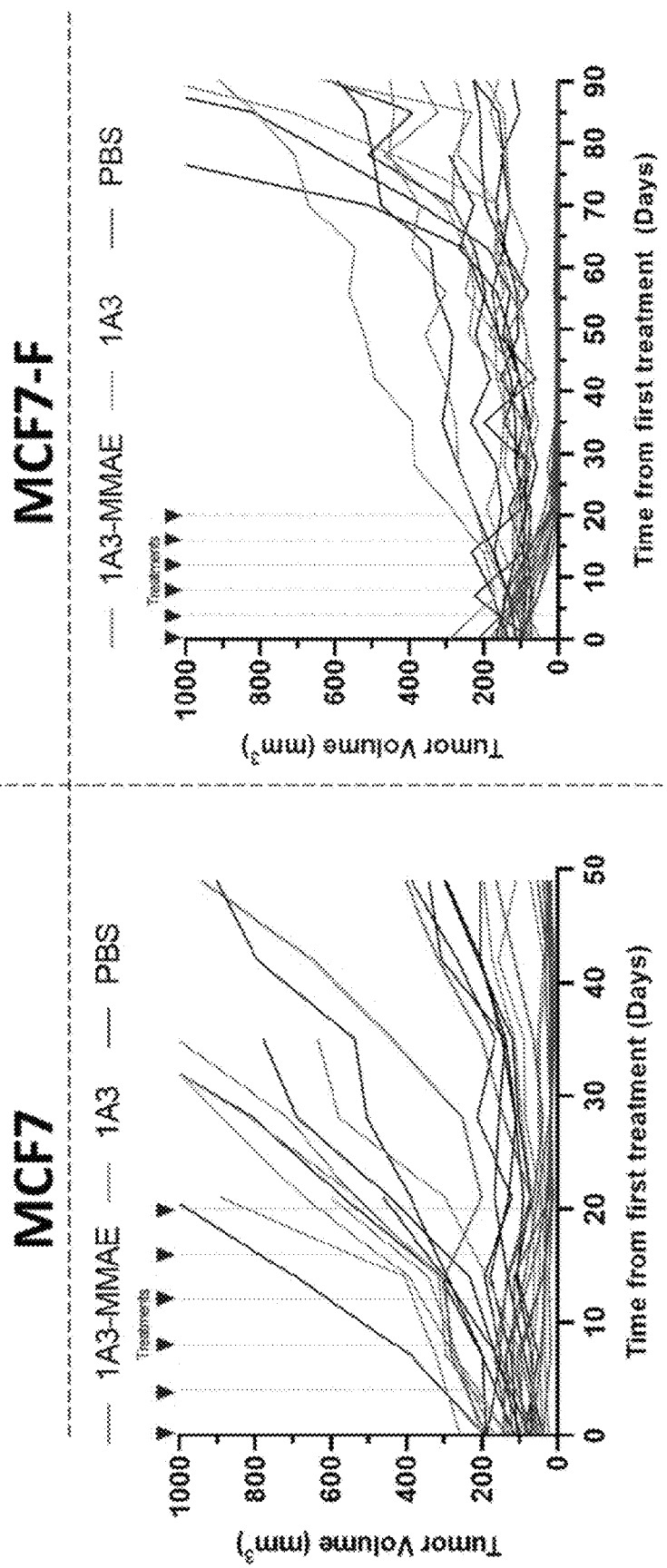
FIGS. 5A-5C. In vivo anti-tumor efficacy in MCF7 and MCF7-F cell lines.
Figure 5B:
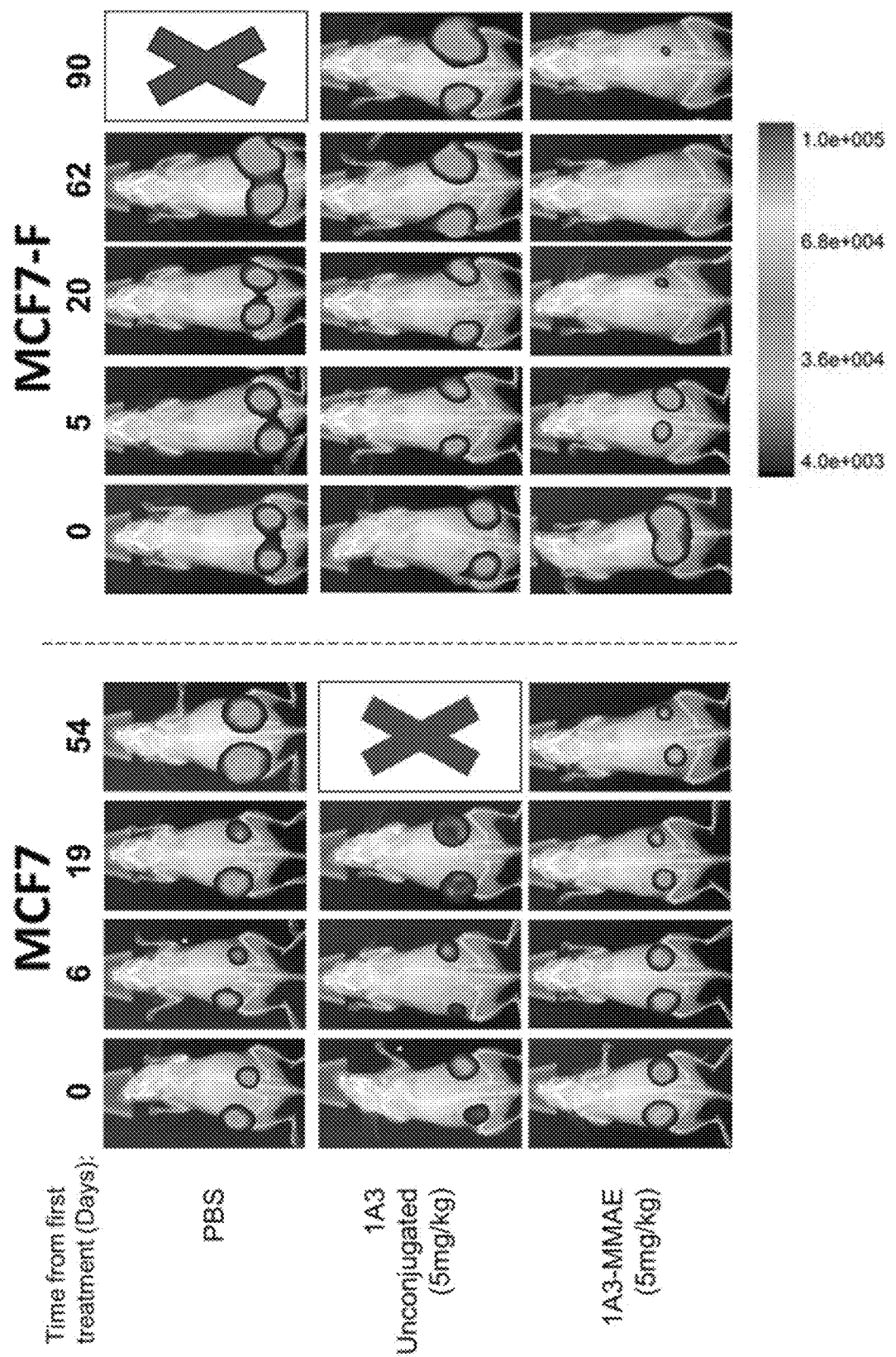

1A3-MMAE Treatment Causes Regression of Breast Cancer Xenografts:

To test in vivo efficacy of 1A3-MMAE, human breast cancer cell lines expressing luciferase were injected orthotopically into NSG mice (one tumor in each inguinal mammary gland). Once the average tumor size reached approximately 100-125 mm³, mice were randomized to one of three treatment groups: PBS, 1A3 (5 mg/kg) or 1A3-MMAE (5 mg/kg). Mice received intraperitoneal injections every 4 days for six total injections and were monitored for tumor progression or regression. Similar experiments were performed with MCF7 (FIGS. 5A, 5B, and 5C, left panels) and MCF7-F (FIGS. 5A, 5B, and 5C, right panels) xenografts. For both cell lines, caliper measurements demonstrated strong tumor shrinkage in response to 5 mg/kg 1A3-MMAE (FIG. 5A). Neither the PBS nor unconjugated 1A3 treated groups showed a disruption in tumor growth with continued, sometimes rapid increases in tumor volume relative to the 1A3-MMAE group.

Longitudinal luciferase imaging of established xenografts and their response to treatments (FIG. 5B) showed changes in tumor size that matched volume trends seen with caliper measurements. One representative animal is shown from each cell line and treatment group. The PBS and unconjugated 1A3 groups exhibited tumor growth evident by increased lesion diameter and increasing signal intensity (color change). In contrast, tumors in the 1A3-MMAE treated groups both decreased in both volume and signal. Notably, in the MCF7-F/1A3-MMAE image, one can see the tumor signal decreasing below the limit of detection for imaging, and with continued follow-up, 70 days after the end of dosing, the re-appearance of a lesion.

Figure 5C:
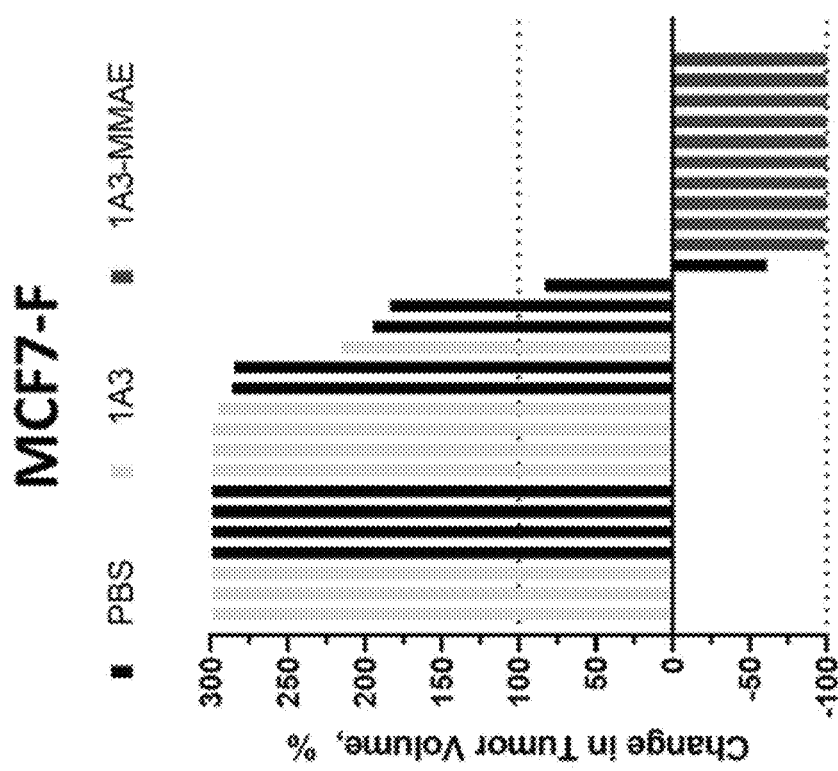
Figure 5C:
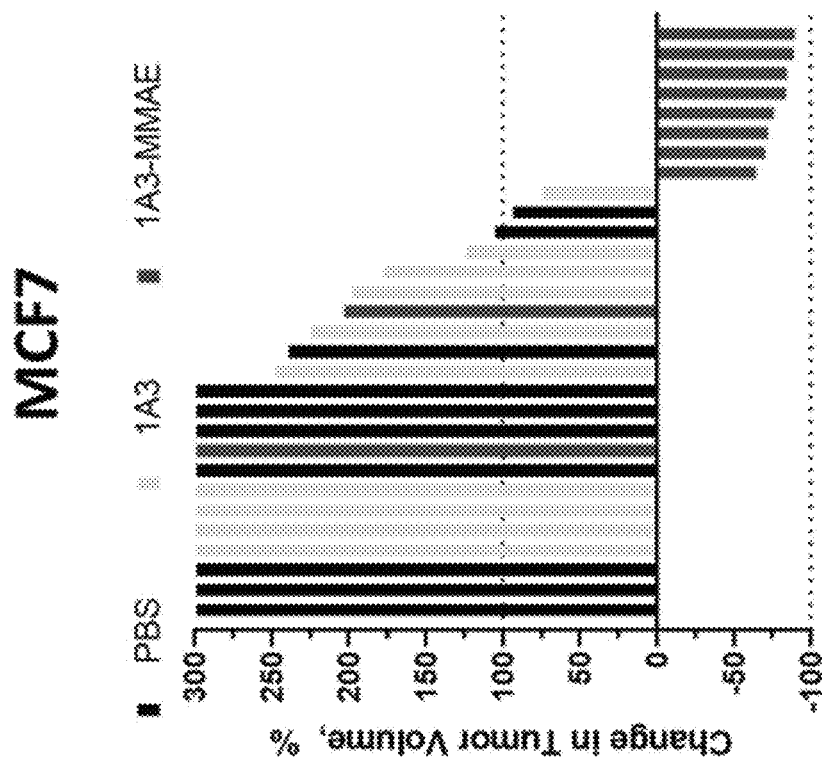

To evaluate overall efficacy, we determined the maximum response as defined by the maximum change in tumor volume relative to pre-treatment measurements, depicted as waterfall plots for MCF7 and MCF7-F (FIG. 5C). Of the MCF7 xenografts, tumor volume increased in 2/10 and decreased in 8/10 dosed with 5 mg/kg 1A3-MMAE. As the 5 mg/kg dose of 1A3-MMAE successfully cleared the tumors to sub-detectable levels in all 10 of the MCF7-F xenografts, we continued follow-up in this cohort to determine whether this was curative or if recurrence was possible. After a 204-day follow-up period, 10/10 tumors had recurred in mice treated with 5 mg/kg 1A3-MMAE; however, only one tumor treated with 1A3-MMAE returned to a size seen prior to treatment, with an average time to recurrence of 73 days after initial tumor clearance determined by luciferase imaging.

Figure 6A:
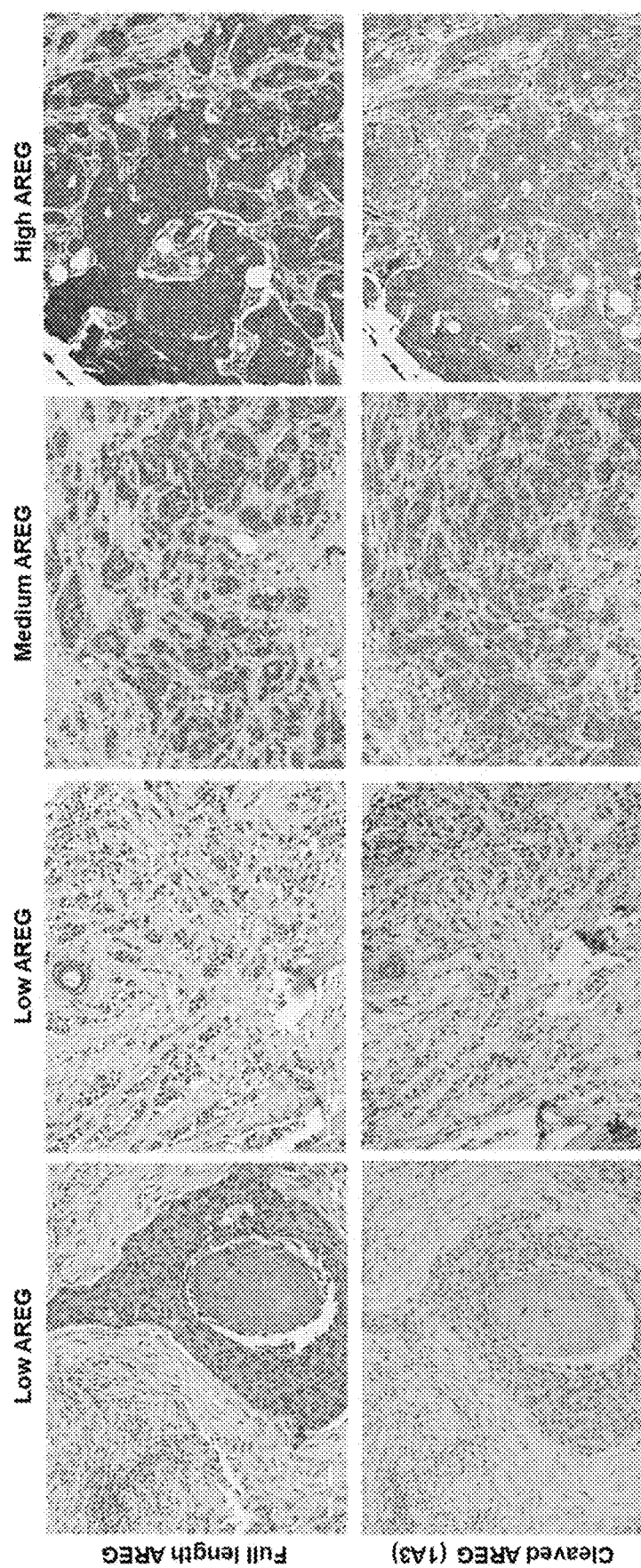
FIGS. 6A-6B. Evaluation of 1A3 antibody utility as a companion diagnostic.
Figure 6B:
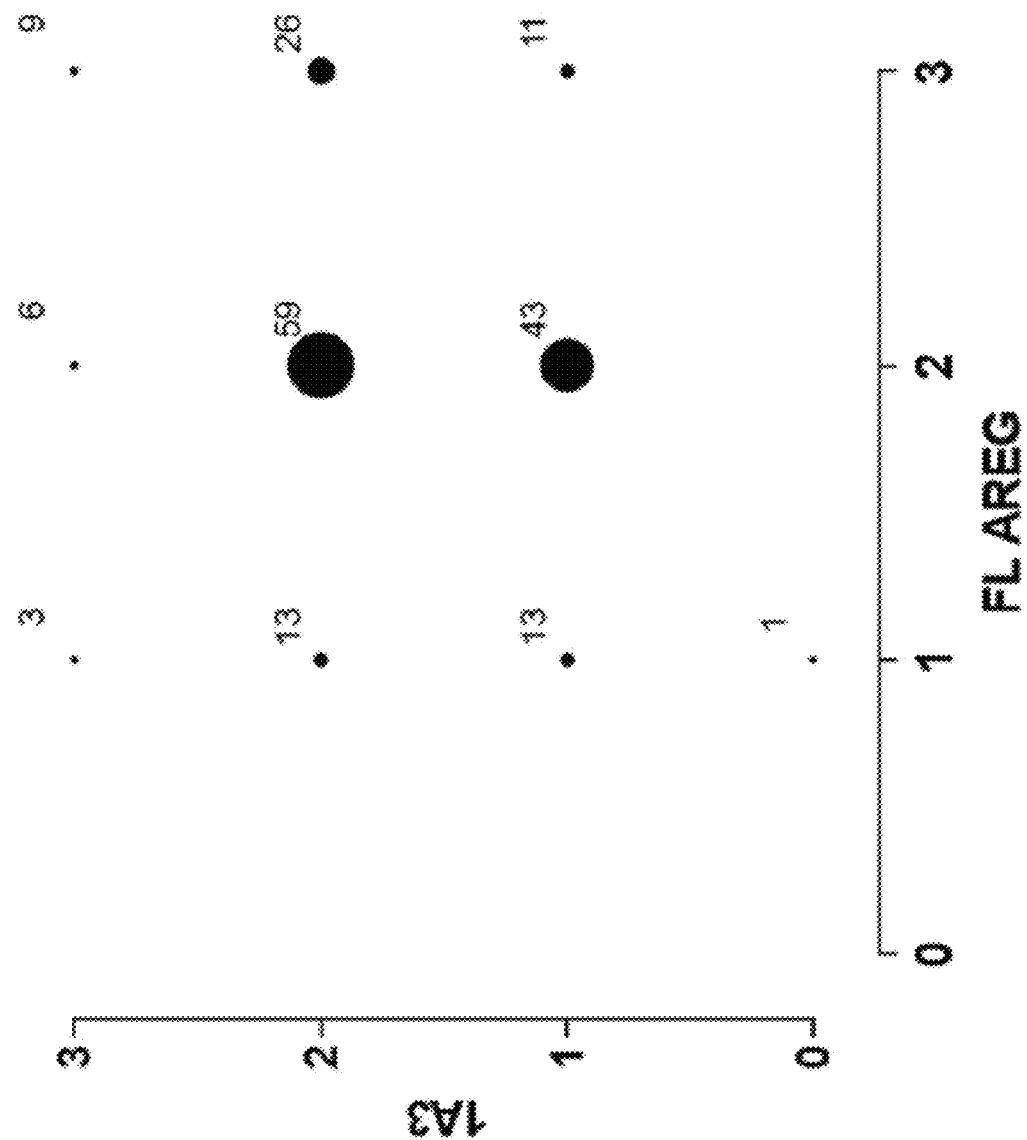

Evaluation of 1A3 Utility as a Companion Diagnostic:

We performed immunohistochemistry on a breast tumor tissue micro-array to obtain an estimate of the prevalence of the target in breast cancer and to determine whether 1A3 staining can be used as a treatment selection biomarker. In general, samples with high AREG expression usually exhibited high-cleaved AREG intensity (FIGS. 6A and 6B). This indicates that (1) AREG-high tumors generally actively cleave AREG, (2) the recycling kinetics in tumors are not so rapid as to preclude detection of the epitope by these antibodies and (3) these antibodies may have additional utility as companion diagnostics. Among ER-positive (n=88) and ER-negative (n=50) tumors evaluated, the proportions of tumors exhibiting medium/high intensity staining with 1A3 were essentially equivalent (69.3% v 70%, respectively). Although it has been previously reported that AREG tends to be more highly expressed in ER-positive breast tumors,[6] there is clearly a substantial fraction of ER-negative tumors which express and cleave AREG in sufficient quantities to be considered therapeutic candidates.

DISCUSSION

In this Example, we establish that the cell-associated transmembrane stalk of AREG that is generated by ADAM17-mediated cleavage is a viable therapeutic target in breast cancer. We identified three rabbit monoclonal antibodies that very selectively recognized this neo-epitope after cleavage, and which did not interact with full-length (FL) AREG. In vitro and in vivo experiments demonstrated anti-tumor efficacy of MMAE-ADCs. In all experiments, the naked antibody was ineffective, demonstrating that it is the target-mediated MMAE internalization that underlines the therapeutic effect. This Example establishes that antibodies with this target recognition profile may have anti-cancer utility, but further engineering to incorporate human sequences would be required to recruit the full range of effector functions in humans and prevent likely anti-rabbit immune responses against the ADC itself.[19]

Identifying an appropriate target antigen is critical for efficacy and tolerability of ADC dosing in patients; ideally one would choose a tumor-specific antigen rather than a tumor-associated antigen to decrease the likelihood of on-target, off-tumor effects. Here, by demonstrating the feasibility of designing an ADC against a transient protein cleavage product, this Example suggests that developing ADCs against targets that display different epitopes in some manner dependent on their state of activation/processing may generally provide even more selective ways to target relevant cell populations in vivo.

Our two series of in vivo experiments differed in one important respect. MCF7 growth required supplementation with slow-release estrogen pellets, whereas the endocrine-resistant MCF7-F cell line grows independently of estrogen and these animals were not supplemented. Although both groups of tumors responded well to 1A3-MMAE, the MCF7-F tumors experienced more pronounced responses. Whether this can be explained by the difference in hormonal milieu, a greater dependence on AREG in this endocrine-resistant cell line or some other reason is unclear. Nevertheless, the strong response observed in the endocrine-resistant line suggests that these ADCs may warrant evaluation in this patient population for whom there are fewer effective treatments available.

Another anti-AREG therapeutic antibody strategy was recently reported[20] in which antibodies recognizing the shed AREG signaling domain can be used to stoichiometrically bind and sequester AREG released by ovarian cancer cells, thereby blocking autocrine signaling. The approach outlined in this Example has the advantage of directly killing the AREG releasing cells; however, given that off-target toxicities with an ADC (if they occur) are likely to be more severe, this Example offers a useful alternative strategy for targeting AREG, as well as establishing ovarian cancer as another malignancy in which this EGFR ligand may play an important role.

An appropriate companion diagnostic is critical to the successful development of a targeted therapeutic. We have shown that the 1A3 antibody efficiently detects cleaved AREG in formalin-fixed, paraffin-embedded breast cancer specimens (FIGS. 6A and 6B). Importantly, this series demonstrated that while cleaved AREG is quite commonly expressed in ER+ tumors, it is also found in ER− tumors. Accordingly, although our experimental focus has been on ER+/AREG+ breast tumors, given broader expression of AREG in breast tumors (FIGS. 6A and 6B) and in both HER2-amplified[21] and non-amplified[4] ER-negative breast cancer cell lines, the utility may extend to ER−/AREG+ tumors or, indeed, to AREG-high tumors in other tissue types.[9]

In conclusion, this Example demonstrates the feasibility of generating selective ADCs against transient neo-epitopes generated by post-translational processes like proteolytic cleavage. We present a novel anti-AREG ADC with utility in breast cancer treatment.

Example 2

SUMMARY

Amphiregulin (AREG) is a transmembrane protein which, following TACE/ADAM17-dependent cleavage, releases a soluble Epidermal Growth Factor Receptor ligand domain that promotes proliferation of normal and malignant cells. Expression of Amphiregulin has been described by immunohistochemistry in several tumor types, including lung, prostate, head and neck, gastric, pancreatic and breast cancers but evidence for a functional requirement for Amphiregulin in these malignancies is more limited. In Example, 1, we described the development of a monoclonal antibody, GMF-1A3, that selectively recognizes the Amphiregulin epitope that is revealed following cleavage by TACE/ADAM17 and demonstrated that drug conjugates of this antibody have anti-tumor activity in mouse models. By directly evaluating Amphiregulin cleavage, immunohistochemistry on tissue specimens using this antibody can be used to evaluate the extent to which Amphiregulin is being proteolytically processed in cancer, which is a more direct measure of Amphiregulin activity. As a potential companion diagnostic for this antibody-drug conjugate, this immunohistochemistry assay allows identification of tumors with high levels of the cleaved Amphiregulin target. In this Example, we evaluate levels of cleaved Amphiregulin in 370 specimens from 10 tumor types and demonstrate that it is widely expressed in solid tumors and is especially common (more than 50% of cases) in breast, prostate, liver and lung cancer.

BACKGROUND

Amphiregulin (AREG) is a transmembrane protein which, following TACE/ADAM17-dependent cleavage,[3] releases a soluble EGFR ligand domain which promotes proliferation of normal and malignant cells. This proteolysis event leaves a residual cell-surface transmembrane stalk which is subsequently internalized. We previously determined the N-terminal sequence of this cell associated Amphiregulin cleavage product[12] and in Example 1, we generated antibodies that selectively recognize this epitope in its cleaved but not its intact conformation. The antibodies are internalized by cultured cells in a cleaved Amphiregulin dependent manner. We have developed one of these antibodies into an MMAE-based antibody drug conjugate, GMF-1A3, and demonstrated that it can kill human breast cancer cells in vitro and as xenografts in immunocompromised mice.

Appropriate selection of patients for targeted cancer treatment typically relies on some kind of companion diagnostic to identify the sub-population of patients whose tumors are most likely to respond. An initial evaluation of our GMF-1A3 antibody as an immunohistochemical companion diagnostic was performed in 138 breast cancer specimens. We found medium/high immunoreactivity in 70% of cases. While our initial drug development focus has been on Amphiregulin in breast cancer, it is expressed in several other cancer types,[9] so the utility of therapeutic antibody drug conjugates likely extends to other malignancies. While the expression of Amphiregulin in these other tissues has been described, the extent to which cleaved Amphiregulin is present at sufficient abundance to represent a viable target for the GMF-1A3-MMAE antibody drug conjugate is unknown. To address this issue, in this Example, we evaluated the levels of cleaved Amphiregulin in tissue microarrays comprised of 370 specimens from a total of 10 tumor types.

Materials and Methods

Immunohistochemistry:

Two multiple organ carcinoma tissue microarrays were purchased from BioCoreUSA (Philadelphia, PA, USA). The slides were deparaffinized in xylene and rehydrated by serial incubations in graded ethanol and then in water in a Histo-Tek® SL Slide Stainer (Sakura Finetek USA, Inc., Torrance, CA, USA). Antigen retrieval was performed in a steamer by boiling slides in a container of citrate buffer (pH 6.0) for 20 min which was then removed for 15 minutes of cooling on the benchtop. Slides were washed in 1× Wash buffer (Dako Agilent, Santa Clara, CA, USA) and endogenous peroxidase was quenched by incubating with Dako Dual Endogenous Enzyme Block for 10 minutes. Slides were washed in 1× Wash buffer, blocked (5% rabbit/10% goat serum in PBS), and immunostained with goat anti-AREG antibody (15 µg/mL; AF262, R&D Systems) or rabbit anti-cleaved AREG 1A3 antibody (10 µg/mL) overnight at 4° C. Slides were washed four times in 1× Wash buffer, followed by incubation for 45 minutes at room temperature in 1:100 dilution of rabbit anti-goat immunoglobulins/HRP or ready-to-use goat antirabbit HRP labelled polymer (Dako). The slides were washed twice in 1× Wash buffer and the color was developed with 3,3-diaminobenzidine tetrahydrochloride (DAB) substrate chromogen system (DAKO). Sections were washed with water and counterstained with hematoxylin, rinsed with water, dehydrated by serial ethanol washes to 100%, cleared, and mounted in Permount (Thermo Fisher Scientific). The staining intensity was assessed semi-quantitatively using a four-point scale (Negative=0, Low=1, Medium=2, High=3) by two investigators working independently on blinded samples. Discordant scores were resolved by joint review.

Figure 7A:
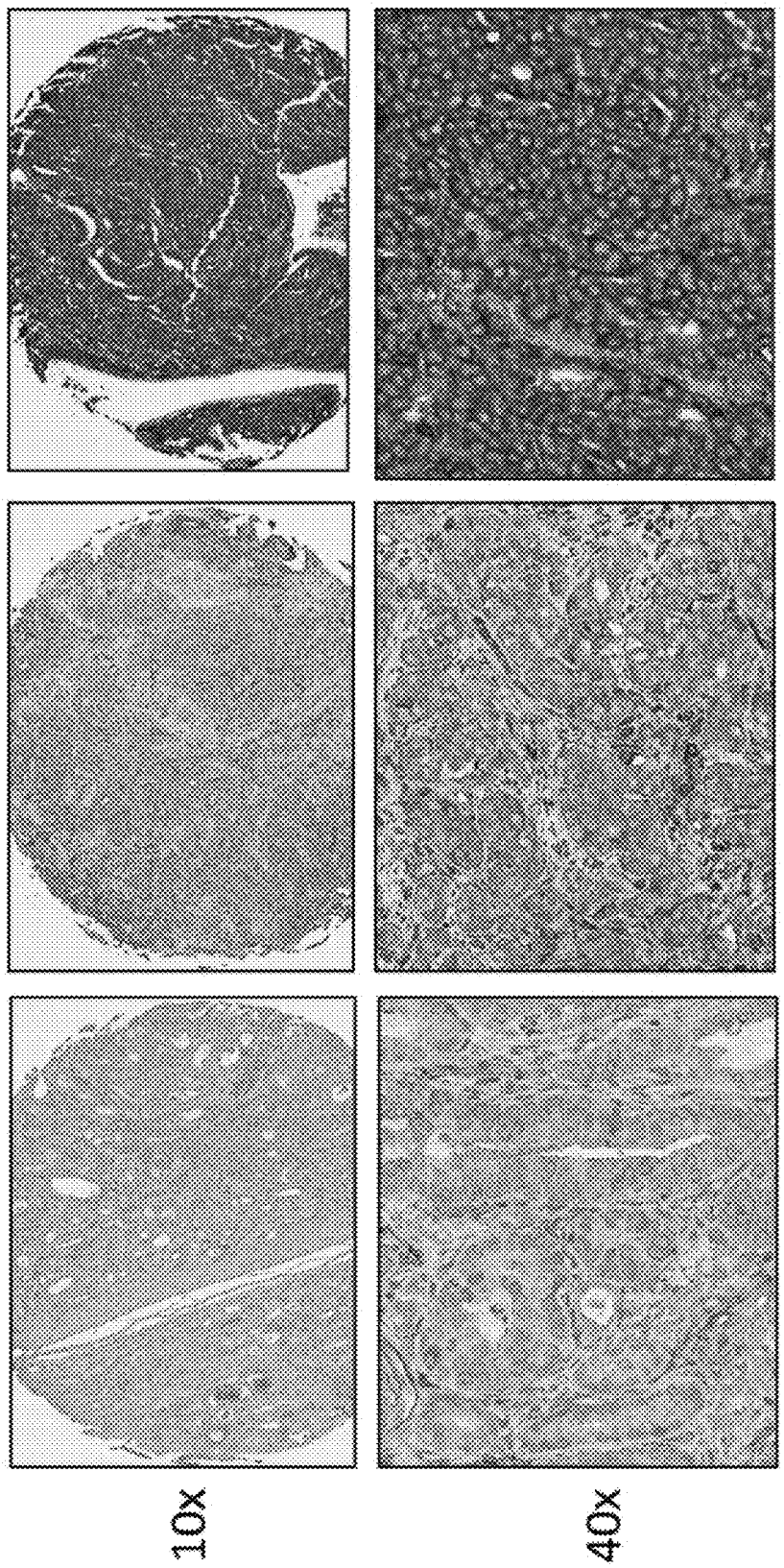
FIGS. 7A-7B. Tissue distribution of cleaved Amphiregulin in solid tumors.
Figure 7B:
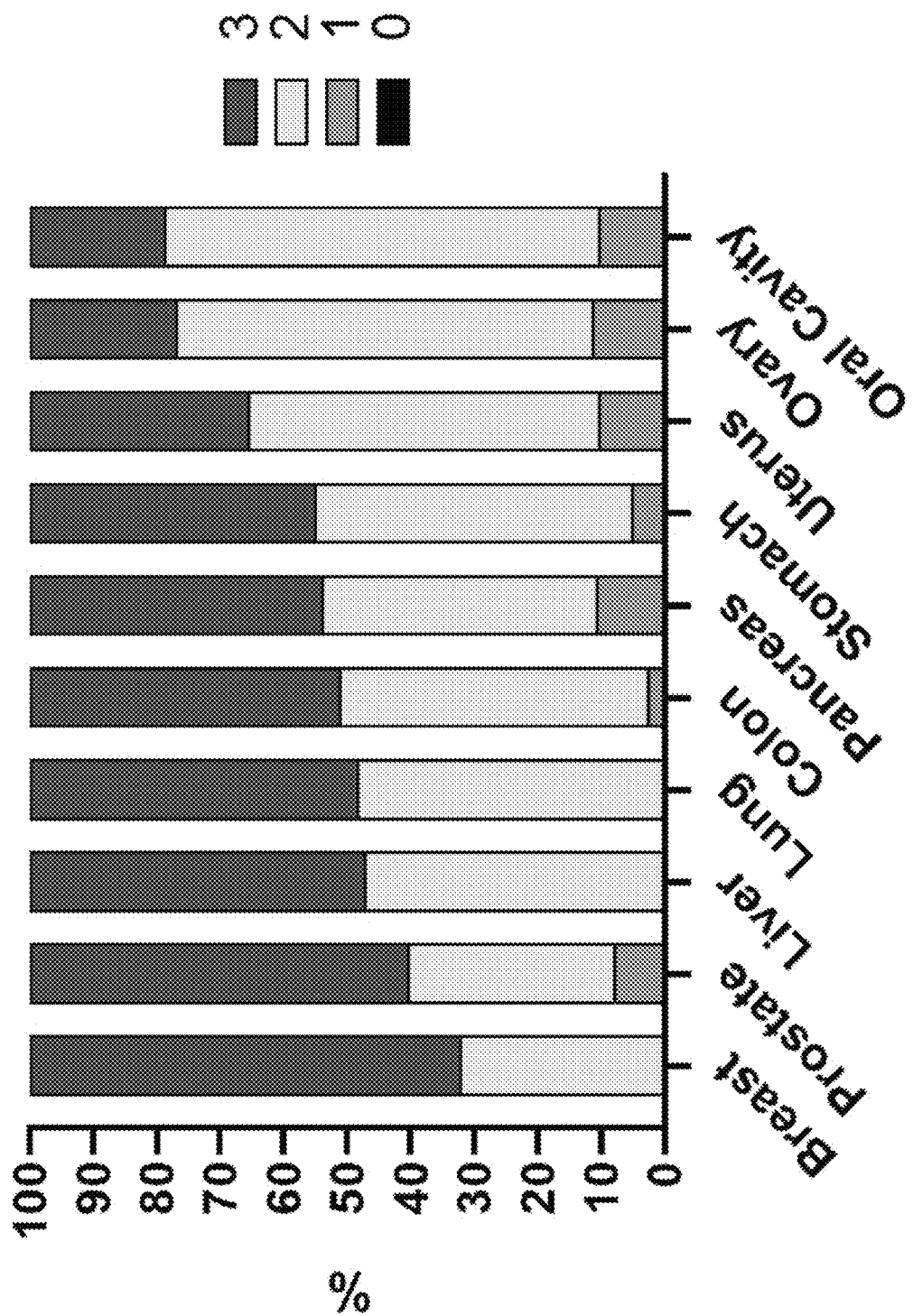
Figure 8A:
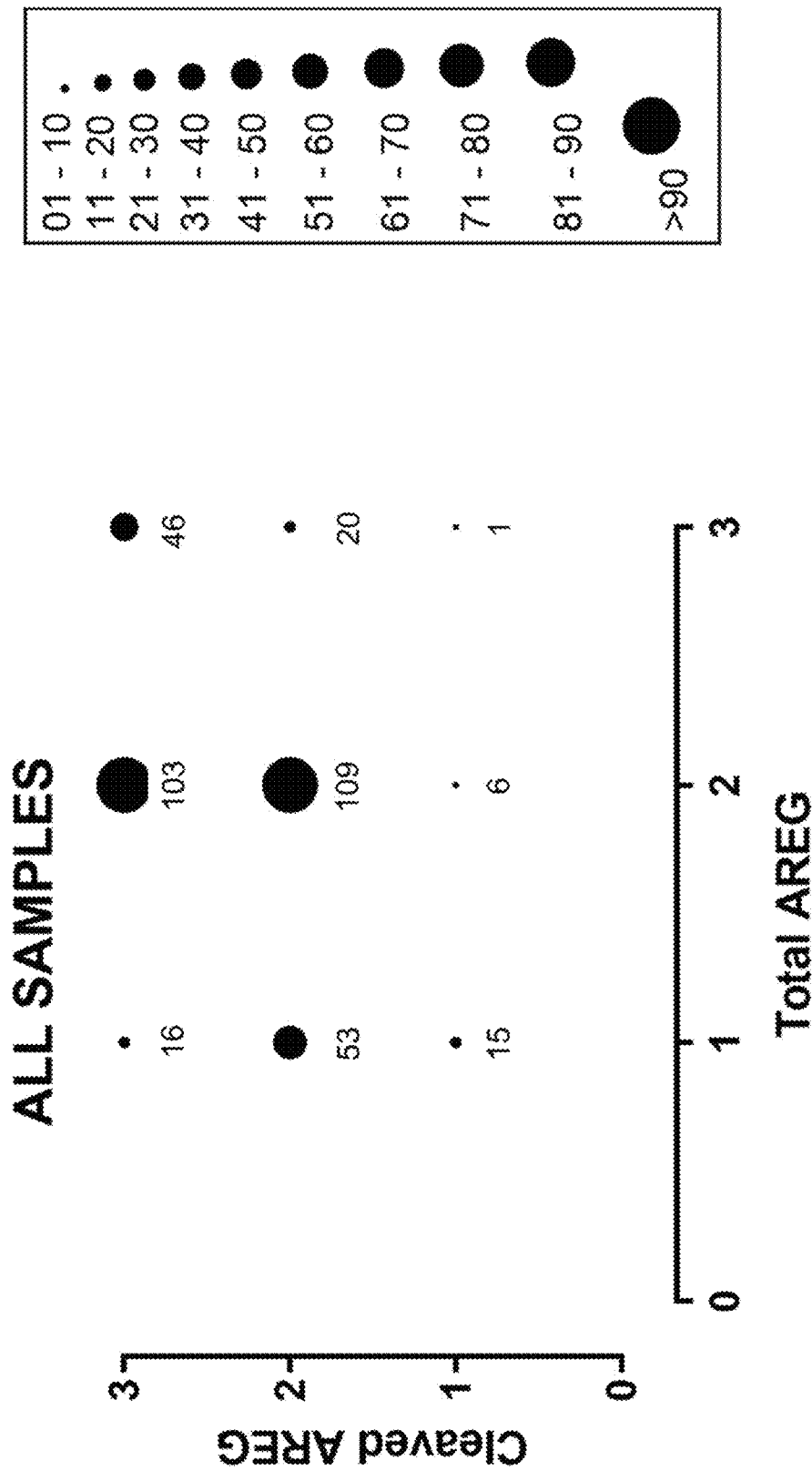
FIGS. 8A-8B. Comparison of levels of cleaved and total Amphiregulin in all 370 tumors.
Figure 8B:
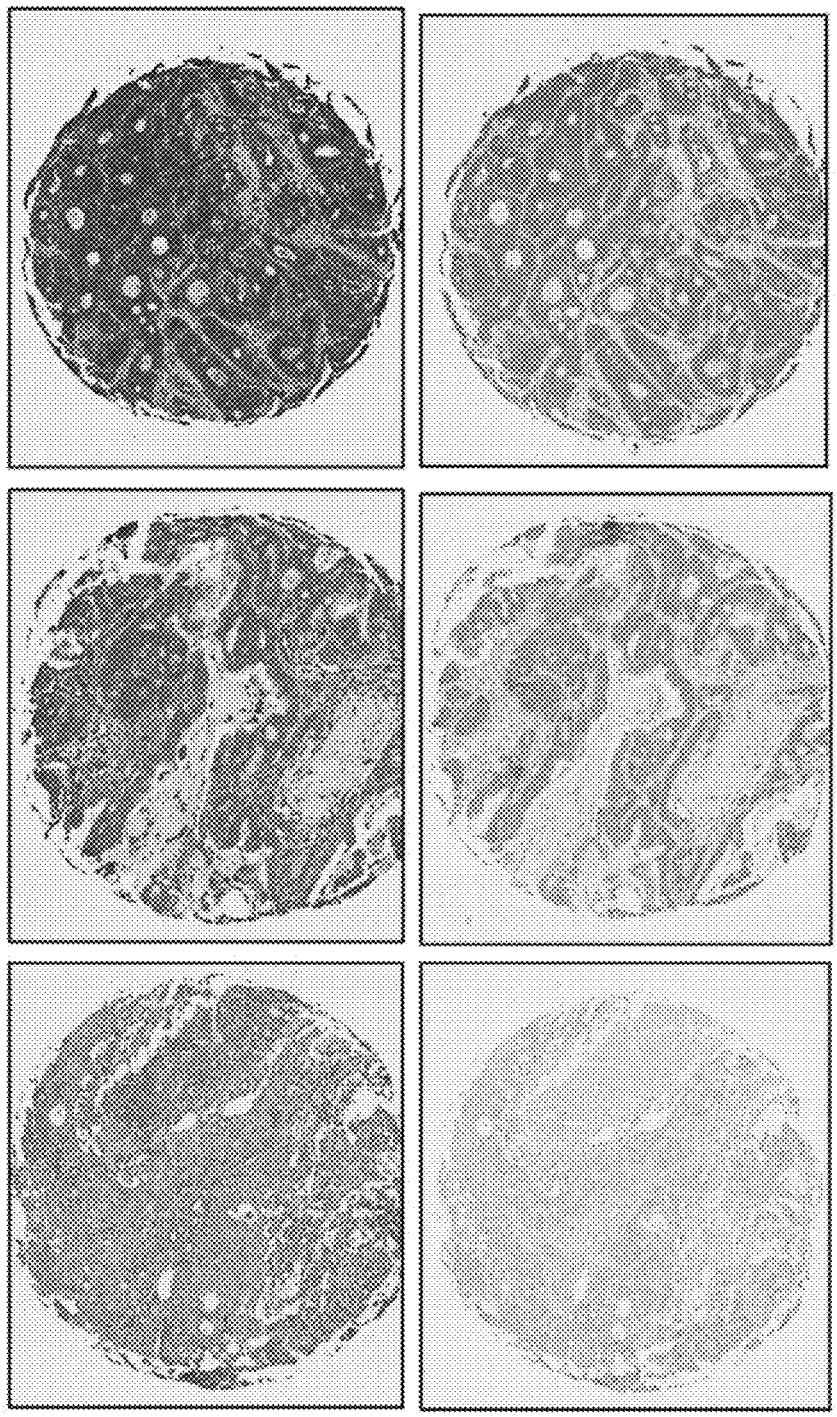
Figure 9A:
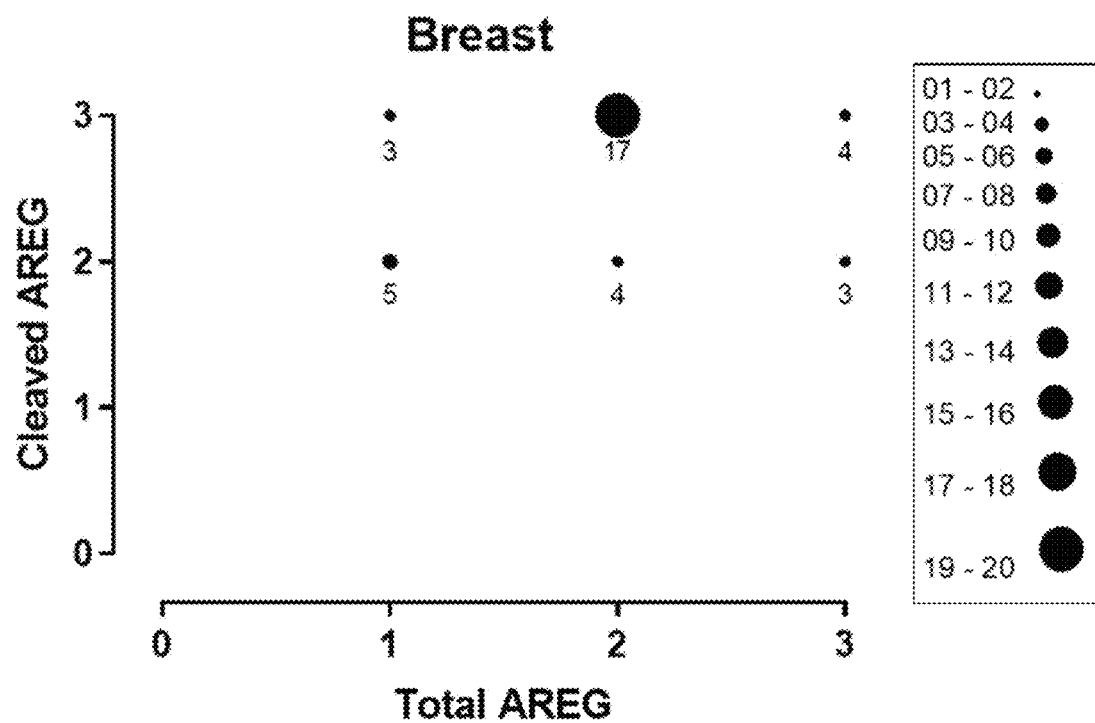
FIGS. 9A-9J. Pairwise comparisons of cleaved and total Amphiregulin levels in ten tumor types. Cross-comparison of intensity scores for both cleaved (Y-axes) and total (X-axes) Amphiregulin in each of the ten indicated tumor types. Data point size is proportional to the number of cases in each pairwise group and the number of cases in each group is indicated.
Figure 9B:
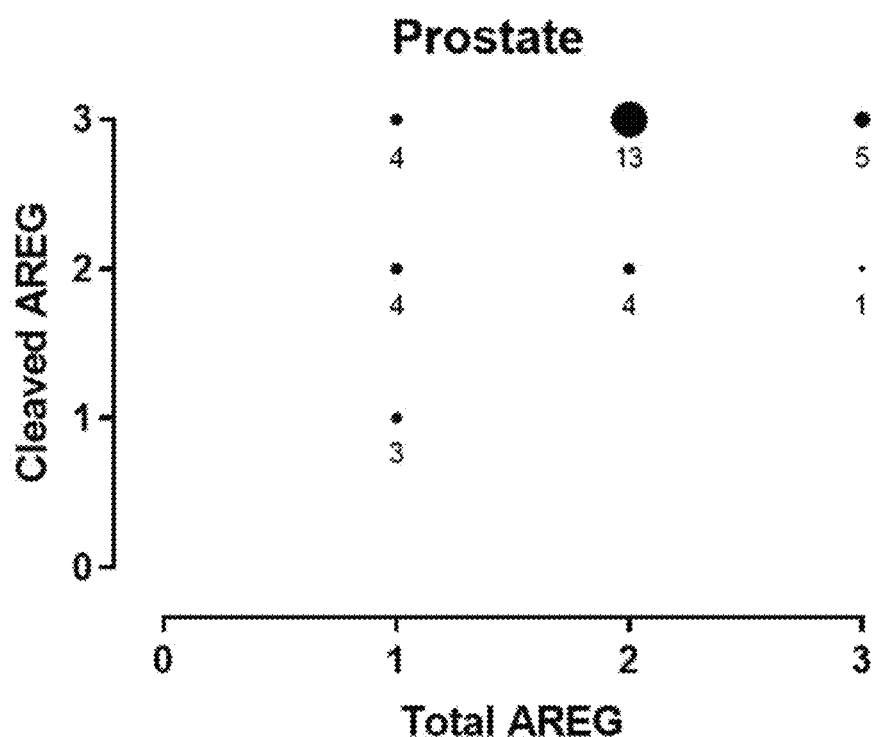
Figure 9C:
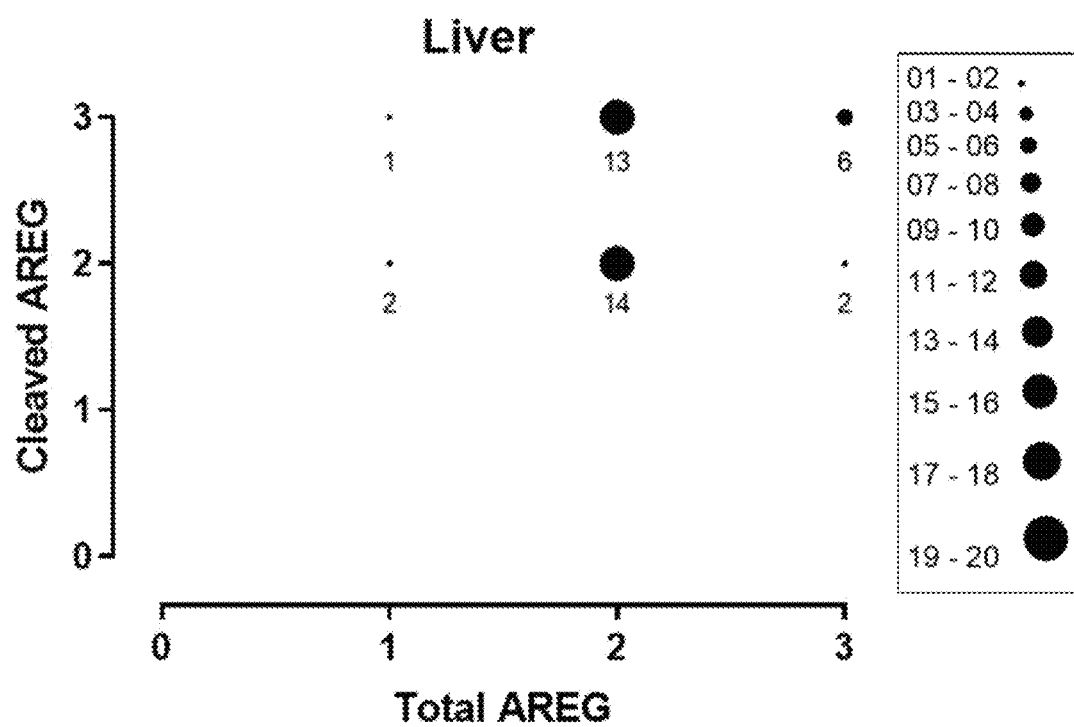
Figure 9D:
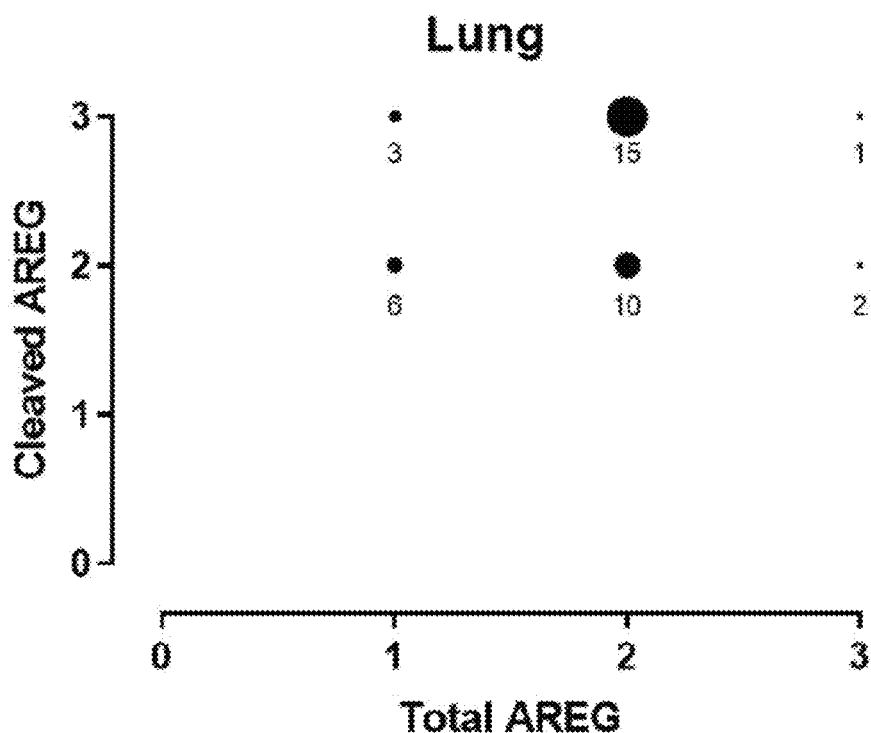
Figure 9E:
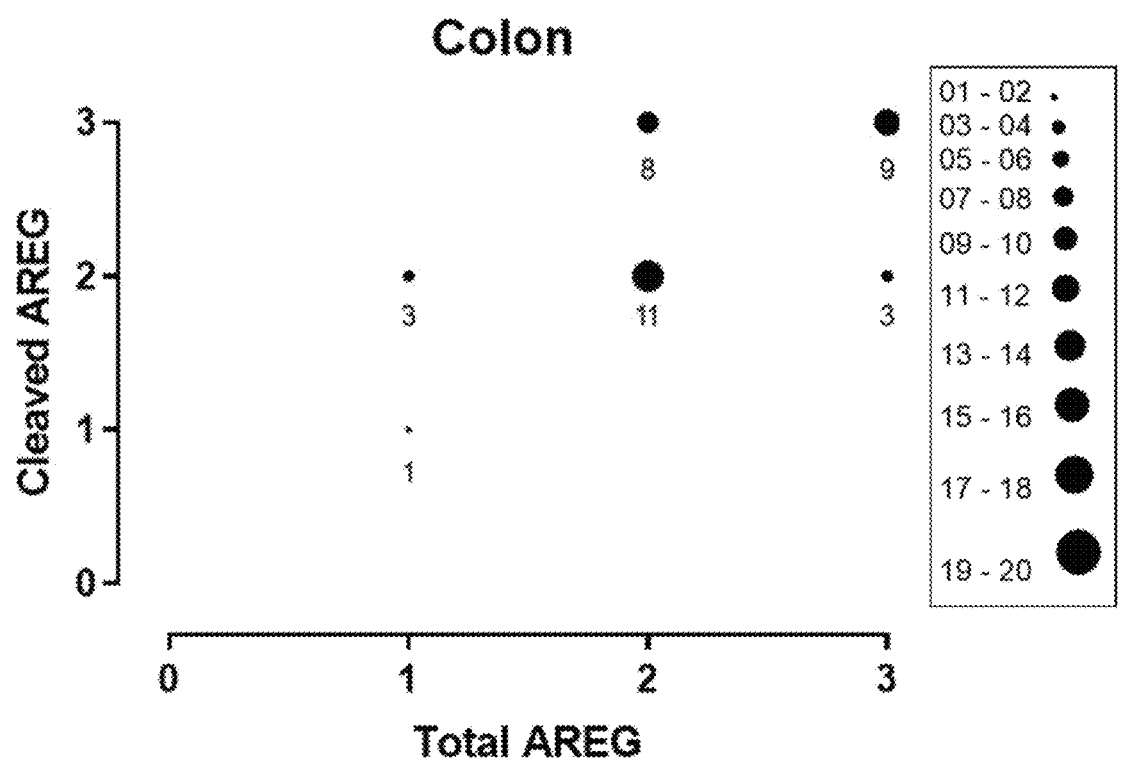
Figure 9F:
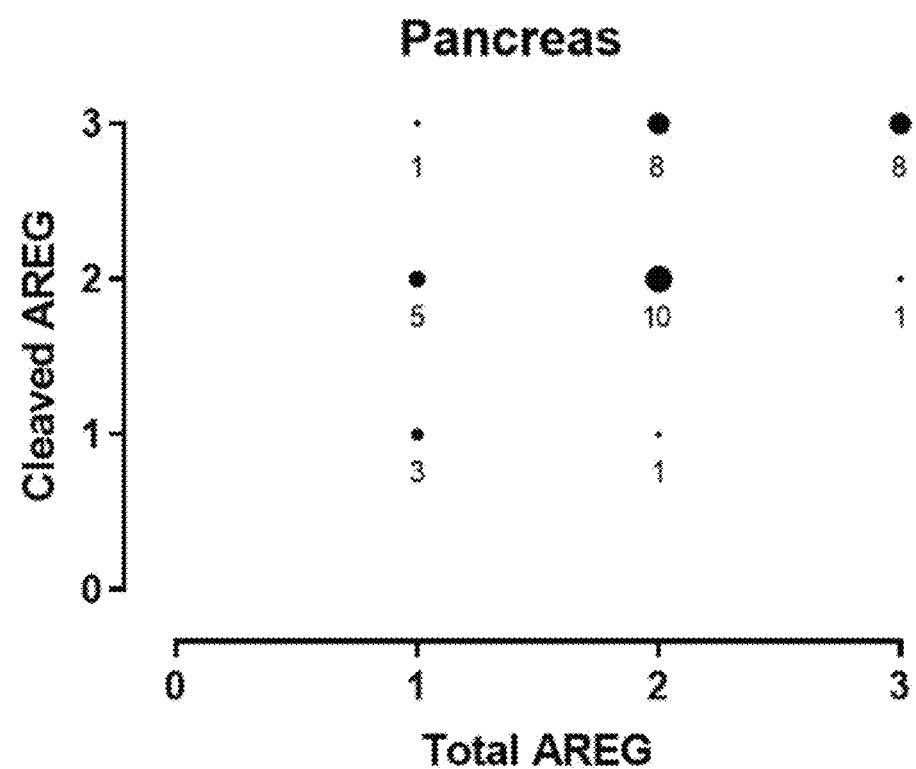
Figure 9G:
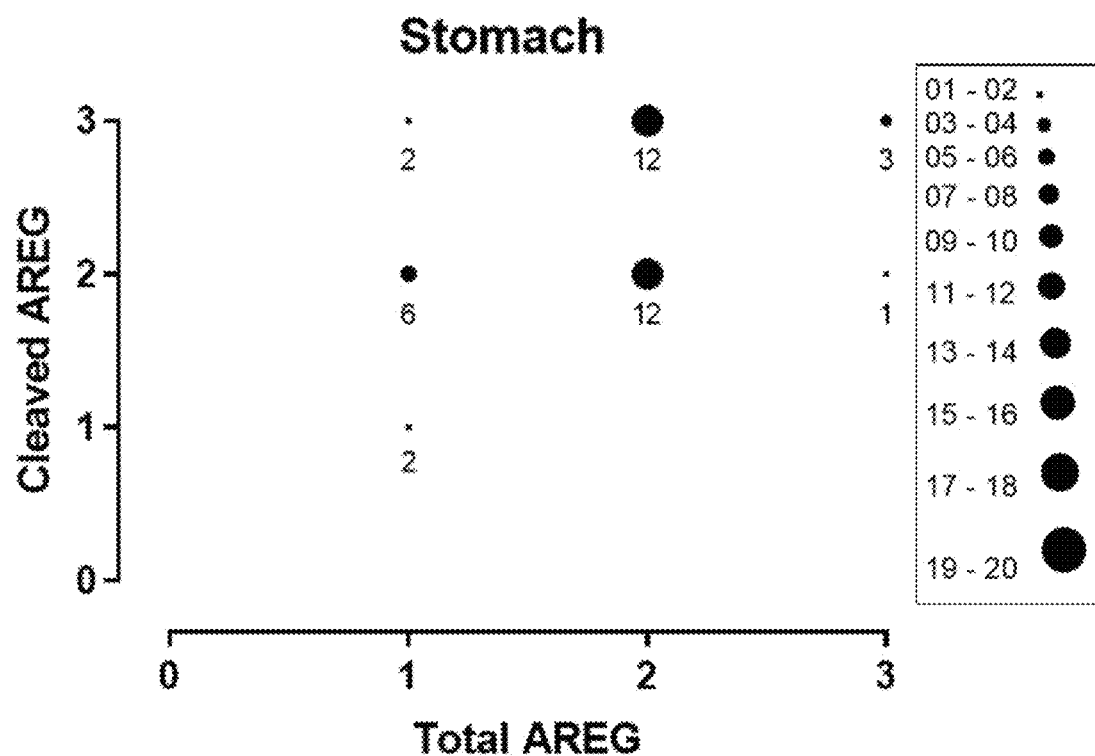
Figure 9H:
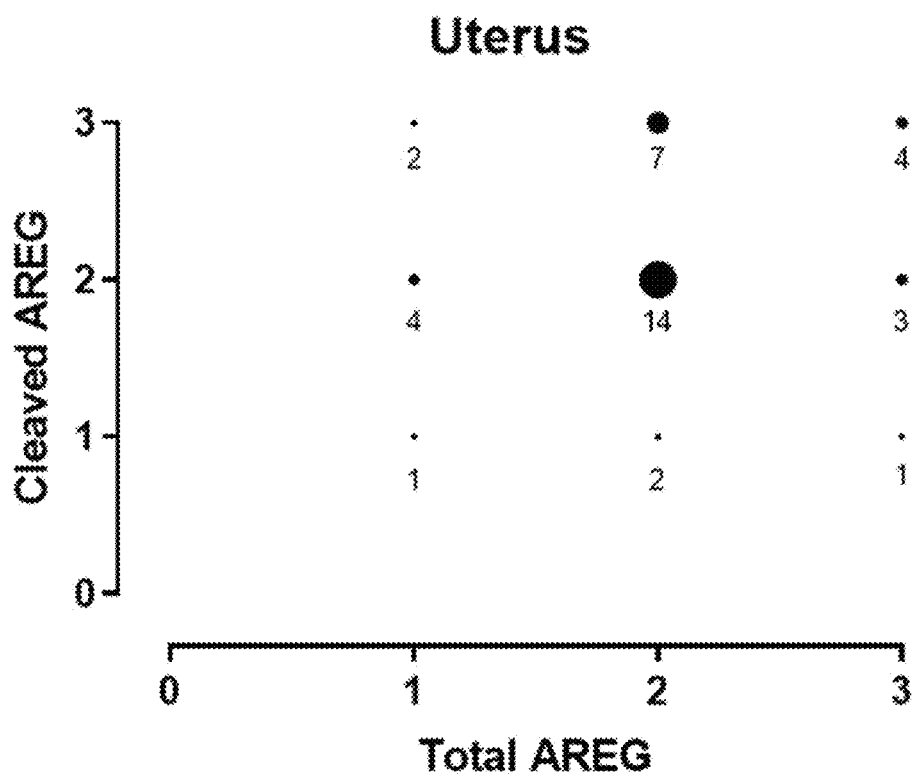
Figure 9I:
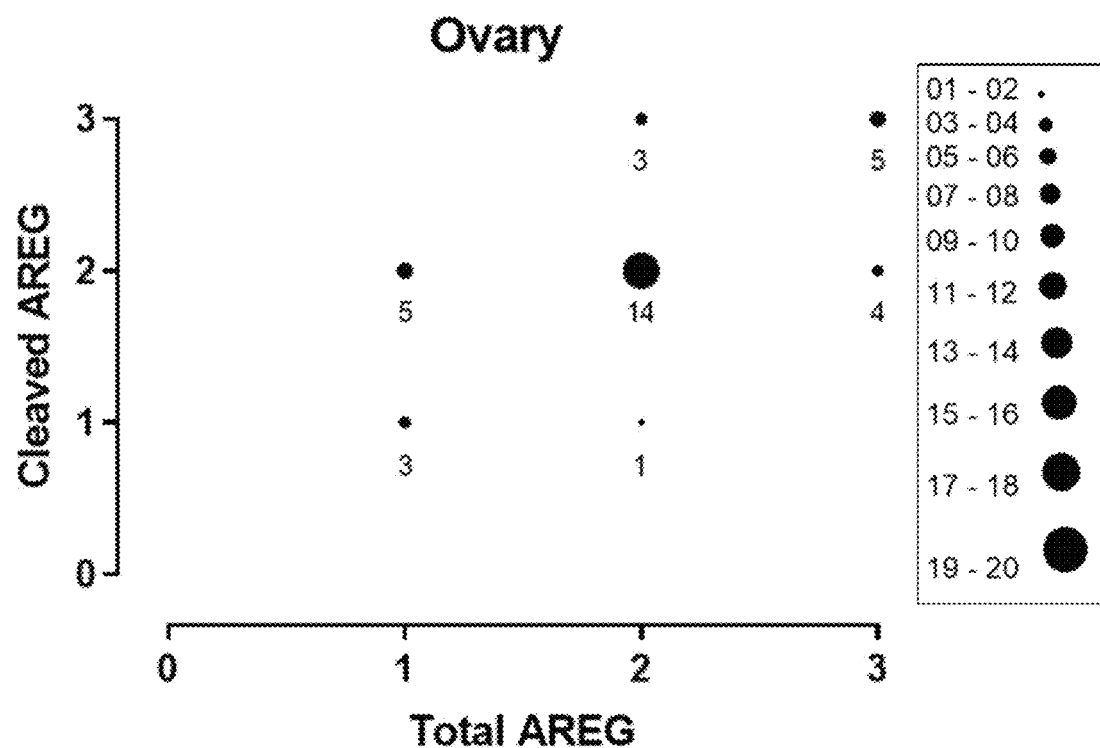
Figure 9J:
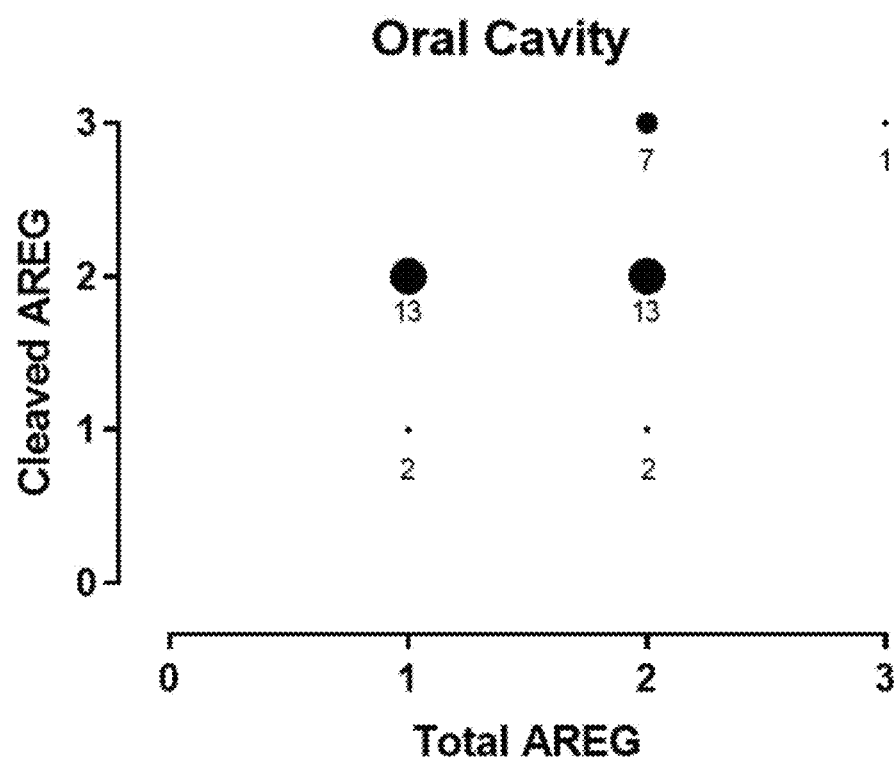

The tissue array design included 380 cores. In the TMA sections used, 370 cores were evaluable for cleaved Amphiregulin (FIGS. 7A and 7B) and 369 were evaluable for both cleaved and total Amphiregulin (FIGS. 8A and 8B).

Results

Tissue Distribution of Cleaved Amphiregulin in Cancer:

To broadly evaluate the levels of cleaved Amphiregulin in cancer, we performed immunohistochemistry on multi-tissue tumor microarrays. The neoplastic compartment of each specimen was scored semi-quantitatively as Negative (0), Low (1), Medium (2) or High (3). No neoplastic cells were negative for 1A3 immunostaining. Representative examples of each staining score are shown in FIG. 7A, and data from all tissues examined are summarized in FIG. 7B. A circumferential staining pattern was especially evident in the high intensity specimens (FIG. 7A, right). At least 50% of breast, prostate, liver and lung tumors stained in the highest score for cleaved Amphiregulin.

Cross-Comparison of Levels of Total and Cleaved Amphiregulin in Cancer:

The specificity of the GMF-1A3 antibody for cleaved Amphiregulin was verified in Example 1 by evaluation of cross-reactivity against peptides representing cleaved and full-length Amphiregulin. If GMF-1A3 antibody immunohistochemistry also accurately reflects cleaved Amphiregulin levels in formalin-fixed tissue then intensity scores for both GMF-1A3 and total Amphiregulin would tend to be positively correlated and, in particular, that cases with low-to-absent expression of total Amphiregulin should be very unlikely to exhibit robust immunostaining with GMF-1A3. We immunostained the tissue microarray with an antibody against total Amphiregulin and cross-compared the intensity scores for each antibody. Data from all tissues are summarized in FIGS. 8A and 8B, and data from individual tissues are shown in FIGS. 9A-9J.

There was a generally positive correlation between total Amphiregulin levels and levels of cleaved Amphiregulin. All specimens had at least some Amphiregulin immunoreactivity and only 16/369 specimens had the highest score for cleaved Amphiregulin and the lowest (but not negative) score for total Amphiregulin. We also noted that cleaved Amphiregulin and total Amphiregulin immunoreactivity were found together in the same tissue compartment (e.g., representative example of medium intensity immunostaining in FIG. 8B). Where we observed a departure from a linear positive relationship between the pair-wise scores (most prominently in breast, prostate, liver and lung, FIGS. 9A-9J), it was in specimens having the highest intensity score for cleaved Amphiregulin with a medium score for total Amphiregulin, suggesting particularly active levels of Amphiregulin processing in these tumors.

DISCUSSION

In this Example, we extended our findings in breast cancer specimens in Example 1 to several additional malignancies, showing that Amphiregulin expression is widespread and, when expressed at moderate to high levels, Amphiregulin cleavage was commonly detected in these specimens. This substantially extends the tissue repertoire where the cleaved Amphiregulin target of the GMF-1A3-MMAE antibody drug conjugate is commonly expressed.

Expression of total Amphiregulin in several of these tissues had previously been described,[6,23-26] but evidence for a functional requirement for Amphiregulin has been limited to a smaller group, including colorectal[27] and breast cancer.[6,28] Our demonstration here that the expressed Amphiregulin is being actively cleaved in a wide range of cancer types confirms that autocrine Amphiregulin signaling following ADAM17-dependent Amphiregulin cleavage is commonly occurring, raising the possibility that Amphiregulin-dependent EGFR activation may be a more frequent mitogenic signal that has been previously appreciated. Accordingly, in addition to being useful as a companion diagnostic for the GMF-1A3-MMAE, this antibody may facilitate a more complete appraisal of the extent of active autocrine Amphiregulin/EGFR signaling in both normal tissue development and homeostasis as well as cancer initiation and progression.

REFERENCES

1. Waks, A G, Winer, E P. Breast cancer treatment: a review. JAMA 2019; 321: 288-300.
2. Clarke, R., Tyson, J. J. and Dixon, J.M. (2015) Endocrine resistance in breast cancer—an overview and update. Mol Cell Endocrinol, 418 Pt 3, 220-234.
3. Gschwind, A, Hart, S, Fischer, O M et al. TACE cleavage of proamphiregulin regulates GPCR-induced proliferation and motility of cancer cells. Embo J 2003; 22: 2411-21.
4. Kenny, P A, Bissell, M J. Targeting TACE-dependent EGFR ligand shedding in breast cancer. J Clin Invest 2007; 117: 337-45.
5. McBryan, J, Howlin, J, Kenny, P A et al. ERalpha-CITED1 co-regulated genes expressed during pubertal mammary gland development: implications for breast cancer prognosis. Oncogene 2007; 26: 6406-19.
6. Peterson, E A, Jenkins, E C, Lofgren, K A et al. Amphiregulin Is a critical downstream effector of estrogen signaling in ERalpha-positive breast cancer. Cancer Res 2015; 75:4830-8.
7. Ciarloni, L, Mallepell, S, Brisken, C. Amphiregulin is an essential mediator of estrogen receptor alpha function in mammary gland development. Proc Natl Acad Sci U SA 2007; 104: 5455-60.
8. Willmarth, N E, Ethier, S P. Autocrine and juxtacrine effects of amphiregulin on the proliferative, invasive, and migratory properties of normal and neoplastic human mammary epithelial cells. J Biol Chem 2006; 281: 37728-37.
9. Busser, B, Sancey, L, Brambilla, E et al. The multiple roles of amphiregulin in human cancer. Biochimica et Biophysica Acta 2011; 1816: 119-31.
10. Barroso-Sousa, R, Tolaney, S M. Clinical development of new antibody-drug conjugates in breast cancer: to infinity and beyond. BioDrugs 2021; 35: 159-74.
11. Fan, M, Yan, P S, Hartman-Frey, C et al. Diverse gene expression and DNA methylation profiles correlate with differential adaptation of breast cancer cells to the anti-estrogens tamoxifen and fulvestrant. Cancer Res 2006; 66: 11954-66.
12. Levano, K S, Kenny, P A. Clarification of the C-terminal proteolytic processing site of human Amphiregulin. FEBS Letters 2012; 586: 3500-2.
13. Sun, M M, Beam, K S, Cerveny, C G et al. Reduction-alkylation strategies for the modification of specific monoclonal antibody disulfides. Bioconjug Chem 2005; 16: 1282-90.

14. Schrama, D, Reisfeld, R A, Becker, J C. Antibody targeted drugs as cancer therapeutics. *Nat Rev Drug Discov* 2006; 5: 147-59.
15. Hamblett, K J, Senter, P D, Chace, D F et al. Effects of drug loading on the antitumor activity of a monoclonal antibody drug conjugate. *Clin Cancer Res* 2004; 10: 7063-70.
16. Akaiwa, M, Dugal-Tessier, J, Mendelsohn, BA. Antibody-drug conjugate payloads; study of Auristatin derivatives. *Chem Pharm Bull* (Tokyo) 2020; 68: 201-11.
17. Lyon, R P, Bovee, T D, Doronina, S O et al. *Reducing hydrophobicity of homogeneous antibody-drug conjugates improves pharmacokinetics and therapeutic index. Nat Biotechnol* 2015; 33: 733-5.
18. Sun, X, Ponte, J F, Yoder, N C et al. Effects of drug-antibody ratio on pharmacokinetics, biodistribution, efficacy, and tolerability of antibody-maytansinoid conjugates. *Bioconjug Chem* 2017; 28: 1371-81.
19. Peters, C, Brown, S. Antibody-drug conjugates as novel anti-cancer chemotherapeutics. *Biosci Rep* 2015; 35: e00225.
20. Lindzen, M, Ghosh, S, Noronha, A et al. Targeting autocrine amphiregulin robustly and reproducibly inhibits ovarian cancer in a syngeneic model: roles for wildtype p53. *Oncogene* 2021; 40: 3665-79.
21. Schmucker, H, Blanding, W M, Mook, J M et al. Amphiregulin regulates proliferation and migration of HER2-positive breast cancer cells. Cell Oncol (Dordr) 2018; 41: 159-68.
22. Lofgren K A, Sreekumar S, Jenkins E C, Jr., Ernzen K J, Kenny P A. Anti-tumor efficacy of an MMAE-conjugated antibody targeting cell surface TACE/ADAM17-cleaved Amphiregulin in breast cancer. Antib Ther 2021; 4(4): 252-61.
23. Bostwick D G, Qian J, Maihle N J. Amphiregulin expression in prostatic intraepithelial neoplasia and adenocarcinoma: a study of 93 cases. Prostate 2004; 58(2): 164-8.
24. Wang B, Yong H, Zhu H, et al. Abnormal amphiregulin expression correlates with gastric cancer prognosis. *Oncotarget* 2016; 7(47): 76684-92.
25. Wang L, Wu H, Wang L, et al. Expression of amphiregulin predicts poor outcome in patients with pancreatic ductal adenocarcinoma. *Diagn Pathol* 2016; 11(1): 60.
26. Yonesaka K, Zejnullahu K, Lindeman N, et al. Autocrine production of amphiregulin predicts sensitivity to both gefitinib and cetuximab in EGFR wild-type cancers. *Clin Cancer Res* 2008; 14(21): 6963-73.
27. Khambata-Ford S, Garrett C R, Meropol N J, et al. Expression of epiregulin and amphiregulin and K-ras mutation status predict disease control in metastatic colorectal cancer patients treated with cetuximab. *Journal of Clinical Oncology* 2007; 25(22): 3230-7.
28. Meier D R, Girtman M A, Lofgren K A, Kenny P A. Amphiregulin deletion strongly attenuates the development of estrogen receptor-positive tumors in p53 mutant mice. *Breast Cancer Res Treat* 2020; 179(3): 653-60.

What is claimed is:

1. An isolated antibody, or an isolated fragment of an antibody, wherein the isolated antibody or the isolated fragment of the antibody is dimensioned and configured to bind to a membrane-associated extracellular portion of a cleaved amphiregulin precursor protein, wherein the membrane-associated extracellular portion has at least 90% sequence identity to an amino acid sequence of SEQ ID NO:2; and the isolated antibody or the isolated fragment of the antibody comprises:
   a heavy chain variable region having at least 90% sequence identity to an amino acid sequence selected from SEQ ID NOs: 3, 5, and 7; and
   a light chain variable region having at least 90% sequence identity to an amino acid sequence selected from SEQ ID NOs: 4, 6, and 8.

2. The isolated antibody, or the isolated fragment of the antibody, of claim 1, wherein the isolated antibody is a human antibody, a humanized antibody, or a chimeric antibody.

3. The isolated antibody of claim 2, wherein the antibody is a monoclonal antibody.

4. The isolated antibody of claim 2, wherein the antibody is a polyclonal antibody.

5. The isolated antibody of claim 2, wherein the antibody is a human antibody.

6. The isolated antibody, or the isolated fragment of the antibody, of claim 1, wherein the isolated fragment of the antibody is a fragment of a human antibody, of a humanized antibody, or of a chimeric antibody.

7. The isolated fragment of the antibody of claim 6, wherein the fragment is of a monoclonal antibody.

8. The isolated fragment of the antibody of claim 6, wherein the fragment is of a polyclonal antibody.

9. The isolated fragment of the antibody of claim 6, wherein the fragment is of a human antibody.

10. The isolated fragment of the antibody of claim 6, wherein the fragment comprises Fab, Fab', F(ab')$_2$, Fd, Fv, complementarity determining region (CDR), or single-chain antibody (scFv).

11. The isolated antibody, or the isolated fragment of the antibody, of claim 1, further comprising a detectable agent, conjugated thereto.

12. The isolated antibody, or the isolated fragment of the antibody, of claim 1, further comprising a cytotoxic agent, conjugated thereto.

13. The isolated antibody, or the isolated fragment of the antibody, of claim 12, wherein the cytotoxic agent is monomethyl auristatin E (MMAE).

14. A pharmaceutical composition comprising the isolated antibody of claim 1, or an isolated fragment thereof.

15. A method of inhibiting proliferation of a tumor cell in a subject, wherein the tumor cell expresses amphiregulin, the method comprising administering to the subject an amount of the antibody, or the fragment of the antibody, of claim 1, conjugated to a cytotoxic agent, wherein the amount is effective to inhibit proliferation of the tumor cell.

16. The method of claim 15, wherein the tumor cell is an ER+ tumor cell.

17. The method of claim 15, wherein the tumor cell is an ER− tumor cell.

18. The method of claim 15, wherein the tumor cell is a breast, prostate, liver, lung, colon, pancreas, stomach, uterus, ovary, or oral cavity tumor cell.

19. The method of claim 15, wherein the cytotoxic agent is MMAE.

20. A method of diagnosing a cancer in a subject, the method comprising contacting a biological sample from the subject with an amount of the antibody, or the fragment of the antibody, of claim 1, wherein at least a portion of the antibody, or the fragment of the antibody selectively binds to the membrane-associated extracellular portion of the cleaved amphiregulin precursor protein.

21. The isolated antibody, or the isolated fragment of the antibody, of claim 1, comprising a heavy chain variable region having at least 90% sequence identity to an amino acid sequence of SEQ ID NO: 3; and/or a light chain variable region having at least 90% sequence identity to an amino acid sequence of SEQ ID NO: 4, with varied amino acids outside CDRs of SEQ ID NOs: 3 and 4.

22. The isolated antibody, or the isolated fragment of the antibody, of claim 1, comprising a heavy chain variable region having at least 90% sequence identity to an amino acid sequence of SEQ ID NO: 5; and/or a light chain variable region having at least 90% sequence identity to an amino acid sequence of SEQ ID NO: 6, with varied amino acids outside CDRs of SEQ ID NOs: 5 and 6.

23. The isolated antibody, or the isolated fragment of the antibody, of claim 1, comprising a heavy chain variable region having at least 90% sequence identity to an amino acid sequence of SEQ ID NO: 7; and/or a light chain variable region having at least 90% sequence identity to an amino acid sequence of SEQ ID NO: 8, with varied amino acids outside CDRs of SEQ ID NOs: 7 and 8.

* * * * *